US008668905B2

(12) United States Patent
Antonia et al.

(10) Patent No.: US 8,668,905 B2
(45) Date of Patent: Mar. 11, 2014

(54) P53 VACCINES FOR THE TREATMENT OF CANCERS

(75) Inventors: Scott Antonia, Land O'Lakes, FL (US);
Dmitry I. Gabrilovich, Tampa, FL (US);
Sunil Chada, Missouri City, TX (US);
Kerstin B. Menander, Bellaire, TX (US)

(73) Assignee: University of South Florida, Tampa, FL (US)

( * ) Notice: Subject to any disclaimer, the term of this patent is extended or adjusted under 35 U.S.C. 154(b) by 581 days.

(21) Appl. No.: 11/433,079

(22) Filed: May 12, 2006

(65) Prior Publication Data

US 2007/0003550 A1    Jan. 4, 2007

Related U.S. Application Data

(60) Provisional application No. 60/680,284, filed on May 12, 2005.

(51) Int. Cl.
*A01N 63/00* (2006.01)
*A01N 65/00* (2009.01)

(52) U.S. Cl.
USPC ........................................ 424/93.21; 424/93.7

(58) Field of Classification Search
None
See application file for complete search history.

(56) References Cited

U.S. PATENT DOCUMENTS

| | | |
|---|---|---|
| 5,580,563 A | 12/1996 | Tam |
| 5,627,025 A | 5/1997 | Steinman et al. |
| 5,633,016 A | 5/1997 | Johnson |
| 5,643,786 A | 7/1997 | Cohen et al. |
| 5,648,219 A | 7/1997 | MacKay et al. |
| 5,679,641 A | 10/1997 | Melief et al. |
| 5,739,169 A | 4/1998 | Ocain et al. |
| 5,747,469 A | 5/1998 | Roth et al. |
| 5,788,963 A | 8/1998 | Murphy et al. |
| 5,798,339 A | 8/1998 | Brandes et al. |
| 5,801,005 A | 9/1998 | Cheever et al. |
| 5,811,297 A | 9/1998 | Gopal |
| 5,824,311 A | 10/1998 | Greene et al. |
| 5,824,346 A | 10/1998 | Dugan |
| 5,830,682 A | 11/1998 | Moore |
| 5,830,880 A | 11/1998 | Sedlacek et al. |
| 5,846,945 A | 12/1998 | McCormick |
| 5,849,589 A | 12/1998 | Tedder et al. |
| 5,851,756 A | 12/1998 | Steinman et al. |
| 5,994,126 A | 11/1999 | Steinman et al. |
| 6,004,807 A | 12/1999 | Banchereau et al. |
| 6,017,527 A | 1/2000 | Maraskovsky et al. |
| 6,051,432 A | 4/2000 | Chokri et al. |
| 6,077,519 A | 6/2000 | Storkus et al. |
| 6,080,409 A | 6/2000 | Laus et al. |
| 6,110,744 A | 8/2000 | Fang et al. |
| 6,274,378 B1 | 8/2001 | Steinman et al. |
| 6,294,654 B1 | 9/2001 | Bogen et al. |
| 6,300,090 B1 | 10/2001 | Steinman et al. |
| 6,455,299 B1 | 9/2002 | Steinman et al. |
| 7,150,992 B1 * | 12/2006 | Lynch et al. ................... 435/377 |
| 2002/0006412 A1 | 1/2002 | Roberts et al. |

FOREIGN PATENT DOCUMENTS

| | | |
|---|---|---|
| EP | 0273085 | 7/1988 |
| EP | 0922758 | 6/1999 |
| WO | WO-94/11514 | 5/1994 |
| WO | WO-97/00954 | 1/1997 |
| WO | WO-97/03703 | 2/1997 |
| WO | WO-97/24447 | 7/1997 |
| WO | WO-97/29183 | 8/1997 |
| WO | WO-98/06863 | 2/1998 |
| WO | WO-99/26662 | 6/1999 |
| WO | WO-99/27958 | 6/1999 |
| WO | WO-99/47180 | 9/1999 |
| WO | WO-00/54839 | 9/2000 |

OTHER PUBLICATIONS

Thomas et al., Nature Reviews Genetics, 2003, 4: 346-358.*
Bangari et al., Curr. Gene. Ther., 2006, 6:215-226.*
Goncalves et al., Bioessays, 2005, 27: 506-517.*
Nadkar et al., Expert Opin. Drug Metab. Toxicol., 2006, 2(5): 753-777.*
Zhivotovsky et al., Semin. Cancer Biol., 2003, 13:125-134.*
Sameshima et al., Oncogene, 1992, 7: 451-457.*
Lowe et al., Cell, 1993, 74: 957-967.*
Petak et al., Pathol. Oncol. Res., 2001, 7(2): 95-106.*
Davies et al., Hematol. Oncol. Clin North Am. 2004, 18:387-416.*
Figoli et al., Cancer Investig., 1988, 6(1): 1-5.*
Vogelstein et al., Trends in Genetics, 1993, 9(4):138-141.*
Komenaka et al., Clin. Derm. 2004, 22: 251-265.*
Li et al., Curr. Pham. Design, 2005, 11:3501-3509.*
Rosenberg et al., Nat Med., 2004, 10(9): 909-915.*
Wen et al., Clin. Cancer Res., 1998, 4:957-962.*

(Continued)

*Primary Examiner* — Hong Sang
(74) *Attorney, Agent, or Firm* — Fulbright & Jaworski LLP

(57) ABSTRACT

The present invention relates to immunotherapy methods for treating hyperproliferative disease in humans, particularly to hyperproliferative disease that is refractory to therapy. More specifically, the invention is directed, in one embodiment, to methods for treating a subject with a hyperproliferative disease in which the expression of a self gene is upregulated in therapy-resistant hyperproliferative cells. In another embodiment, an adenoviral expression construct comprising a self gene under the control of a promoter operable in eukaryotic cells is administered to the therapy-resistant hyperproliferative cells. The present invention thus provides immunotherapies for treating therapy-resistant hyperproliferative disease by attenuating the natural immune system's CTL response against hyperproliferative cells or overexpressing mutant p53 antigens, for example.

35 Claims, 27 Drawing Sheets

(56) References Cited

OTHER PUBLICATIONS

Antonia et al., "Combination of p53 Cancer Vaccine with Chemotherapy in Patients with Extensive Stage Small Cell Lung Cancer," *Clin. Cancer Res.*, 12(3): 878-887, 2006.

Austin-Ward, et al., "Gene therapy and its applications," *Rev. Med. Chil.*, 126(7): 838-45, 1998 [abstract].

Bertholet et al., "Cytotoxic T lymphocyte responses to wild-type and mutant mouse p53 peptides," *Eur. J. Immunol.*, 27(3): 798-801, 1997.

Bonnotte et al., "Intradermal injection, as opposed to subcutaneous injection, enhances immunogenicity and suppresses tumorigenicity of tumor cells," *Cancer Res.*, 63:2145-2149, 2003.

Bronte et al., "IL-2 enhances the function of recombinant poxvirus-based vaccines in the treatment of established pulmonary metastases," *J. Immunol.*, 154: 5282-5292, 1995.

Bukowski et al., "Signal transduction abnormalities in T lymphocytes from patients with advanced renal carcinoma: clinical relevance and effects of cytokine therapy," *Clin. Cancer Res.*, 4(10): 2337-47, 1998.

Caley et al., "Venezuelan equine encephalitis virus vectors expressing HIV-1 proteins: vector design strategies for improved vaccine efficacy," *Vaccine*, 17:3124-35, 1999.

Celluzzi and Falo, "Epidermal dendritic cells induce potent antigen-specific CTL-mediated immunity," *J. Invest. Dermotol.*, 108:716-720, 1997.

Christodoulides et al., "Immunization with recombinant class 1 outer-membrane protein from Neisseria meningitidis: influence of liposomes and adjuvants on antibody avidity, recognition of native protein and the induction of a bactericidal immune response against meningococci," *Microbiology*, 144:3027-37, 1998.

Ciernik et al., "Induction of cytotoxic T lymphocytes and antitumor immunity with DNA vaccines expressing single T cell epitopes," *J. Immunol.*, 156:2369-75, 1996.

Clayman et al., "Adenovirus-mediated p53 gene transfer in patients with advanced recurrent head and neck squamous cell carcinoma," *J. Clinical Oncology*, 16(6):2221-2232, 1998.

Davidson et al., "Intralesional cytokine therapy in cancer: a pilot study of GM-CSF infusion in mesothelioma," *J. Immunother.*, 21:389-98, 1998.

DeLeo, "p53-based immunotherapy of cancer," *Crit. Rev. Immunol.*, 18:29-35, 1998.

Deonarain, "Ligand-targeted receptor-mediated vectors for gene delivery," *Exp. Opin. Ther. Patents*, 8: 53-69, 1998.

Dupuis et al., "Dendritic cells internalize vaccine adjuvant after intramuscular injection," *Cell Immunol.*, 186:18-27, 1998.

Fong et al., "Dendritic Cells in Cancer Immunotherapy," *Annu. Rev. Immunol.*, 18: 245-273, 2000.

Gabrilovich et al., "Decreased antigen presentation by dendritic cells in patients with breast cancer," *Clin. Cancer Res.*, 3(3):483-490, 1997.

Gabrilovich et al., "Dendritic cells in antitumor immune responses. I. Defective antigen presentation in tumor-bearing hosts," *Cell Immunol.*, 170:101-10, 1996.

Gabrilovich et al., "Dendritic cells in antitumor immune responses. II. Dendritic cells grown from bone marrow precursors, but not mature DC from tumor-bearing mice, are effective antigen carriers in the therapy of established tumors," *Cell Immunol.*, 170(1):111-119, 1996.

Gabrilovich et al., "IL-12 and mutant P53 peptide-pulsed dendritic cells for the specific immunotherapy of cancer," *J. Immunother*, 19:414-418, 1996.

Gilbert et al., "Enhanced CD8 T cell immunogenicity and protective efficacy in a mouse malaria model using a recombinant adenoviral vaccine in heterologous prime-boost immunisation regimes," *Vaccine*, 20:1039-1045, 2002.

Gnjatic et al., "Accumulation of the p53 protein allows recognition by human CTL of a wild-type p53 epitope presented by breast carcinomas and melanomas," *J. Immunol.*, 160: 328-333, 1998.

Hanibuchi et al., "Therapeutic efficacy of mouse-human chimeric antiganglioside GM2 monoclonal antibody against multiple organ micrometastases of human lung cancer in NK cell-depleted SCID mice," *Int. J. Cancer*, 78(4):480-485, 1998.

Harvey et al., "Cellular immune response of healthy individuals to intradermal administration of an E1-E3-adenovirus gene transfer vector," *Hum. Gene Ther.*, 10(17):2823-2837, 1999.

Hellstrand et al., "Histamine and cytokine therapy," *Acta. Oncol.*, 37(4):347-53, 1998.

Hirshowitz et al., "Adenovirus-mediated expression of melanoma antigen gp75 as immunotherapy for metastatic melanoma," *Gene Therapy*, 5:975-983, 1998.

Hui and Hashimoto, "Pathways for potentiation of immunogenicity during adjuvant-assisted immunizations with Plasmodium falciparum major merozoite surface protein 1," *Infect. Immun.*, 66(11):5329-36, 1998.

Hurpin et al., "The mode of presentation and route of administration are critical for the induction of immune responses to p53 and antitumor immunity," *Vaccine*, 16:208-215, 1998.

Introgen Therapeutics, Inc., "Novel Cancer Vaccine Sensitizes Tumors to Additional Taxane Chemotherapy," ASCO Abstract #2543, 2005.

Irvine et al., "Cytokine enhancement of DNA immunization leads to effective treatment of established pulmonary metastases," *J. Immunol.*, 156: 238-245, 1996.

Kaiserlian and Etchart, "Epicutaneous and transcutaneous immunization using DNA or proteins," *Eur. J. Dermatol.*, 9:169-176, 1999.

Lipscomb et al., "Dendritic Cells: Immune Regulators in Health and Disease," *Physiol. Rev.*, 82: 97-130, 2002.

Marshall, "Gene Therapy's Growing Pains," *Science*, 269: 1050-1055, 1995.

Mayordomo et al., "Therapy of Murine Tumors with p53 Wild-type and Mutant Sequence Peptide-based Vaccines," *J. Exp. Med.*, 183: 1357-1365, 1996.

McCarty et al., "Sequences required for coordinate induction of adeno-associated virus p19 and p40 promoters by rep protein," *J. Virol.*, 65:2936-2945, 1991.

Miller et al., "Targeted vectors for gene therapy," *FASEB J.*, 9: 190-199, 1995.

Muller-Lander and Nishioka, "p53 in rheumatoid arthritis: friend or foe?" *Arthritis Res.*, 2(3):175-178, 2000.

Munz et al., "Dendritic cell maturation by innate lymphocytes: coordinated stimulation of innate and adaptive immunity," *JEM*, 202: 203-207, 2005.

Nijman et al., "p53, a potential target for tumor-directed T cells," *Immunol. Letters*, 40:171-178, 1994.

Nikitina et al., "An effective immunization and cancer treatment with activated dendritic cells transduced with full-length wild-type p53," *Gene Ther.*, 9(5): 345-352, 2002.

Obara et al., "Site-Directed Mutagenesis of the Cell-Binding Domain of Human Fibronectin: Separable, Synergistic Sites Mediate Adhesive Function," *Cell*, 649-657, 1988.

Orkin et al., "Report and Recommendations of the Panel to Assess the NIH Investment in Research on Gene Therapy," 1995.

Perricone et al., "Immunogene therapy for murine melanoma using recombinant adenoviral vectors expressing melanoma-associated antigens," *Mol. Ther.*, 1(3):275-284, 2000.

Pietras et al., "Remission of human breast cancer xenografts on therapy with humanized monoclonal antibody to HER-2 receptor and DNA-reactive drugs," *Oncogene*, 17(17):2235-49, 1998.

Racher et al., "Culture of 293 cells in different culture systems: cell growth and recombinant adenovirus production," *Biotechnology Techniques*, 9:169-174, 1995.

Raz et al., "Intradermal gene immunization: The possible role of DNA uptake in the induction of cellular immunity to viruses," *Proc. Natl. Acad. Sci.*, 91:9519-9523, 1994.

Reed et al., "Construction and Characterization of a Recombinant Adenovirus Directing Expression of the Mage-1 Tumor-Specific Antigen," *Int. J. Cancer*, 72: 1045-1055, 1997.

Restifo et al., "Molecular mechanisms used by tumors to escape immune recognition: immunogenetherapy and the cell biology of major histocompatibility complex class 1," *Journal of Immunotherapy*, 14: 182-190, 1993.

(56) References Cited

OTHER PUBLICATIONS

Ridge et al., "A conditioned dendritic cell can be a temporal bridge between a CD4+ T-helper and a T-killer cell," *Nature*, 393: 474-478, 1998.
Ropke et al., "Spontaneous human squamous cell carcinomas are killed by a human cytotoxic T lymphocyte clone recognizing a wild-type p53-derived peptide," *Proc. Natl. Acad. Sci. USA*, 93:14704-14707, 1996.
Rosenthal et al., "Augmentation of antitumor immunity by tumor cells tranduced with a retroviral vector carrying the interleukin-2 and interferon-γ cDNAs," *Blood*, 83(5):1289-1298, 1994.
Roth, "Dendritic cell based p53 vaccine for treatment of small cell lung cancer," International Society for Cell & Gene Therapy of Cancer (ISCGT) meeting, Shenzhen, China, Dec. 9-11, 2005.
Roth et al., "p53 as a target for cancer vaccines: Recombinant canarypox virus vectors expressing p53 protect mice against lethal tumor cell challenge," *Proc. Natl. Acad. Sci. USA*, 93: 4781-4786, 1996.
Saurwein-Teissl et al., "Whole virus influenza vaccine activates dendritic cells (DC) and stimulates cytokine production by peripheral blood mononuclear cells (PBMC) while subunit vaccines support T cell proliferation," *Clin. Exp. Immunol.*, 114(2):271-276, 1998.
Sonderbye et al., "In vivo and in vitro modulation of immune stimulatory capacity of primary dendritic cells by adenovirus-mediated gene transduction," *Exp. Clin. Immunogenet.*, 15(2):100-111, 1998.
Steinman, "The dendritic cell system and its role in immunogenecity," *Annu. Rev. Immunol.*, 9:271-296, 1991.
Theobald et al., "Targeting p53 as a general tumor antigen," *Proc. Natl. Acad. Sci. USA*, 92:11993-11997, 1995.
Tuting et al., "Genetically modified bone marrow-derived dendritic cells expressing tumor-associated viral or "self" antigens induce antitumor immunity in vivo," *Eur. J. Immuno.*, 27: 2702-2707, 1997.
Verma et al., "Gene therapy—promises, problems and prospects," *Nature*, 389: 239-242, 1997.
Vogelstein et al., "The multistep nature of cancer," *Cell*, 61: 757-767, 1990.
Wan et al.,"Dendritic cells transduced with an adenoviral vector encoding a model tumor-associated antigen for tumor vaccination," *Hum. Gene. Ther.* 8:1355-1363, 1997.
Xiang et al., "Manipulation of the Immune Response to a Plasmid-encoded Viral Antigen by Coinoculation with Plasmids Expressing Cytokines," *Immunity*, 2: 129-135, 1995.
Yanuck et al., A mutant p53 tumor suppressor protein is a target for peptide-induced CD8+ cytotoxic T-cells, *Cancer Res.*, 53(14):3257-61, 1993.
Yu et al., "Dendritic cells transduced with full-length wild-type p53 generate antitumor cytotoxic T lymphocytes from peripheral blood of cancer patients," *Clin. Can. Res.*, 7:127-135, 2001.
Zitvogel et al., "Therapy of murine tumors with tumor peptide-pulsed dendritic cells: dependence on T cells, B7 costimulation, and T helper cell 1-associated cytokines," *J. Exp. Med.*, 183:87-97, 1996.
Chada, et al., "Development of vaccines against self-antigens: The p53 paradigm", Current Opinion in Drug Discovery and Development, Current Drugs, London, 2003, vol. 6 (2), pp. 169-173.
Gabrilovich, D., "Dendritic cell vaccines for cancer treatment", Current Opinion in Molecular Therapeutics, 2002, vol. 4 (5), pp. 452-458.
Ishida, T., et al., "Dendritic cells transduced with wild-type p53 gene elicit potent anti-tumour immune responses", Clin. Exp. Immunology, 1999, vol. 117, pp. 244-251.
Nikitina, E., et al., "Dendritic Cells Transduced with Full-Length Wild-Type p53 Generate Antitumor Cytotoxic T Lymphocytes from Peripheral Blood of Cancer Patients", Clinical Cancer Research, 2001, vol. 7, pp. 127-135.
Ardizzoni, "Topotecan, a new active drug in the second-line treatment of small-cell lung cancer: A phase II study in patients with refractory and sensitive disease," *Journal of Clinical Oncology*, 15(5):2090-2096, 1997.
Corthay et al., "Immunotherapy in multiple myeloma: Id-specific strategies suggested by stuties in animal models," *Cancer Immunol Immunother*, 53:759-769, 2004.
Curiel, "Tergs and rethinking cancer immunotherapy," *The Journal of Clinical Investigation*, 117(5):1167-1174, 2007.
Finn, "Cancer immunology," *The New England Journal of Medicine*, 358(25):2704-2715 2008.
Kaneno et al., "Chemomodulation of human dendritic cell function by antineoplastic agents in low noncytotoxic concentrations," *Journal of Translational Medicine*, 7:58, 2009.
Lake and Robinson, "Immunotherapy and chemotherapy—a practical partnership," *Nat Rev Cancer*, 5:397-404, 2005.
Mapara and Sykes, "Tolerance and cancer: mechanisms of tumor evasion and strategies for breaking tolerance," *Journal of Clinical Oncology*, 22(6):1136-1151, 2004.
Marigo et al., "Tumor-induced tolerance and immune suppression by myeloid derived suppressor cells," *Immunological Reviews*, 222:162-179, 2008.
Marincola et al., "Escape of human solid tumors from T-cell recognition: molecular mechanisms and functional significance," *Advances in Immunology*, 74:181-273, 2000.
Masters et al., "Phase II trial of gemcitabine in refractory or relapsed small-cell lung cancer: Eastern Cooperative Oncology Group trial 1597," *Journal of Clinical Oncology*, 21(8):1550-1555, 2003.
Sandler, "Irinotecan in small-cell lung cancer: the US experience," *Oncology*, 15(1 Suppl 1):11-12, 2001.
Shurin et al., "Chemotherapeutic agents in noncytotoxic concentrations increase antigen presentation by dendritic cells via an IL-12-dependent mechanism," *The Journal of Immunology*, 183:137-144, 2009.
Speiser et al., "Self antigens expressed by solid tumors do not efficiently stimulate naïve or activated T cells: Implications for immunotherapy," *J. Exp. Med.*, 186(5):645-653, 1997.
Tanaka et al., "Classification of chemotherapeutic agents based on their differential In vitro effects on dendritic cells," *Cancer Res*, 69(17):6978-6986, 2009.
Yu et al., "Effective combination of chemotherapy and dendritic cell administration for the treatment of advanced-stage experimental breast cancer," *Clinical Cancer Research*, 9:285-294, 2003.

* cited by examiner

Response to second line CTX

| Patient # | TTP (1st line CTX) | 2nd line CTX | Response to 2nd line CTX |
|---|---|---|---|
| 1 | 0 | Taxol | *SD* |
| 2 | 2 | Taxol | PR |
| 3 |  | CDDP/CPT-11 | PR |
| 4 | 2 | Taxol | *SD* |
| 5 | 2 | Taxol | PR |
| 6 | 0 | Taxol | PR |
| 8 | 0 | Taxol | PD |
| 9 | 4 | CDDP/CPT-11 | PR |
| 10 | 0 | Taxol | PR |
| 11 | 2 | Topotecan | PD |
| 12 | 3 | Carbo/VP16 | PR |
| 20 | 2 | Taxol | PD |
| 21 | 4 | Taxol | PD |

FIG. 6

Drug activity in resistant SCLC

| Drug | N= | RR | Median Survival | Reference |
|---|---|---|---|---|
| Taxol | 24 | 29% | 3.3 mo | Smit, 1998 |
| Isofosfamide | 14 | 43% | | Cantwell, 1998 |
| Topotecan | 47 | 6% | 4.7 mo | Ardizonni, 1997 |
| Etoposide | 11 | 6.4% | 3.5 mo | Johnson, 1990 |
| CDDP/VP16 | 39 | 23%<br>28% | | Fukkuoka, 1991<br>Roth, 1992 |
| CDDP/ topotecan | 42 | 24% | 6.1 mo | Ardizonni, 2003 |
| Advexin/CTX | 13 | 54% | 9+ mo | |

FIG. 7

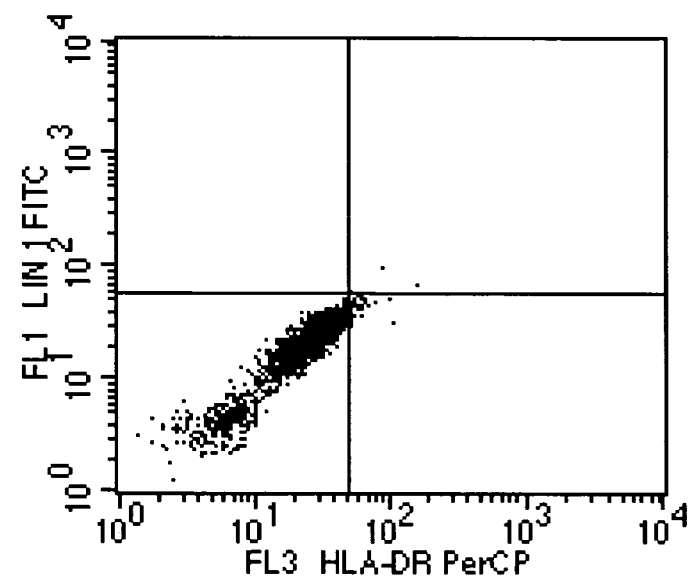
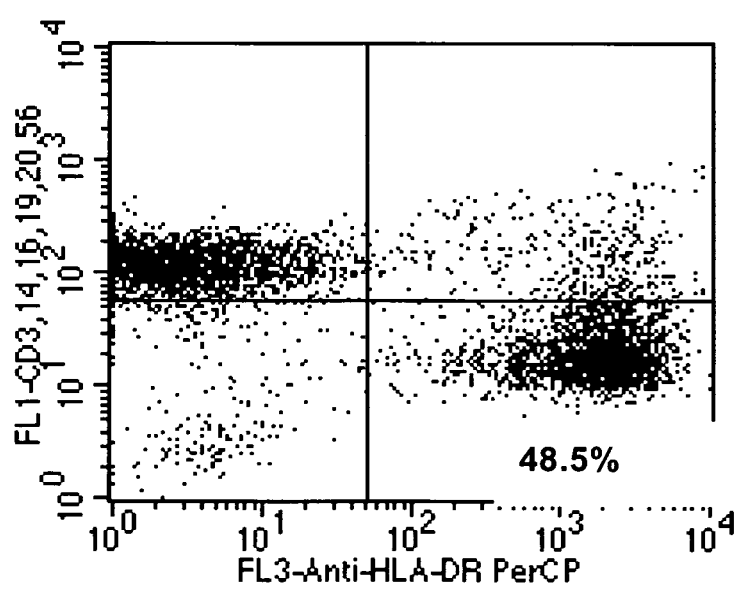
FIG. 10

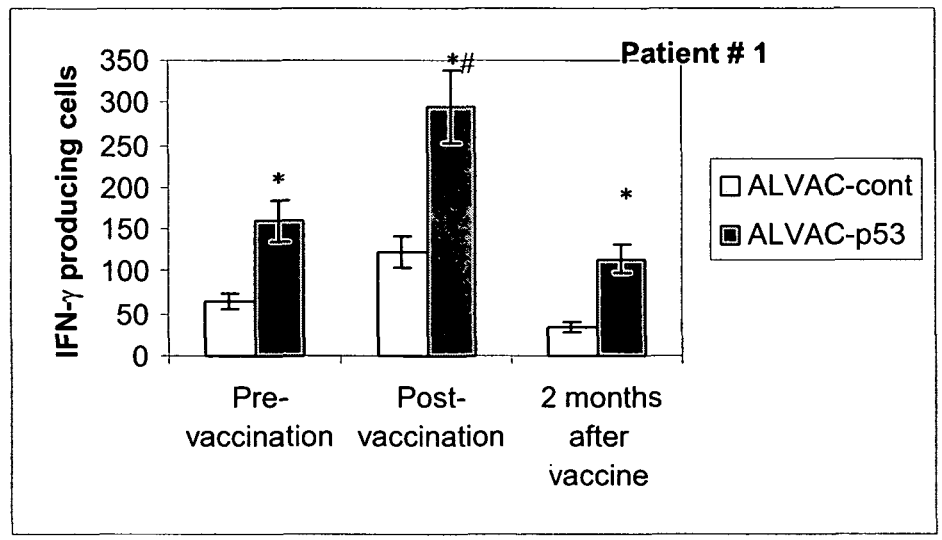
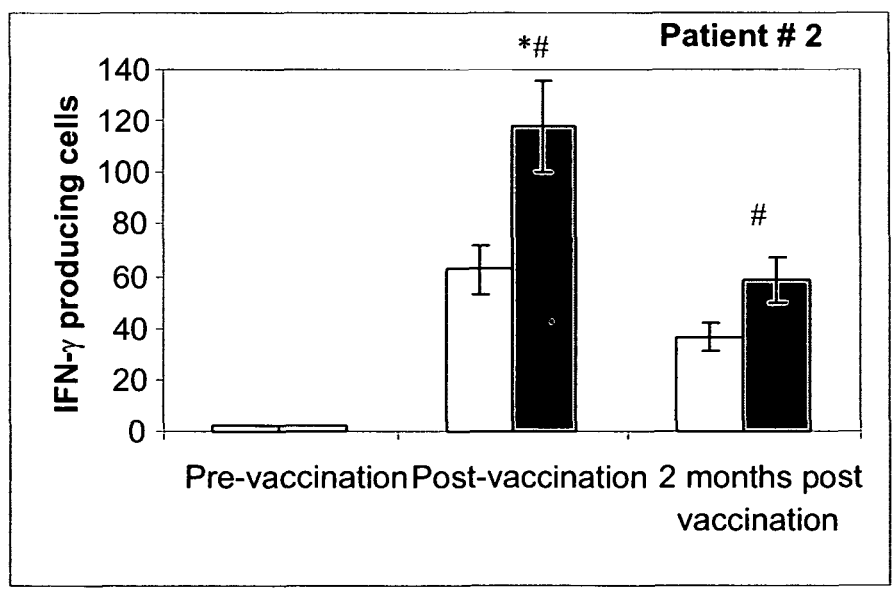
FIG. 11A

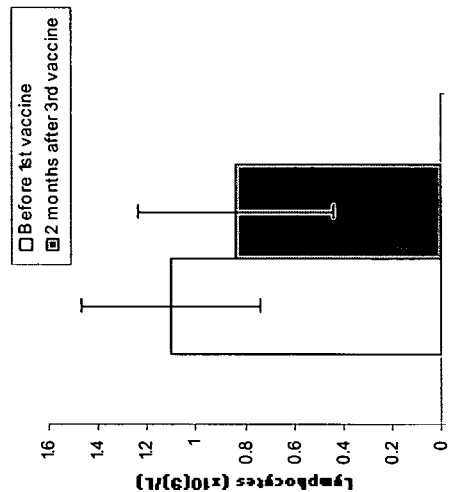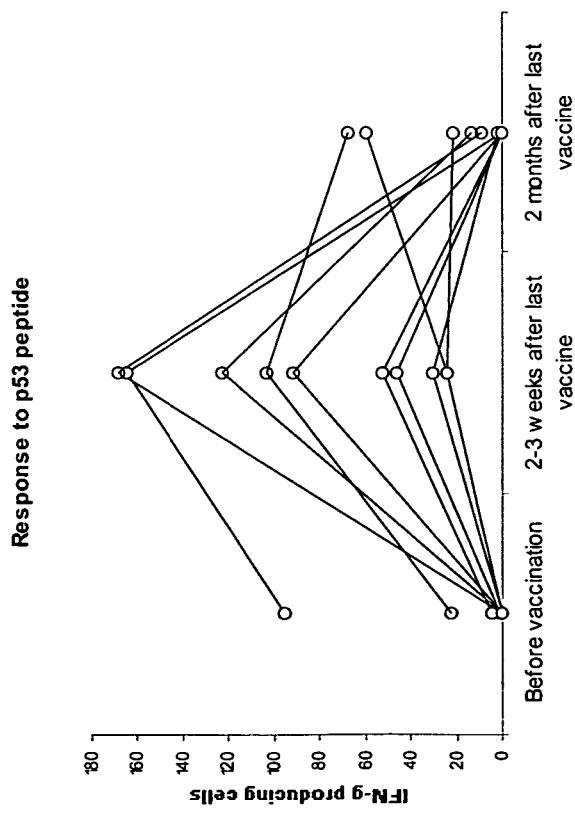
FIG. 17

SEQUENCE LISTING

```
<160> NUMBER OF SEQ ID NOS: 3

<210> SEQ ID NO 1
<211> LENGTH: 1303
<212> TYPE: DNA
<213> ORGANISM: Homo sapiens

<400> SEQUENCE: 1
gtccaggagc aggtagctgc tgggctccgg ggacactttg cgttcgggct gggagcgtgc        60
tttccacgac ggtgacacgc ttccctggat tggcagccag actgccttcc gggtcactgc       120
```

```
catggaggag ccgcagtcag atcctagcgt cgagccccct ctgagtcagg aaacattttc      180
agacctatgg aaactacttc ctgaaaacaa cgttctgtcc cccttgccgt cccaagcaat      240
ggatgatttg atgctgtccc cggacgatat tgaacaatgg ttcactgaag acccaggtcc      300
agatgaagct cccagaatgc cagaggctgc tcccccccgtg gcccctgcac cagcgactcc     360
tacaccggcg gcccctgcac cagcccccctc ctggccctg tcatcttctg tcccttccca     420
gaaaacctac cagggcagct acggtttccg tctgggcttc ttgcattctg ggacagccaa     480
gtctgtgact tgcacgtact ccctgccct caacaagatg ttttgccaac tggccaagac      540
ctgccctgtg cagctgtggg ttgattccac acccccgccc ggcacccgcg tccgcgccat     600
ggccatctac aagcagtcac agcacatgac ggaggttgtg aggcgctgcc cccaccatga     660
gcgctgctca gatagcgatg gtctggcccc tcctcagcat cttatccgag tggaaggaaa     720
tttgcgtgtg gagtatttgg atgacagaaa cacttttcga catagtgtgg tggtgcccta    780
tgagccgcct gaggttggct ctgactgtac caccatccac tacaactaca tgtgtaacag    840
ttcctgcatg ggcggcatga accggaggcc catcctcacc atcatcacac tggaagactc    900
cagtggtaat ctactgggac ggaacagctt tgaggtgcgt gtttgtgcct gtcctgggag    960
agaccggcgc acagaggaag agaatctccg caagaaaggg gagcctcacc acgagctgcc   1020
cccagggagc actaagcgag cactgcccaa caacaccagc tcctctcccc agccaaagaa    1080
gaaaccactg gatggagaat atttcaccct tcagatccgt gggcgtgagc gcttcgagat    1140
gttccgagag ctgaatgagg ccttggaact caaggatgcc caggctggga aggagccagg   1200
ggggagcagg gctcactcca gccacctgaa gtccaaaaag ggtcagtcta cctcccgcca    1260
taaaaaactc atgttcaaga cagaagggcc tgactcagac tga                      1303
```

```
<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

Phe Leu Thr Pro Lys Lys Leu Gln Cys Val
 1               5                  10

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3

Leu Leu Gly Arg Asn Ser Phe Glu Val
 1               5
```

P53 VACCINES FOR THE TREATMENT OF CANCERS

The present invention claims priority to U.S. Provisional Patent Application Ser. No. 60/680,284, filed May 12, 2005, which is incorporated by reference herein in its entirety.

STATEMENT REGARDING FEDERALLY SPONSORED RESEARCH OR DEVELOPMENT

The present invention utilized funds from grant number CA61242 from the National Cancer Institute. The United States Government may have certain rights in the invention.

FIELD OF THE INVENTION

The present invention relates generally to at least the fields of cell biology, immunology, molecular biology, and cancer therapy. More particularly, it concerns a method of eliciting or promoting an immune response, such as a cytotoxic T lymphocyte response directed against self gene antigens presented by hyperproliferative cells that are resistant to at least one hyperproliferative disease treatment.

BACKGROUND OF THE INVENTION

Normal tissue homeostasis is a highly regulated process of cell proliferation and cell death, and an imbalance of either cell proliferation or cell death can develop into a cancerous state (Solyanik et al., 1995; Stokke et al., 1997; Mumby and Walter, 1991; Natoli et al., 1998; Magi-Galluzzi et al., 1998). The maintenance of cell proliferation and cell death is at least partially regulated by proto-oncogenes. A proto-oncogene can encode proteins that induce cellular proliferation (e.g., sis, erbB, src, ras and myc), proteins that inhibit cellular proliferation (e.g., Rb, p53, NF1 and WT1) or proteins that regulate programmed cell death (e.g., bcl-2) (Ochi et al., 1998; Johnson and Hamdy, 1998; Liebermann et al., 1998). However, genetic rearrangements or mutations to these proto-oncogenes results in the conversion of a proto-oncogene into a potent cancer causing oncogene. Often, a single point mutation is enough to transform a proto-oncogene into an oncogene. For example, a point mutation in the p53 tumor suppressor protein results in the complete loss of wild-type p53 function (Vogelstein and Kinzler, 1992; Fulchi et al., 1998) and acquisition of "dominant" tumor promoting function.

Immunotherapy, a rapidly evolving area in cancer research, is one option for the treatment of certain types of cancers. For example, the immune system identifies tumor cells as being foreign and thus are targeted for destruction by the immune system. Unfortunately, the response typically is not sufficient to prevent most tumor growths. However, recently there has been a focus in the area of immunotherapy to develop methods that augment or supplement the natural defense mechanism of the immune system. Examples of immunotherapies currently under investigation or in use are immune adjuvants (e.g., *Mycobacterium bovis*, *Plasmodium falciparum*, dinitrochlorobenzene and aromatic compounds) (U.S. Pat. No. 5,801,005; U.S. Pat. No. 5,739,169; Hui and Hashimoto, 1998; Christodoulides et al., 1998); cytokine therapy (e.g., interferons α, β and γ; IL-1, GM-CSF and TNF) (Bukowski et al., 1998; Davidson et al., 1998; Hellstrand et al., 1998); gene therapy (e.g., TNF, IL-1, IL-2, p53) (Qin et al., 1998; Austin-Edward and Villaseca, 1998; U.S. Pat. No. 5,830,880 and U.S. Pat. No. 5,846,945); and monoclonal antibodies (e.g., anti-ganglioside GM2, anti-HER-2, anti-p 185) (Pietras et al., 1998; Hanibuchi et al., 1998; U.S. Pat. No. 5,824,311).

As mentioned above, proto-oncogenes play an important role in cancer biology. For example, Rb, p53, NF1 and WT1 tumor suppressors are essential for the maintenance of the non-tumorogenic phenotype of cells (reviewed by Soddu and Sacchi, 1998). Approximately 50% of all cancers have been found to be associated with mutations of the p53 gene, which result in the loss of p53 tumor suppressor properties (Levine et al., 1991; Vogelstein and Kinzler, 1992; Hartmann et al., 1996a; Hartmann et al., 1996b). Mutations in the p53 gene also result in the prolongation of the p53 half-life in cells and the overexpression of p53 protein. In normal cells, p53 is undetectable due to its high turnover rate. Thus, p53 overexpression in cancerous cells results in multiple immunogenic p53 epitopes that can be used in immunotherapy. The high incidence of cancer related to mutations of the p53 gene has prompted many research groups to investigate p53 as a route of cancer treatment via gene replacement. The proto-oncogenes sis, erbB, src, ras and myc, encoding proteins that induce cellular proliferation, and the proto-oncogenes of the Bcl-2 family that regulate programmed cell death also play important roles in the non-tumorogenic phenotype of cells.

A few also have explored the use of p53 in immunotherapy. For example, in an in vitro assay, p53 mutant peptides capable of binding to HLA-A2.1 and inducing primary cytotoxic T lymphocyte (CTL) responses were identified (Houbiers et al., 1993). In a study in which synthetic p53 mutant and wild-type peptides were screened for immunogenicity in mice, it was observed that only mutant p53 epitopes were capable of eliciting a CTL response (Bertholet et al., 1997). In contrast, the immunization of BALB/c mice with bone marrow-derived dendritic cells (DC) in the presence of GM-CSF/IL-4 and prepulsed with the H-2Kd binding wild-type p53 peptide (232-240) was observed to induce p53 anti-peptide CTL response (Ciemik et al., 1996; Gabrilovich et al., 1996; Yanuck et al., 1993; DeLeo, 1998; Mayordomo et al., 1996). Further, the intradermal and intramuscular injection of naked plasmid DNA encoding human wild-type p53 and the intravenous injection of human wild-type p53 presented by a recombinant canarypox vector have been successful in the destruction of tumors (Hurpin et al., 1998).

Pre-clinical studies using mouse models (Ishida et al., 1999; Murakami et al., 2004; Espenschied et al., 2003; Blaszczyk-Thurin et al., 2002; Cicinnati et al., 2005) and an ex vivo human culture model (Nikitin et al., 2001) have demonstrated that the induction of an anti-p53 CTL cell response has selectively killed tumor cells and spare normal cells. Furthermore, anti-p53 T cells have been shown to be present in cancer patients (Hoffmann et al., 2005; Sirianni et al., 2004; van der Burg et al., 2003).

Another critical element of cancer vaccines is a selection of adequate carrier for TAA. This vehicle should help to activate the primary immune response and if necessary to overcome tolerance to self-proteins. Dendritic cells (DC) are most potent antigen presenting cells and are actively used in cancer immunotherapy (reviewed in Gabrilovich, 2002). In recent years it became increasingly clear that success of DC-based immunotherapy depends of activation status of these cells. Adenovirus provides one exemplary effective means to activate DCs. It induced up-regulation of MHC class II and co-stimulatory molecules on DC surface, production of IL-12, Th1, and pro-inflammatory cytokines (Nikitina et al., 2002; Tan et al., 2005; Herrera et al., 2002). Adenovirus also provides excellent tool for gene delivery into DCs (reviewed in Humrich and Jenne, 2003; Gamvrellis et al., 2004).

WO 00/54839 describes dendritic cells transduced with a wild-type self gene for the treatment of hyperproliferative disease.

Despite the foregoing, there currently exist no methods of self gene-based immunotherapy capable of utilizing wild-type self genes to generate an antitumor immune response specific for a variety of therapy-resistant cells overexpressing different mutant self proteins. This would permit the treatment of any cancerous or pre-cancerous cell associated with increased or altered expression of the self gene. Further, it would eliminate the need to identify the site of self gene mutation in each patient and generate customized self gene mutant peptides for immunotherapy. Thus, the need exists for an immunotherapy that is capable of attenuating or enhancing the natural immune systems CTL response against hyperproliferative cells with increased or altered expression of mutant self gene antigens.

SUMMARY OF THE INVENTION

It is clear that new therapeutic approaches are needed to improve the outcome of cancer, and vaccines may represent one of such approaches. Although some clinical trials performed in recent years demonstrated encouraging results, most of the trials showed very limited clinical response (Rosenberg et al., 2004). The results of these trials exposed major challenges to successful cancer immunotherapy. One of the most important of them is identification of suitable tumor associated antigen (TAA). An ideal TAA would not only be expressed in a significant proportion of cancer patients, but survival of tumor cells would depend on the presence of molecules comprising TAA. This would prevent tumor cells from escaping immune recognition by losing these molecules. The tumor suppressor gene, p53, has many features of an ideal TAA and is employed as merely an exemplary embodiment in the present invention.

Generally, the present invention concerns compositions and methods related to cancer vaccines, particularly for the treatment of cancers, including therapy-resistant cancers. There exists a need for an immunotherapy that is capable of augmenting the natural immune system's CTL response against therapy-resistant hyperproliferative cells expressing an altered self gene antigen. The present invention also provides a method of eliciting a cytotoxic T lymphocyte response directed against p53 antigens presented by hyperproliferative therapy-resistant cells. In one embodiment of the invention, there is provided a method for treating an individual with a therapy-resistant hyperproliferative disease and/or preventing an individual from having a therapy-resistant hyperproliferative disease. In particular aspects, an individual having at least one cancer cell resistant to a cancer treatment is treated with a dendritic cell comprising a self gene product, and in additional embodiments the treatment further comprises an additional therapy. The additional therapy may be of any suitable kind of cancer treatment, although in particular aspects the additional therapy is chemotherapy. In further specific embodiments, the chemotherapy upregulates expression of p53 and/or a death receptor, for example.

The treatment of a hyperproliferative disease in the present invention may comprise the steps of identifying an individual with a hyperproliferative disease, characterized by alteration or increased expression of a self gene product in at least some of the hyperproliferative cells in the individual. In alternative embodiments, however, an individual may have previously been identified with a hyperproliferative disease characterized by alteration or increased expression of a self gene product in at least some of the hyperproliferative cells in the individual. Following identification of a subject with a hyperproliferative disease, an expression construct comprising a self gene under the control of a promoter operable in eukaryotic dendritic cells is administered to the subject. In particular aspects, the self gene product is expressed by dendritic cells and presented to immune effector cells, thereby stimulating an anti-self gene product response. In alternative embodiments, the self gene product that may be altered or have increased expression in the individual is not identified directly or indirectly, yet the expression construct comprising a self gene under the control of a promoter operable in eukaryotic dendritic cells is administered to the subject, such as intradermally, for example. The selection of the self gene product in the alternative embodiment may comprise known statistically favorable susceptibilities of self gene products as in a population of individuals. For example, a self gene product that is known to be mutated frequently in individuals that have cancer or that are susceptible thereto may be employed in the invention. Individuals having a high risk for developing a particular cancer include those having particular altered genes and/or gene expression, for example for p53, BRCA1, BRCA2, APC, DPC4, NF-1, NF-2, p16, p27, or RB; having a preneoplastic condition; personal history of cancer; family history of cancer; unprotected exposure to strong sunlight; tobacco use; and so forth.

In one embodiment, the self-gene product comprises an oncogene, wherein the oncogene may be selected from the group consisting of tumor suppressors, tumor-associated genes, growth factors, growth-factor receptors, signal transducers, hormones, cell cycle regulators, nuclear factors, transcription factors and apoptic factors. In particular embodiments, the tumor suppressor is selected from the group consisting of mda-7, Rb, p53, p16, p19, p21, p73, DCC, APC, NF-1, NF-2, PTEN, FHIT, C-CAM, E-cadherin, MEN-I, MEN-II, ZAC1, VHL, FCC, MCC, PMS1, PMS2, MLH-1, MSH-2, DPC4, BRCA1, BRCA2 and WT-1. In preferred embodiments, the tumor suppressor is p53. In preferred embodiments, the growth-factor receptor is selected from the group consisting of FMS, ERBB/HER, ERBB-2/NEU/HER-2, ERBA, TGF-β receptor, PDGF receptor, MET, KIT and TRK. In preferred embodiments, the signal transducer is selected from the group consisting of SRC, AB1, RAS, AKT/PKB, RSK-1, RSK-2, RSK-3, RSK-B, PRAD, LCK and ATM. In preferred embodiments, the transcription factor or nuclear factor is selected from the group consisting of JUN, FOS, MYC, BRCA1, BRCA2, ERBA, ETS, EVI1, MYB, HMGI-C, HMGI/LIM, SKI, VHL, WT1, CEBP-β, NFKB, IKB, GL1 and REL. In preferred embodiments, the growth factor is selected from the group consisting of SIS, HST, INT-1/WT1 and INT-2. In preferred embodiments, the apoptic factor is selected from the group consisting of Bax, Bak, Bim, Bik, Bid, Bad, Bcl-2, Harakiri and ICE proteases. In preferred embodiments, the tumor-associated gene is selected from the group consisting of CEA, mucin, MAGE and GAGE.

The expression construct may be a viral vector, wherein the viral vector is an adenoviral vector, a retroviral vector, a vaccinia viral vector, an adeno-associated viral vector, a polyoma viral vector, an alphavirus vector, or a herpesviral vector. In particular embodiments, the viral vector is an adenoviral vector.

In certain embodiments, the adenoviral vector is replication-defective. In another embodiment, the replication defect is a deletion in the E1 region of the virus. In certain embodiments, the deletion maps to the E1B region of the virus. In other embodiments, the deletion encompasses the entire E1B region of the virus. In another embodiment, the deletion encompasses the entire E1 region of the virus.

In one embodiment of the present invention, the promoter operable in eukaryotic cells may be selected from the group consisting of CMV IE, dectin-1, dectin-2, human CD11c, F4/80, MHC class II, and other promoters, whether natural or synthetic that function in the target cells. In preferred embodiments, the promoter is CMV IE. In another embodiment the expression vector further comprises a polyadenylation signal.

It is contemplated, in one embodiment of the present invention, that the hyperproliferative disease is cancer, wherein the cancer may be selected from the group consisting of lung, head, neck, breast, pancreatic, prostate, renal, bone, testicular, cervical, gastrointestinal, lymphoma, brain, colon, skin and bladder. In other embodiments, the hyperproliferative disease is non-cancerous and may be selected from the group consisting of rheumatoid arthritis (RA), inflammatory bowel disease (IBD), osteoarthritis (OA), pre-neoplastic lesions in the lung, and psoriasis, for example.

In other embodiments, the subject treated for a hyperproliferative disease is a human. It is contemplated, in certain embodiments, administering to the subject at least a first cytokine selected from the group consisting GM-CSF, IL-4, C-KIT, Steel factor, TGF-β, TNF-α and FLT3 ligand. In yet another embodiment, a second cytokine, different from the first cytokine, is administered to the subject. In another embodiment, the cytokine is administered as a polynucleotide encoded by the expression construct. In other embodiments, the immune effector cells are CTLs.

Also contemplated in the present invention is intradermal administration of the expression construct by a single injection or multiple injections. In one embodiment, the injections are performed local to a hyperproliferative or tumor site. In another embodiment, the injections are performed regional to a hyperproliferative or tumor site. In still another embodiment, the injections are performed distal to a hyperproliferative or tumor site. It is further contemplated that the injections are performed at the same time, at different times or via continuous infusion.

In particular aspects, the present invention comprises a method for inducing a p53-directed immune response in a subject having therapy-resistant cancer comprising the steps of obtaining dendritic cells from a subject, infecting the dendritic cells with an adenoviral vector comprising a p53 gene under the control of a promoter operable in eukaryotic cells and administering the adenovirus-infected dendritic cells to the subject, whereby p53 expressed in the dendritic cells is presented to immune effector cells, thereby stimulating an anti-p53 response.

Therapy to which the subject may have resistant cancer may be of any kind, although in particular embodiments the therapy may comprise chemotherapy, radiation, or both. In some embodiments of the present invention, there is a method of conferring or restoring chemosensitivity to one or more drug and/or radiation-resistant hyperproliferative cells in a subject, wherein the hyperproliferative disease is characterized by alteration or increased expression of a self gene product, comprising providing to the subject a dendritic cell expressing the self gene product. In specific embodiments, the method further comprises administering to the subject a further drug- or radiation therapy. Providing the dendritic cell may comprise administering a dendritic cell transformed with an expression construct expressing the self gene product or it may encompass administering an expression construct expressing the self gene product to a dendritic cell in the subject. In specific embodiments, the hyperproliferative disease comprises metastatic cancer, including therapy-resistant metastatic cancer.

Thus, in particular embodiments of the invention, there is a method of providing to an individual with a therapy-resistant hyperproliferative disease an immunogenic composition comprising a dendritic cell having a self gene product, which is preferably expressed. In further embodiments, the individual is provided a cancer therapy in addition to the immunogenic composition, and in certain aspects the two therapies work in an additive manner or in a synergistic manner to treat the hyperproliferative disease, including hyperproliferative cells that are resistant to a cancer treatment. In additional embodiments, the dendritic cell expressing a self gene product is considered as comprising a vaccine.

In one embodiment of the present invention, there is a method of conferring or restoring sensitivity to one or more therapy-resistant hyperproliferative cells in a subject, wherein said hyperproliferative cells are characterized by alteration or increased expression of a self gene product, comprising providing to said subject a dendritic cell expressing said self gene product. In a specific embodiment, the therapy-resistant hyperproliferative cells are further defined as resistant to a drug, radiation, or both. In a further specific embodiment, the therapy-resistant hyperproliferative cells are further defined as resistant to an interferon, interleukin, antibody, inhibitor, mixture thereof, or combination thereof. In specific embodiments, the antibody is further defined as a monoclonal antibody, such as a monoclonal antibody against Her-2/neu, including Herceptin®. In particular aspects, the monoclonal antibody is further defined as a monoclonal antibody against VEGF, such as Avastin, for example. In additional specific embodiments, the inhibitor is further defined as a VEGF inhibitor.

The drug to which the cell is resistant may be any one or more drugs, although in particular aspects the drug comprises paclitaxel, topotecan, cisplatin, carboplatin, doxorubicin, or docetaxel, for example. The drug may be an alkylating agent, such as busulfan, cisplatin, or ifosfamide, for example. The drug may be an anthracycline, such as doxorubicin or epirubicin, for example. The drug may be an anti-metabolite, such a fluorouracil or methotrexate, for example. The drug may be a topoisomerase inhibitor, such as bleomycin, etoposide, or gemcitabine, for example. The drug may be a microtubule inhibitor, such as paclitaxel, docetaxel, or vinblastine, for example. The drug may be a monoclonal antibody, such as trastuzumab (Herceptin®), bevacizumab (Avastin®), imatinib mesylate (Gleevec®), gefitinib (Iressa®), erlotinib (Tarceva®), or cetuximab (Erbitux®), for example. The drug may be cyclophosphamide. The drug may be an alkylating agent. The drug may be a topoisomerase 1 inhibitor, such as irinotecan.

In some embodiments, methods of the present invention further comprise administering to a subject an additional therapy, such as one comprising a drug, a metal, radiation, surgery, gene therapy, immunotherapy, hormone therapy, or a combination thereof. In specific embodiments, the chemotherapy comprises a composition that upregulates expression of p53, Fas, a death receptor, or a combination thereof. In additional specific embodiments, the dendritic cell and the additional therapy are provided to the subject concomitantly or in succession. In particular, the dendritic cell may be provided to the subject prior to the further therapy, such as within about one to twelve months of providing the dendritic cell to the subject. In certain aspects, the dendritic cell and the additional therapy are provided more than once, such as in cycles. In other specific embodiments, the dendritic cell is provided to the subject subsequent to the additional therapy, such as within about one to two months of providing the further therapy to the subject.

In particular aspects of the invention, there is administration of a dendritic cell transformed with an expression construct, such as an adenoviral vector, expressing said self gene product, such as p53. The self gene product may be a tumor suppressor or a proto-oncogene product. It may also be a gene product that is upregulated in cancer cells. In particular aspects, the self gene product comprises survivin, Her2/neu, CEA, ras, TERT, NY-ESO, PSA, CEA, MART, MAGE1, MAGE 3, gp100, BAGE, GAGE, TRP-1, TRP-2, mda-7, sus1, or PMSA.

In specific embodiments, the hyperproliferative cells in the invention are therapy-resistant cancer cells, such as metastatic cancer cells, for example. In additional specific embodiments, the cancer cells are small cell lung cancer cells. The hyperproliferative cells may be cells from lung cancer, breast cancer, colon cancer, melanoma, liver cancer, brain cancer, prostate cancer, kidney cancer, sarcoma, pancreatic cancer, lymphoma, or leukemia, for example.

In particular, hyperproliferative cells that may be treated by methods and compositions of the invention include at least cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following nonlimiting histological types: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In specific aspects of the invention, patients with extensive stage small cell lung cancer were vaccinated with dendritic cells transduced with adenoviral vector comprising wild-type p53 gene. A p53-specific T-cell response to vaccination was observed in many of the patients. Antigen-specific immune response to vaccination correlated positively with a moderate increase in the titer of anti-adenovirus antibody and negatively with accumulation of immature myeloid cells. No association between antigen-specific response to vaccination and the presence and functional activity of DCs and T cells was found. Only one patient demonstrated objective clinical response to vaccination, whereas most of the patients had disease progression. However, these patients showed very high rate of objective clinical response to chemotherapy that was started immediately after vaccination. This clinical response closely correlated with antigen-specific immune response. In specific embodiments, the present invention concerns a new paradigm in cancer immunotherapy, wherein vaccination is particularly effective not as a single modality but in direct synergy with another cancer treatment, such as chemotherapy.

In additional embodiments of the invention, there is treatment and/or prevention of Li-Fraumeni syndrome, for example utilizing a dendritic cell comprising the p53 self gene. As ras is up-regulated in pancreatic and colorectal cancers, for example, in these and other cancers one could target ras by employing dendritic cells comprising a ras polynucleotide in these subjects.

Thus, in one embodiment of the present invention there is a method of conferring or restoring sensitivity to one or more therapy-resistant hyperproliferative cells in a subject, wherein said hyperproliferative cells are characterized by alteration or increased expression of a self gene product, comprising providing to said subject a dendritic cell expressing said self gene product. In a specific embodiment, the therapy-resistant hyperproliferative cells are further defined as resistant to a drug, radiation, or both.

In a specific embodiment, the therapy-resistant hyperproliferative cells are further defined as resistant to an interferon, interleukin, antibody, inhibitor, mixture thereof, or combination thereof. The antibody may be further defined as a monoclonal antibody, which may be further defined as a monoclonal antibody against Her-2/neu, such as trastuzumab (Herceptin®). The monoclonal antibody may be further defined as a monoclonal antibody against VEGF, which may be further defined as bevacizumab (Avastin®). The inhibitor may be further defined as a VEGF inhibitor. The drug may comprise paclitaxel, topotecan, cisplatin, carboplatin, doxorubicin, cyclophosphamide, or docetaxel, for example. The drug may be an alkylating agent, such as busulfan, cisplatin, or ifosfamide. The drug may be an anthracycline, such as doxorubicin or epirubicin. The drug may be an anti-metabolite, such as fluorouracil or methotrexate. The drug may be a topoisomerase inhibitor, such as bleomycin, etoposide, or gemcitabine. The drug may be a microtubule inhibitor, such as paclitaxel or vinblastine. The drug may be a monoclonal antibody, such as trastuzumab, bevacizumab, imatinib mesylate, gefitinib, or erlotinib.

In certain aspects, methods of the invention further comprising administering to the subject an additional therapy, such as a drug, a metal, radiation, surgery, gene therapy, immunotherapy, hormone therapy, or a combination thereof. In specific embodiments, the additional therapy comprises chemotherapy, such as comprising a composition that upregulates expression of p53, Fas, a death receptor, or a combination thereof. In another specific embodiment, the dendritic cell and the additional therapy are provided to the subject concomitantly or in succession. In an additional specific embodiment, the dendritic cell is provided to the subject prior to the further therapy. The additional therapy may be provided to the subject within about one to twelve months of providing the dendritic cell to the subject, and the dendritic cell and the additional therapy may be provided more than once. In specific aspects, the dendritic cell and the additional therapy are provided in cycles. The dendritic cell may be provided to the subject subsequent to the additional therapy. The dendritic cell may be provided to the subject within about one to two months of providing the further therapy to the subject. The providing may comprise administering a dendritic cell transformed with an expression construct expressing said self gene product, for example, wherein providing comprises administering an expression construct expressing the self gene product to a dendritic cell in the subject.

In particular aspects of the invention, the expression construct comprises an adenoviral vector. The self gene product comprises p53, in certain aspects. The self gene product may comprise a tumor suppressor or a proto-oncogene product. The self gene product may be further defined as a gene product that is upregulated in cancer cells. In specific aspects, the self gene product comprises survivin, Her2/neu, CEA, ras, TERT, NY-ESO, PSA, CEA, MART, MAGE1, MAGE 3, gp100, BAGE, GAGE, TRP-1, TRP-2, or PMSA.

Hyperproliferative cells of the present invention are cancer cells, in certain embodiments, including metastatic cancer cells, in some embodiments. The hyperproliferative cells may be small cell lung cancer cells or they may be cells from lung cancer, breast cancer, colon cancer, melanoma, liver cancer, brain cancer, prostate cancer, kidney cancer, sarcoma, pancreatic cancer, lymphoma, or leukemia.

Methods of the invention may further comprise delivering to the subject an agent that enhances the activity of the dendritic cell expressing the self gene product, such as, for example, an antibody, including a monoclonal antibody, for example a CD40 antibody. The dendritic cell expressing the self gene product and the agent may be comprised in the same composition or they may be comprised in separate compositions. The dendritic cell expressing the self gene product and the agent are delivered to the subject at the same time, in certain embodiments, although the dendritic cell expressing the self gene product may be delivered to the subject prior to delivery of the agent to the subject, in alternative embodiments. In specific aspects, the dendritic cell expressing the self gene product is delivered to the subject subsequent to delivery of the agent to the subject. The subject has previously been treated with chemotherapy, radiation, or both, in specific embodiments of the invention.

Methods of the invention may further comprise the step of assaying a sample from the subject for the hyperproliferative cells, and the sample may comprise a biopsy, blood, urine, cheek scrapings, saliva, cerebrospinal fluid, feces, nipple aspirate, or a combination thereof. The assaying of the sample may include assaying for a therapy-resistance marker, such as a mutation in one or more polynucleotides in one or more of the hyperproliferative cells or an upregulation or downregulation of expression of one or more polynucleotides, compared to normal non-cancerous cells of the same tissue, for example.

In a further embodiment of the invention, there is a method of treating one or more hyperproliferative cells in a subject, wherein said one or more hyperproliferative cells are resistant to a clinically-recognized therapy for the hyperproliferative cells or wherein said one or more hyperproliferative cells will become resistant upon exposure to the clinically-recognized therapy for the hyperproliferative cells, and wherein the hyperproliferative cells are characterized by alteration or increased expression of a self gene product, comprising providing to said subject a dendritic cell expressing said self gene product. In certain aspects, the hyperproliferative cells that will become resistant upon exposure to the clinically-recognized therapy comprise a polynucleotide having one or more mutations associated with the resistance. The method may further comprise delivering to the subject an agent that enhances the activity of the dendritic cell expressing the self gene product.

Moreover, the present invention can be used to prevent therapy-resistant cancer. The development of therapy-resistant cancer from cancer that is sensitive to therapy may be halted, disrupted, or delayed by methods of the invention. Thus, in one embodiment there is a method of treating or preventing the development of therapy-resistant hyperproliferative cells, wherein said hyperproliferative cells are characterized by alteration or increased expression of a self gene product, comprising providing to said subject a dendritic cell expressing said self gene product.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 6 provides a chart of response to second line chemotherapy.

FIG. 7 shows drug activity in resistant SCLC compared to that of the present invention.

FIGS. 11A-11C show an example of p53-specific immune response to immunization. In FIG. 11A, two HLA-A2 negative patients were vaccinated with DC-Adv-p53 (3 vaccines with 2-week interval). Blood was collected before immunization, 3 weeks after last vaccine and 2 months later. Cells were stimulated with ALVAC-p53 as described in Material and Methods. ALVAC with "empty" vector was used as control (ALVAC-cont). The number of IFN-γ produced cells was evaluated in quadruplicates in ELISPOT and calculated per $2 \times 10^5$ mononuclear cells. Average±SD are shown. *—p<0.05 between cells incubated with ALVAC-p53 and ALVAC-cont. #—p<0.05 between pre- and post-vaccine samples. FIG. 11B shows that a HLA-A2 positive patient with extensive stage SCLC was vaccinated with DC-Adv-p53. Blood was collected before immunization and at different points after immunization. The number of IFN-γ produced cells per $2 \times 10^5$ mononuclear cells was evaluated in quadruplicates in ELISPOT. Cells were stimulated with HLA-A2 matched p53-derived peptide (LLGRNSFEV; SEQ ID NO:3), PSA-derived irrelevant peptide (FLTPKKLQCV; SEQ ID NO:2) or left in medium alone (control) Average±SD are shown. *—p<0.05 between cells incubated with p53 and PSA peptide, #—p<0.05 between pre- and post-vaccine samples. FIG. 11C shows that samples of peripheral blood from HLA-A2 positive patient were collected before and after immunization. Mononuclear cells were stained with APC conjugated anti-CD8 antibody and PE conjugated p53 tetramer. All CD8+ were gated and the proportion of tetramer positive cells within the population of CD8+ cells was evaluated.

In FIG. 13A, the titer of anti-adenovirus IgG was calculated using serial dilution assay. Patients were split in three groups: patient with no increase in antibody titer after vaccination (11 patients), patients with moderate increase in antibody titer (from 2 to 8 fold—10 patients) and patients with high increase in the titer after vaccination (>8 fold—12 patients). The proportion of patients who demonstrated cellular p53-specific immune response was calculated in each group. P value (two-tailed) was calculated using Mann Whitney test. In FIG. 13B, functional activity of T cells prior vaccination. Samples were collected prior vaccination. MNC were stimulated in triplicates with 0.1 µg TT (TT-response) or 5 µg/ml PHA (PHA response). Stimulation index was calculated as the ratio between cell proliferation in the presence of stimuli and the medium alone. Horizontal bar represent minimal values in control group (n=6). Individual results are shown. In FIG. 13C, patients were split into two groups: with normal level of T-cell response to stimulus and decreased level of the response (below minimal control values). Proportion of patients with positive p53-specific response was calculated within each group. No statistical differences were found between the groups (For both stimuli p values in Fisher's Exact Test were more than 0.4). In FIG. 13D, MNC collected prior and 2-3 weeks after vaccination were stained with PerCP-conjugated anti-CD3 antibody, PE-conjugated anti-CD4 antibody and FITC-conjugated anti-CD25 antibody and analyzed by flow cytometry. The proportion of CD25 high cells within the population of CD3+CD4+ T cells was calculated. Horizontal bar represent mean of the values in the groups (p values was >0.2 in Munn Whitney test). In FIG. 13E, patients were split into two groups: with control and increased levels of CD4+CD25+ T cells (above maximal control values). Proportion of patients with positive p53-specific response was calculated within each group. No statistical differences were found between the groups (p values in Fisher's Exact Test were more than 0.3).

In FIG. 14D, mean fluorescence intensity (MFI) of HLA-DR in Lin-cells. In FIG. 14E, MNC were used as stimulators of allogeneic control T cells as described herein. Results of 1:1 ratio (MNC:T cells) are shown. Each experiment was performed in triplicates. Two-tailed p values were calculated using Munn Whitney test. FIGS. 14C and 14F show percentage of patients with positive p53-specific response to vaccination (p53-responders) and negative response (p53 non-responders) was calculated within the groups of patients with control and decreased level of DC phenotype prior vaccination. Differences between groups were not statistically significant (two-tailed p value in Fisher's exact test was more 0.3). FIG. 14H shows percentage of p53-responders and non-responders was calculated within the groups of patients with control and elevated levels of ImC prior to vaccine administration. Two-tailed p value in Fisher's exact test is shown. FIG. 14I shows where mononuclear cells collected prior to and 2 to 3 weeks after vaccination were stained with a phycoerythrin-conjugated anti-CD3 antibody, an antigen-presenting cell-conjugated anti-CD4 antibody and a FITC-conjugated anti-CD25 antibody, and analyzed by flow cytometry. The proportion of $CD25^{high}$ cells within the population of $CD3^+CD4^+$ T cells was calculated. Bar, mean of the values in the groups (P>0.2 in Mann-Whitney test). In FIG. 14J, patients were divided into two groups: with control and increased levels of $CD4^+CD25^+$ T cells (above maximal control values). The proportion of patients with positive p53-specific responses was calculted within each group. No statistical differences were found between the groups (P>0.3 in Fisher's exact test). In FIG. 14K, mononuclear cells were isolated from control donors and patients with SCLC prior to vaccination. Cells were stained with a cocktail of antibodies and analyzed using multicolor flow cytometry. The proportion of immature myeloid cells ($Lin^-HLA-DR^-CD33^+$) was evaluated.

FIG. 15A shows survival of platinum resistant patients. Survival from the time of the first vaccine administration of the 13 platinum resistant patients who received chemotherapy after the vaccines. Median survival is 9.3 months. FIG. 15B shows survival of all patients. Survival of all 23 patients treated with the vaccine from the time of the first vaccine administered. The median survival is 10 months. FIG. 15C shows relationship between p53 specific immune response to vaccination and clinical response to chemotherapy. Eighteen patients who progressed after vaccination and were treated with second-line chemotherapy were split into two groups according to their immunological response to the vaccine. PD-progressive disease, SD-stable disease, PR-partial response, CR-complete response (all according to RESIST criteria). P was calculated using Wilcoxon sum rank test. FIG. 15D shows survival according to immune response. Survival from the first vaccine administration of the 22 patients who were evaluable for an anti-p53 immune response. The solid line represents patients who had a positive immune response (median survival, 12.1 months), and the dashed line represents those patients who did not (median survival, 7.9 months). The difference between the two survival curves has a p-value of 0.075.

FIGS. 17A-17B concern association between immunologic and clinical response to vaccination. In FIG. 17A, there are the results of IFN-γ ELISPOT assay from patients who developed p53 immune response to vaccination. The background level of nonspecific IFN-γ production (irrelevant peptide) was subtracted. The number of spots per $1\times10^5$ cells are shown. All measurements were done in quadruplicate. The mean for each sample is shown. In FIG. 17B, there are lymphocyte counts ($\times10^9$/L) in patients who were treated with second-line chemotherapy. Columns, mean; bars, ±SD.

DETAILED DESCRIPTION OF THE INVENTION

Figure 1:
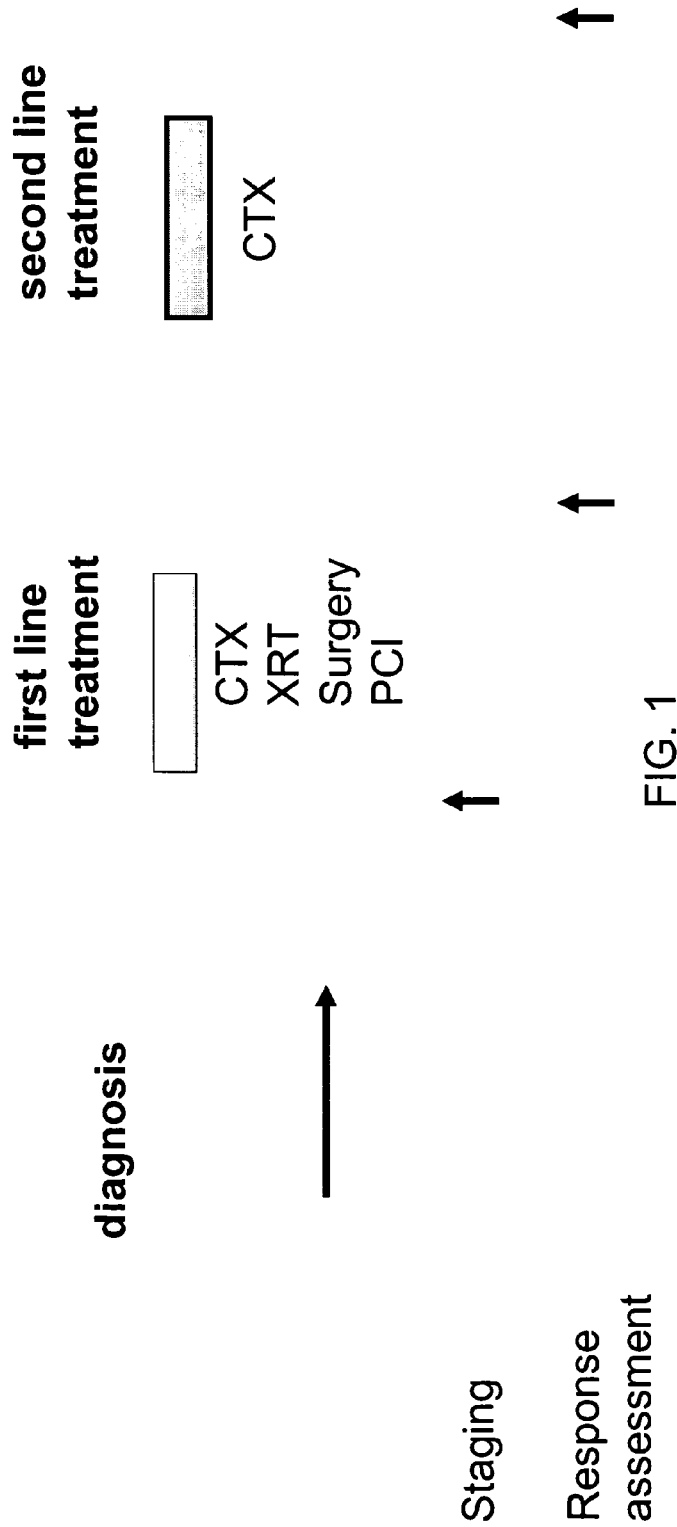
FIG. 1 provides an exemplary conventional SCLC treatment schema.

The present invention is related in subject matter to U.S. Patent Application Publication No. 20030045499, which is incorporated by reference herein in its entirety.

I. DEFINITIONS

As used herein the specification, "a" or "an" may mean one or more. As used herein in the claim(s), when used in conjunction with the word "comprising", the words "a" or "an" may mean one or more than one. As used herein "another" may mean at least a second or more. Some embodiments of the invention may consist of or consist essentially of one or more elements, method steps, and/or methods of the invention. It is contemplated that any method or composition described herein can be implemented with respect to any other method or composition described herein.

The term "conferring or restoring chemosensitivity" as used herein refers to rendering a cancer cell responsive to cancer treatment wherein the cancer cell is presently not responsive to a cancer treatment, is predicted to be nonresponsive to a cancer treatment, or is susceptible to being nonresponsive to a cancer treatment, for example. More specifically, the proliferation of a cancer cell that is not affected by a particular cancer treatment becomes affected by a cancer treatment. The cancer cell may have come from a cancer, such as in a tumor, for example, that had been previously sensitive to a cancer treatment, or the cancer cell may have come from a cancer, such as in a tumor, for example, that was never sensitive to a cancer treatment. The cancer cell may be susceptible to becoming resistant to one or more cancer treatments, and the method of the invention prevents the cell from becoming resistant to one or more cancer treatments. In certain embodiments, the cancer cell is susceptible to becoming resistant to treatment because it comprises a mutation in one or more polynucleotides associated with resistance and/or it comprises upregulation or downregulation of one or more polynucleotides, wherein the upregulation or downregulation is associated with resistance.

The term "first line therapy" as used herein refers to a first treatment a person receives after being diagnosed with cancer.

The term "immunogenic composition" as used herein refers to a composition that elicits an immune response in the body of an individual. In specific embodiments, the immunogenic composition comprises a vaccine, which may be defined as an immunogenic composition that provides immunity upon subsequent challenge.

The terms "resistant" or "therapy-resistant" as used herein refers to cancer comprising one or more cancer cells that are not able to be treated by one or more cancer treatments. For example, the cancer cell or cancer cells may still be able to proliferate following subjecting the cell to the treatment. In a specific embodiment, the cancer treatment that one or more cells are resistant to is chemotherapy. In other aspects, the resistance may be to one or more cancer therapies. In further specific embodiments, the resistant cells develop resistance to the therapy, whereas in alternative embodiments the resistant cells were always resistant to the therapy or comprised a biological or physiological phenotype or genotype rendering it unable to be sensitive to one or more cancer treatments.

In some embodiments an individual is treatable with the methods of the invention wherein the individual has previously been treated with a cancer treatment, such as chemotherapy, radiation, or both for example, although in other embodiments the individual has not been previously treated with a cancer treatment. In aspects wherein the individual has not been previously treated with a cancer treatment, the individual may comprise one or more cancer cells that will become resistant upon exposure to the cancer treatment. The manifestation of this resistance may occur immediately or soon after initiation of the cancer treatment to which the cells will become resistant, or the resistance may not manifest until months or years following initation of the treatment. The one or more cancer cells that are resistant or will become resistant to the therapy may or may not be metastatic.

The therapy to which the individual has one or more resistant cells is in the context of treatment routinely given for a particular cancer. That is, the therapy to which the individual is resistant may be qualified in terms of a traditional cancer treatment for that particular cancer, and in certain aspects the invention may relate to resistance to a clinically-recognized therapy for a particular cancer. For example, skilled artisans recognize that for breast cancer, traditional, clinically-recognized therapy includes at least Herceptin®; aromatase inhibitors (Arimidex® [chemical name: anastrozole], Aromasin® [chemical name: exemestane], and Femara® [chemical name: letrozole]); tamoxifen, raloxifene, toremifene, or Faslodex® (chemical name: fulvestrant). Exemplary clinically-recognized therapy for lung cancer includes at least cisplatin, etoposide, carboplatin, paclitaxel, docetaxel, vinorelbine tartrate, doxorubicin, vincristine sulfate, ifosfamide, and/or gemcitabine hydrochloride. Exemplary clinically-recognized therapy for prostate cancer includes at least docetaxel; luteinizing hormone-releasing hormone agonists, such as leuprolide, goserelin, and buserelin; antiandrogens, such as flutamide and bicalutamide; ketoconazole; and/or aminoglutethimide. One of skill in the art recognizes other conventional, clinically recognized treatments for other cancer types.

The term "second line therapy" as used herein refers to a therapy additional and subsequent to a first line therapy and in particular aspects is non-identical to the first line therapy. In cases where a human tumor responds (i.e., complete or partial response) to a first line therapy, the tumor is termed "sensitive" and, if the tumor recurs, second line treatment may involve re-administration of the same first line active therapy. However, SCLC, for example, is an especially aggressive cancer and has a very high frequency of tumor recurrence. In cases where tumors are treated with first line chemotherapy and the tumor either fails to respond (i.e., does not regress) or continues to grow, these tumors are considered "resistant" if tumor growth occurs within 90 days of completion of a chemotherapy regimen. As described above, for resistant tumors, a different chemotherapy is used for subsequent treatment, in specific embodiments.

The term "sensitive" as used herein refers to cancer comprising one or more cancer cells that is able to be treated with a particular cancer treatment. For example, the cell or cells are not able to proliferate following subjecting the cell to the treatment. In specific embodiments, a cell that is sensitive to a particular cancer treatment is killed by the treatment.

II. THE PRESENT INVENTION

The present invention contemplates the treatment of therapy-resistant hyperproliferative disease. In particular aspects, the treatment is by conferring or restoring chemosensitivity to an individual with cancer, wherein one or more of the cancer cells is resistant to therapy, by administering a self gene product expression construct in dendritic cells, which subsequently present the processed self gene product antigen to immune effector cells. In specific embodiments, the self gene product expression construct comprises a p53 expression construct. The immune effector cells then mount an anti-self gene product response, such as an anti-p53 response, resulting in the destruction or lysis of hyperproliferative cells presenting mutant self gene product antigen, including therapy-resistant hyperproliferative cells, such as exemplary mutant p53 antigen. In particular embodiments, dendritic cells are obtained from a patient in which expression of the self gene product, such as p53, is upregulated in hyperproliferative cells. The dendritic cells obtained are infected with an adenoviral vector comprising a p53 gene and the p53 adenovirus-infected dendritic cells are administered to the individual. It is contemplated that infected dendritic cells will present self gene antigens to immune effector cells, stimulate an anti-self gene response in the patient, and result in the destruction or lysis of hyperproliferative cells presenting mutant self gene antigen, including at least some that are resistant to cancer therapy. In specific embodiments, the hyperproliferative disease and/or its resistance to a cancer therapy is characterized by alteration or increased expression of a self gene product.

In further embodiments, the present invention encompasses sensitizing one or more cells of a hyperproliferative disease, and in particular embodiments, the disease and diseased cells thereof are resistant to a drug, radiation, or both, for example. The disease may be generally characterized by an alteration and/or increased expression of a self gene product and/or the resistance of the disease to one or more particular therapies may be generally characterized by an alteration and/or increased expression of a self gene product. In particular embodiments, the subject with the disease is provided a dendritic cell expressing the self gene product in addition to administering to the subject a further treatment for the hyperproliferative disease, such as a drug or radiation therapy, for example.

In additional embodiments, there is a method of conferring or restoring chemosensitivity to one or more chemotherapy-resistant cancer cells in an individual, comprising delivering to the individual a therapeutically effective amount of a dendritic cell expressing a self gene product and an additional treatment for the cancer. In a certain aspect of the invention, the composition comprises p53 in an adenoviral vector housed in a dendritic cell.

The dendritic cell expressing a self gene product may be considered an immunogenic composition, and in particular embodiments, the invention comprises methods of providing the dendritic cell expressing a self gene product and of providing another cancer therapy nonidentical to the dendritic cell expressing the self gene product, although dendritic cells expressing other self gene products may be employed. The therapy that is not the dendritic cell expressing a self gene product may comprise any type of cancer therapy, including, for example, chemotherapy, radiation, gene therapy, surgery, immunotherapy, hormone therapy, and the like. The two separate therapies may be administered to an individual in any suitabable regimen, although in specific embodiments the immunogenic composition is delivered subsequent to the other therapy. Part or all of the dendritic cell therapy and second therapy may be repeated, such as by cycling of the therapies.

Thus, in particular embodiments of the invention, there is a method of providing to an individual with a therapy-resistant hyperproliferative disease an immunogenic composition comprising a dendritic cell having a self gene product. In further embodiments, the individual is provided a cancer therapy in addition to the immunogenic composition, and in certain aspects the two therapies work in an additive manner or in a synergistic manner to treat the hyperproliferative disease, including hyperproliferative cells that are resistant to a cancer treatment. In additional embodiments, the dendritic cell expressing a self gene product is considered a vaccine.

III. ADVEXIN®-DENDRITIC CELL (DC)

Although any suitable composition comprising a dendritic cell expressing a self gene product may be employed in the invention, in specific aspects of the invention an Advexin®-DC composition is utilized. As used herein, an Advexin®-DC composition comprises wild-type p53 on a vector, wherein the vector is comprised in a dendritic cell. In particular aspects of the invention, the vector may be any suitable vector such that it permits expression of p53 within the dendritic cell. Exemplary embodiments of vectors include adenoviral vectors, viral vectors, adeno-associated viral vectors, retroviral vectors, such as lentiviral vectors, herpes viral vectors, or vaccinia viral vectors.

Although wild-type p53 is easily obtained by one of skill in the art, an exemplary wild-type sequence is provided in SEQ ID NO:1 (National Center for Biotechnology Information GenBank Accession No. M14695). Other p53 sequences are available in the National Center for Biotechnology's GenBank database.

In other embodiments, a composition is employed pursuant to those described in U.S. Pat. No. 6,726,907, which is incorporated by reference herein in its entirety, which includes a purified adenoviral vector composition comprising p53, for example.

IV. ENHANCEMENT OF METHODS AND COMPOSITIONS

In some embodiments of the invention, a dendritic cell expressing a self gene product further comprises one or more moieties to enhance the activity of the dendritic cell composition. The moiety may be added to the dendritic cell before or after the dendritic cell was manipulated to comprise the self gene product. In particular aspects of the invention, a dendritic cell was subjected to a composition to enhance its activity.

Any composition that enhances the activity of a dendritic cell expressing a self gene product may be employed in the invention, although in particular aspects the moiety comprises an antibody, and in specific embodiments the antibody is an monoclonal antibody, although optionally the antibody is a polyclonal antibody. In particular embodiments, the dendritic cell is subjected to anti-CD40 antibody (Nikitina et al., 2002). Alternate methods for promoting differentiation and activation of DC include treatment with pathogen receptors and inflammatory signals (see, for example Munz C, Steinman R M, Fujii S. Dendritic cell maturation by innate lymphocytes: coordinated stimulation of innate and adaptive immunity. J Exp Med. 2005 Jul. 18; 202(2):203-7).

The delivery method for any composition that enhances the activity of a dendritic cell expressing a self gene product may be of any suitable kind. In some embodiments, for example, the enhancing composition is provided as a polynucleotide, a polypeptide, a peptide, a small molecule, and so forth, and the delivery method is appropriately suited. For example, a small molecule, polypeptide, and/or protein that enhances the activity of a dendritic cell expressing a self gene product may be delivered in a liposome to an individual in need thereof. Alternatively, a polynucleotide encoding the enhancing composition may be utilized. In certain aspects, a polynucleotide encoding the enhancing composition is the same or different as the polynucleotide that encodes the self gene product. In those embodiments wherein the same polynucleotide comprising a sequence that encodes a self gene product also comprises a sequence that encodes the enhancing composition, the two sequences may encode a fusion gene product or may encode two separate gene products. In further embodiments, the sequence that encodes a self gene product and the sequence that encodes the enhancing composition are regulated by different regulatory regions, although in alternative embodiments they are regulated by the same regulatory region. Any regulatory region, which in specific embodiments may be referred to as a promoter, may be a tissue-specific regulatory region, an inducible regulatory region, or a constitutive regulatory region, for example.

V. SUBJECTS FOR TREATMENT WITH METHODS OF THE INVENTION

Any individual may be treated with methods and compositions of the invention. In certain aspects of the invention, the methods and compositions concern cancer vaccines. In particular embodiments, an individual is administered a vaccine of the invention. An individual suited for the methods and compositions of the invention may have one or more risk factors for developing one or more types of cancer. A risk factor may be defined as anything that increases the chance of developing cancer, and in this case may be anything that increases the chance of developing therapy-resistant cancer. The risk of developing therapy-resistant cancer may manifest before, during, or after administration of the therapy to which resistance has occurred.

The following risk factors may apply in general to developing cancer or specifically to developing therapy-resistant cancer, and thus, in specific embodiments the individual has one or more risk factors for developing cancer, including therapy-resistant cancer. Although different cancers have different risk factors, some risk factors apply to more than one type of cancer, such as having a preneoplastic condition, a personal history of cancer, a family history of cancer, and/or having altered genes and/or gene expression, for example for p53. Some risk factors are specific to one or more types of cancer, such as having particular altered genes and/or gene expression, for example BRCA1 or BRCA2 for breast cancer; unprotected exposure to strong sunlight for skin cancer; tobacco use for cancers of the lungs, larynx, mouth, throat, esophagus, kidneys, bladder, colon, and several other organs; and so forth.

Risk factors for individuals developing therapy-resistant cancer may be of any kind, although in specific embodiments they comprise one or more mutations and/or expression alterations identified with a particular polynucleotide. Examples include EGFR mutation and resistance of non-small-cell lung cancer to gefitinib (Kobayashi et al., 2005); melanocyte master regulator MITF (microphthalmia-associated transcription factor) and resistance to skin cancer (Garraway et al., 2005); ZNRD1 expression changes in gastric cancer cells (Zhang et al., 2003), for example. The classic mechanism for conferring resistance to chemotherapies is via up-regulation of the P-glycoprotein family of genes, responsible for conferring the mdr (multi-drug resistance) phenotype (Clarke R, Leonessa F, Trock B. Multidrug resistance/P-glycoprotein and breast cancer: review and meta-analysis. Semin Oncol. 2005 December; 32(6 Suppl 7):S9-15.). Mutations associated with resistance to breast cancer include estrogen receptor mutations in tamoxifen-resistant breast cancer (Karnik et al., 1994); a mutation in 482 (R482) in human BreastCancer Resistance Protein (BCRP) associated with doxorubicin resistance (Allen et al., 2002);

An individual with one or more risk factors for developing therapy-resistant cancer may be administered the methods and compositions of the present invention at any time, including before developing therapy-resistant cancer, after developing therapy-resistant cancer, or both.

VI. HYPERPROLIFERATIVE DISEASE

Cancer has become one of the leading causes of death in the Western world, second only behind heart disease. Current estimates project that one person in three in the U.S. will develop cancer, and that one person in five will die from cancer. Cancers can be viewed from an immunologic perspective as altered self cells that have lost the normal growth-regulating mechanisms.

Oncogenes are polynucleotides that have the potential to cause a normal cell to become cancerous. There are currently three major categories of oncogenes reflecting their different activities. One category of oncogenes encode proteins that induce cellular proliferation. A second category of oncogenes, called tumor-suppressors genes or anti-oncogenes, function to inhibit excessive cellular proliferation. The third category of oncogenes either block or induce apoptosis by encoding proteins that regulate programmed cell death.

In one embodiment of the present invention, the treatment of hyperproliferative disease involves the administration of a self gene expression construct to dendritic cells, and in specific embodiments, the administration is intradermally. It is contemplated that the dendritic cells present the processed self gene wild-type antigens to immune effector cells, which mount an anti-self gene response, resulting in the destruction or lysis of hyperproliferative cells presenting mutant self antigen. The three major categories of oncogenes are discussed below and listed in Table 1.

In particular embodiments, the present invention may be employed in the treatment of any type of cancer, including, for example, lung, breast, prostate, colon, pancreatic, brain, skin, thyroid, liver, kidney, spleen, esophageal, ovarian, cervical, uterine, testicular, bone, pituitary gland, stomach, blood, bone marrow, and lymphatic system.

In specific embodiments, the present invention is utilized for the treatment of small cell lung cancer. Small cell lung cancer (SCLC) constitutes 15-20% of the approximately 170,000 new cases of lung cancer seen annually in the US. SCLC is the most aggressive form of lung cancer, with 5 year survival rates of <10%. Diagnosis of extensive stage disease (ES) comprises approximately two-thirds of new SCLC cases, and results in survival of only 2-4 months if untreated, and survival increases to 6-7 months with aggressive chemotherapy regimens. Both limited stage and extensive stage disease are very responsive to first line chemotherapy with response rates of greater than 50% routinely observed. However, these responses almost invariably are short-lived and disease recurrence in ES patients occurs frequently. After relapse or failure to respond to chemotherapy, patients generally succumb to disease within a few months (Schiller, 2001). Treatment of patients with relapsed SCLC is especially challenging: if patients are platinum-resistant (i.e., disease progression occurs within 3 months of completion of a platinum regimen), median survival ranges from 3.7 to 4.7 months. For platinum-sensitive patients, median survival ranges from 5.8-6.9 months (Eckardt, 2005).

A. Inducers of Cellular Proliferation

The proteins that induce cellular proliferation further fall into various categories dependent on function. The commonality of all of these proteins is their ability to regulate cellular proliferation. For example, a form of PDGF, the sis oncogene is a secreted growth factor. Oncogenes rarely arise from genes encoding growth factors, and at the present, sis is the only known naturally occurring oncogenic growth factor.

The proteins fms, erbA, erbB and neu are growth factor receptors. Mutations to these receptors result in loss of regulatable function. For example, a point mutation affecting the transmembrane domain of the nue receptor protein results in the nue oncogene. The erbA oncogene is derived from the intracellular receptor for thyroid hormone. The modified oncogenic erbA receptor is believed to compete with the endogenous thyroid hormone receptor, causing uncontrolled growth.

The largest class of oncogenes are the signal transducing proteins (e.g., src, abl and ras) are signal transducers. The protein src, is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins jun, fos and myc are proteins that directly exert their effects on nuclear functions as transcription factors. Table 1 lists a variety of the oncogenes described in this section and many of those not described.

B. Inhibitors of Cellular Proliferation

The tumor suppressor oncogenes function to inhibit excessive cellular proliferation. The inactivation of these genes results destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently-mutated gene in common human cancers. It is mutated in over 50% of human NSCLC (Hollstein et al., 1991) and in a wide spectrum of other tumors. A variety of cancers have been associated with mutations of the p53 gene, which result in the loss of p53 tumor suppressor properties. Mutations in the p53 gene further account for approximately 50% of all cancers that develop (Vogelstein and Kinzler, 1992; Levine et al., 1991), with the majority of these mutations being single-base missense mutations (Kovach et al., 1996). It has been observed that mutations resulting in a loss of p53 function also result in high nuclear and cytoplasmic concentrations (i.e., overexpression) of mutant p53 protein (Oldstone et al., 1992; Finlay et al., 1988). In contrast, functional wild-type p53 protein is expressed at very low levels in cells.

The high cellular concentrations of p53 mutant protein has recently received much attention as an avenue for cancer immunotherapy. The general concept is to elicit an immune response against tumor cells presenting mutant p53 peptides bound to MHC molecules on the cell surface. The generation of an anti-tumor response using mutant p53 peptides as antigens has been demonstrated in several studies (McCarty et al., 1998; Gabrilovich et al., 1996; Mayordomo et al., 1996; Zitvogel et al., 1996) However, this approach to cancer immunotherapy has several limitations. For example, p53 mutations can occur at many different sites in the protein, making it necessary to identify the site of the mutation in each patient before creating a specific mutant peptide for p53 cancer therapy. Further, not all mutations are contained in regions of the protein known to bind to MHC molecules, and therefore would not elicit an anti-tumor response (DeLeo, 1998).

The limitations described above have stimulated the search for antigenic epitopes in wild-type p53 sequences common to the vast majority of tumor derived p53 proteins. Wild-type p53 peptide-specific cytotoxic T lymphocytes have been produced from human and murine responding lymphocytes, some of which recognized p53-overexpressing tumors in vitro and in vivo (Theobald, et al., 1995; Ropke et al., 1996; Nijman et al., 1994; U.S. Pat. No. 5,747,469, specifically incorporated herein by reference in its entirety). However, since the presentation of antigens is MHC class I restricted, only certain peptides can successfully be administered in certain patients, due to the polymorphic nature of the MHC class I peptide binding site. Further, it is not practical to identify all possible p53 peptides binding to a particular individuals repertoire of MHC molecules. Additionally, a peptide vaccine that does bind to a patient's class I MHC may not be sufficiently presented by MHC class II, the molecules crucial in the induction of $CD4^+$ T cell immune responses.

Researchers have to attempted to identify multiple p53 epitopes, which should permit more effective immune responses against tumor cells expressing multiple p53 genes with mutations at different sites. This could be accomplished by immunizing cells with intact wild-type p53 to take advantage of the overexpression of the whole p53 polypeptide in most human tumors. The dendritic cell (DC) is the cell type best suited for vaccine antigen delivery (described further herein), as they are the most potent antigen presenting cells, effective in the stimulation of both primary and secondary immune responses (Steinman, 1991; Celluzzi and Falo, 1997). It is contemplated in the present invention that the transduction of dendritic cells with wild-type p53 protein, using a viral expression construct, will elicit a potent antitumor immune response specific for a variety of cells expressing different mutant p53 proteins. Further, since most mutations of p53 are single-base missense mutations, the approach of the present invention overcomes the limitations of identifying the site of the p53 mutation and subsequent preparation of a customized mutant peptide for immunotherapy. Thus, the method of the present invention provides the basis for a simple and novel approach to immunotherapy based cancer treatment.

Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $p16^B$, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type $p16^{INK4}$ function by transfection with a plasmid expression vector reduced colony formation by some human cancer cell lines (Okamoto, 1994; Arap, 1995).

C-CAM is expressed in virtually all epithelial cells (Odin and Obrink, 1987). C-CAM, with an apparent molecular weight of 105 kD, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly homologous to carcinoembryonic antigen (CEA) (Lin and Guidotti, 1989). Using a baculovirus expression system, Cheung et al. (1993) demonstrated that the first Ig domain of C-CAM is critical for cell adhesive activity.

Cell adhesion molecules, or CAM's are known to be involved in a complex network of molecular interactions that regulate organ development and cell differentiation (Edelman, 1985). Recent data indicate that aberrant expression of CAM's maybe involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, Giancotti and Ruoslahti (1990) demonstrated that increasing expression of $\alpha_5\beta_1$ integrin by gene transfer can reduce tumorigenicity of Chinese hamster ovary cells in vivo. C-CAM now has been shown to suppress tumors growth in vitro and in vivo.

Other tumor suppressors that may be employed according to the present invention include RB, APC, DCC, NF-1, NF-2, WT-1, MEN-I, MEN-II, zacl, p73, VHL, MMAC1, FCC and MCC (see Table 1).

C. Regulators of Programmed Cell Death

Apoptosis, or programmed cell death, is an essential occurring process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, Mcl-1, Al, Bfl-1) or counteract Bcl-2 function and promote cell death (e.g., Bax, Bak, Bik, Bim, Bid, Bad, Harakiri).

TABLE 1

| Gene | Source | Human Disease | Function |
|---|---|---|---|
| Growth Factors[1] | | | |
| HST/KS | Transfection | | FGF family member |
| INT-2 | MMTV promoter Insertion | | FGF family member |
| INT1/WNT1 | MMTV promoter Insertion | | Factor-like |
| SIS | Simian sarcoma virus | | PDGF B |
| Receptor Tyrosine Kinases[1,2] | | | |
| ERBB/HER | Avian erythroblastosis virus; ALV promoter insertion; amplified human tumors | Amplified, deleted squamous cell cancer; glioblastoma | EGF/TGF-α/ amphiregulin/ hetacellulin receptor |
| ERBB-2/NEU/HER-2 | Transfected from rat Glioblatoms | Amplified breast, ovarian, gastric cancers | Regulated by NDF/ heregulin and EGF-related factors |
| FMS | SM feline sarcoma virus | | CSF-1 receptor |
| KIT | HZ feline sarcoma virus | | MGF/Steel receptor hematopoieis |
| TRK | Transfection from human colon cancer | | NGF (nerve growth factor) receptor |
| MET | Transfection from human osteosarcoma | | Scatter factor/HGF receptor |
| RET | Translocations and point mutations | Sporadic thyroid cancer; familial medullary thyroid cancer; multiple endocrine neoplasias 2A and 2B | Orphan receptor Tyr kinase |
| ROS | URII avian sarcoma Virus | | Orphan receptor Tyr kinase |
| PDGF receptor | Translocation | Chronic myclomonocytic leukemia | TEL(ETS-like transcription factor)/PDGF receptor gene fusion |
| TGF-β receptor | | Colon carcinoma mismatch mutation target | |
| NONRECEPTOR TYROSINE KINASES[1] | | | |
| ABI. | Abelson Mul. V | Chronic myelogenous leukemia translocation with BCR | Interact with RB, RNA polymerase, CRK, CBL |
| FPS/FES | Avian Fujinami SV; GA FeSV | | |
| LCK | Mul. V (murine leukemia virus) promoter insertion | | Src family; T cell signaling; interacts CD4/CD8 T cells |
| SRC | Avian Rous sarcoma Virus | | Membrane-associated Tyr kinase with signaling function; activated by receptor kinases |
| YES | Avian Y73 virus | | Src family; signaling |
| SER/THR PROTEIN KINASES[1] | | | |
| AKT | AKT8 murine retrovirus | | Regulated by PI(3)K; regulate 70-kd S6k |

TABLE 1-continued

| Oncogenes | | | |
|---|---|---|---|
| Gene | Source | Human Disease | Function |
| MOS | Maloney murine SV | | GVBD; cystostatic factor; MAP kinase kinase |
| PIM-1 | Promoter insertion Mouse | | |
| RAF/MIL | 3611 murine SV; MH2 avian SV | | Signaling in RAS pathway |
| MISCELLANEOUS CELL SURFACE[1] | | | |
| APC | Tumor suppressor | Colon cancer | Interacts with catenins |
| DCC | Tumor suppressor | Colon cancer | CAM domains |
| E-cadherin | Candidate tumor Suppressor | Breast cancer | Extracellular homotypic binding; intracellular interacts with catenins |
| PTC/NBCCS | Tumor suppressor and *Drosophilia* homology | Nevoid basal cell cancer syndrome (Gorline syndrome) | 12 transmembrane domain; signals through Gli homogue CI to antagonize hedgehog pathway |
| TAN-1 Notch homologue | Translocation | T-ALI. | Signaling |
| MISCELLANEOUS SIGNALING[1,3] | | | |
| BCL-2 | Translocation | B-cell lymphoma | Apoptosis |
| CBL | Mu Cas NS-1 V | | Tyrosine-phosphorylated RING finger interact Abl |
| CRK | CT1010 ASV | | Adapted SH2/SH3 interact Abl |
| DPC4 | Tumor suppressor | Pancreatic cancer | TGF-β-related signaling pathway |
| MAS | Transfection and Tumorigenicity | | Possible angiotensin receptor |
| NCK | | | Adaptor SH2/SH3 |
| GUANINE NUCLEOTIDE EXCHANGERS AND BINDING PROTEINS[3,4] | | | |
| BCR | | Translocated with ABL in CML | Exchanger; protein kinase |
| DBL | Transfection | | Exchanger |
| GSP | | | |
| NF-1 | Hereditary tumor Suppressor | Tumor suppressor neurofibromatosis | RAS GAP |
| OST | Transfection | | Exchanger |
| Harvey-Kirsten, N-RAS | HaRat SV; Ki RaSV; Balb-MoMuSV; Transfection | Point mutations in many human tumors | Signal cascade |
| VAV | Transfection | | S112/S113; exchanger |
| NUCLEAR PROTEINS AND TRANSCRIPTION FACTORS[1,5-9] | | | |
| BRCA1 | Heritable suppressor | Mammary cancer/ovarian cancer | Localization unsettled |
| BRCA2 | Heritable suppressor | Mammary cancer | Function unknown |
| ERBA | Avian erythroblastosis Virus | | thyroid hormone receptor (transcription) |
| ETS | Avian E26 virus | | DNA binding |
| EVII | MuLV promotor Insertion | AML | Transcription factor |
| FOS | FBI/FBR murine osteosarcoma viruses | | 1 transcription factor with c-JUN |
| GLI | Amplified glioma | Glioma | Zinc finger; cubitus interruptus homologue is in hedgehog signaling pathway; inhibitory link PTC and hedgehog |

TABLE 1-continued

| Gene | Source | Human Disease | Function |
|---|---|---|---|
| Oncogenes | | | |
| HMGG/LIM | Translocation t(3:12) t(12:15) | Lipoma | Gene fusions high mobility group HMGI-C (XT-hook) and transcription factor LIM or acidic domain |
| JUN | ASV-17 | | Transcription factor AP-1 with FOS |
| MLL/VHRX + ELI/MEN | Translocation/fusion ELL with MLL Trithorax-like gene | Acute myeloid leukemia | Gene fusion of DNA-binding and methyl transferase MLL with ELI RNA pol II elongation factor |
| MYB | Avian myeloblastosis Virus | | DNA binding |
| MYC | Avian MC29; Translocation B-cell Lymphomas; promoter Insertion avian leukosis Virus | Burkitt's lymphoma | DNA binding with MAX partner; cyclin regulation; interact RB; regulate apoptosis |
| N-MYC L-MYC | Amplified | Neuroblastoma Lung cancer | |
| REL | Avian Retriculoendotheliosis Virus | | NF-κB family transcription factor |
| SKI | Avian SKV770 Retrovirus | | Transcription factor |
| VHL | Heritable suppressor | Von Hippel-Landau syndrome | Negative regulator or elongin; transcriptional elongation complex |
| WT-1 | | Wilm's tumor | Transcription factor |
| CELL CYCLE/DNA DAMAGE RESPONSE[10-21] | | | |
| ATM | Hereditary disorder | Ataxia-telangiectasia | Protein/lipid kinase homology; DNA damage response upstream in P53 pathway |
| BCL-2 | Translocation | Follicular lymphoma | Apoptosis |
| FACC | Point mutation | Fanconi's anemia group C (predisposition leukemia | |
| FHIT | Fragile site 3p14.2 | Lung carcinoma | Histidine triad-related diadenosine 5',3''''-$P^1.p^4$ tetraphosphate asymmetric hydrolase |
| hMLI/MutL | | HNPCC | Mismatch repair; MutL homologue |
| hMSH2/MutS | | HNPCC | Mismatch repair; MutS homologue |
| hPMS1 | | HNPCC | Mismatch repair; MutL homologue |
| hPMS2 | | HNPCC | Mismatch repair; MutL homologue |
| INK4/MTS1 | Adjacent INK-4B at 9anti-estrogen receptor tyrosine kinase inhibitor; CDK complexes | Candidate MTS1 suppressor and MLM melanoma gene | p16 CDK inhibitor |
| INK4B/MTS2 | | Candidate suppressor | p15 CDK inhibitor |

TABLE 1-continued

Oncogenes

| Gene | Source | Human Disease | Function |
| --- | --- | --- | --- |
| MDM-2 | Amplified | Sarcoma | Negative regulator p53 |
| p53 | Association with SV40 T antigen | Mutated >50% human tumors, including hereditary Li-Fraumeni syndrome | Transcription factor; checkpoint control; apoptosis |
| PRAD1/BCL1 | Translocation with Parathyroid hormone or IgG | Parathyroid adenoma; B-CLL | Cyclin D |
| RB | Hereditary Retinoblastoma; Association with many DNA virus tumor Antigens | Retinoblastoma; osteosarcoma; breast cancer; other sporadic cancers | Interact cyclin/cdk; regulate E2F transcription factor |
| XPA | | xeroderma pigmentosum; skin cancer predisposition | Excision repair; photo-product recognition; zinc finger |

VII. IMMUNOLOGIC RESPONSES RELATED TO SELF GENE TUMOROGENICITY

In one embodiment of the present invention, hyperproliferative disease in which expression of a self gene is upregulated in therapy-resistant hyperproliferative cells is treated by administering a self gene expression construct capable of eliciting an anti-self gene response. The self gene p53 will be referred to herein as merely an exemplary embodiment.

Following delivery of the p53 expression construct to a given antigen-presenting cell, a cascade of immunologic events must ensue to stimulate the desired anti-p53 response. Thus, a basic understanding of the immunologic responses related to p53 expression and more generally, self gene expression in hyperproliferative disease, is necessary.

A. Cytotoxic T Lymphocytes

T lymphocytes arise from hematopoietic stem cells in the bone marrow, and migrate to the thymus gland to mature. T cells express a unique antigen binding receptor on their membrane (T-cell receptor), which can only recognize antigen in association with major histocompatibility complex (MHC) molecules on the surface of other cells. There are at least two populations of T cells, known as T helper cells and T cytotoxic cells. T helper cells and T cytotoxic cells are primarily distinguished by their display of the membrane bound glycoproteins CD4 and CD8, respectively. T helper cells secret various lymphokines, that are crucial for the activation of B cells, T cytotoxic cells, macrophages and other cells of the immune system. In contrast, a T cytotoxic cells that recognizes an antigen-MHC complex proliferates and differentiates into an effector cell called a cytotoxic T lymphocyte (CTL). CTLs eliminate cells of the body displaying antigen, such as virus infected cells and tumor cells, by producing substances that result in cell lysis.

An important aspect of the present invention is the stimulation of a CTL response directed against wild-type self gene antigen. It has been observed that mutations of the p53 gene result in the overexpression of the mutant p53 protein in tumor cells (Harris, 1996), while wild-type p53 is expressed at low levels in normal cells. It has further been demonstrated that wild-type and mutant p53 peptides can stimulate a CTL response against tumor cells expressing p53 antigenic peptides (DeLeo, 1998; Mayordomo et al., 1996). It is contemplated in the present invention that a similar anti-self gene CTL response will be stimulated by immunizing dendritic cells with intact wild-type self gene polypeptide, and thus can be used as a treatment for hyperproliferative disease.

B. Antigen-Presenting Cells

Antigen-presenting cells, which include macrophages, B lymphocytes, and dendritic cells, are distinguished by their expression of a particular MHC molecule. APCs internalize antigen and re-express a part of that antigen, together with the MHC molecule on their outer cell membrane.

In a preferred embodiment of the present invention, dendritic cells are the antigen-presenting cells of choice for self gene delivery and antigen presentation. Dendritic cells are the most potent antigen-presenting cells for the initiation of antigen-specific T cell activation (Arthur et al., 1997). They are also excellent candidates for short term culture and a variety of gene transfer methods (e.g., DNA/liposome complexes, electroporation, CaPO4 precipitation, and recombinant adenovirus) (Arthur et al., 1997). Human and mouse dendritic cells have been successfully modified by adenoviral gene transfer (Sonderbye et al., 1998). In this study, an adenovirus (AdLacZ) was used to express intracellular beta-galactosidase (beta-gal) antigen in the dendritic cells, with approximately 40% of the cells transduced with AdLacZ expressing high levels of beta-gal. In addition, the subcutaneous immunization of mouse dendritic cells with the ovalbumin (OVA) peptide induced an OVA-specific CD8+CTL response (Celluzzi and Falo, 1997).

C. Major Histocompatibilty Complex

The major histocompatibility complex (MHC) is a large genetic complex with multiple loci. The MHC loci encode two major classes of MHC membrane molecules, referred to as class I and class II MHCs. T helper lymphocytes generally recognize antigen associated with MHC class II molecules, and T cytotoxic lymphocytes recognize antigen associated with MHC class I molecules. In humans the MHC is refereed to as the HLA complex and in mice the H-2 complex. An important aspect of the present invention is the immunization of dendritic cells with the intact wild-type self gene to take advantage of the relative overexpression of the whole self gene molecule in most human tumors. The approach of p53 immunotherapy is contemplated in one embodiment, to overcome previous immunotherapies that immunized animals with mutant p53 peptides as antigens (Gabrilovich et al., 1996; Mayordomo et al., 1996; Zitgovel et al., 1996).

Although the approaches above using mutant p53 peptides were effective at generating anti-tumor responses, they have several limitations. For example, p53 mutations and other self genes occur at many sites in the protein, making it necessary to identify the site of mutation in each patient before constructing a customized mutant peptide for therapy. Furthermore, not all mutations are contained in regions of the protein known to bind to MHC molecules. In another study using wild-type 53 peptides, CTLs were generated from human and murine responding lymphocytes, some of which recognized p53 overexpressing tumors in vitro (Theobald et al., 1995; Ropke et al., 1996; Nijman et al., 1994). However, since presentation of antigens is MHC class I restricted, only certain oligopeptides can be used in certain patients, because of the highly polymorphic MHC class I peptide binding site. It is contemplated in the present invention that immunizing dendritic cells with intact, wild-type self gene protein, will generate a variety of self gene antigens for MHC class I presentation and thus effectively stimulate a cytolytic T lymphocyte response.

VIII. ASSAYS FOR SELF GENE UPREGULATION OR ALTERED EXPRESSION

In one embodiment of the present invention, the identification of a patient with a therapy-resistant hyperproliferative disease in which self gene expression is upregulated is desired. In patients with a therapy-resistant hyperproliferative disease, a sample of the hyperproliferative tissue will be used to assay upregulation, for example. A wide variety of detection methods can be employed in the present invention to detect the self gene status of at least one therapy-resistant cell, in certain embodiments. There are numerous antibodies to the oncogenic proteins, for example, and hence any assay that utilizes antibodies for detection, for example, ELISAs, Western Blotting, immunoassay techniques, etc., are contemplated as useful in the present invention. Alternatively, assays that employ nucleotide probes may be used to identify the presence of self gene, for example, Southern blotting, Northern blotting or PCR™ techniques. All the above techniques are well known to one of skill in the art and could be utilized in the present invention without undue experimentation.

A. ELISAs, Immunoassay and Immunohistological Assay.

In a particular embodiment of the present invention, immunohistological assays are used to detect self gene increased or altered expression in therapy-resistant tumor samples (e.g., tissue sections). Exemplary methods of immunohistochemistry assays and immunfluorescence assays have previously been described (U.S. Pat. No. 5,858,723; WO94/11514, specifically incorporated herein by reference in its entirety). Further immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo. Immunoassays generally are binding assays. Certain preferred immunoassays are the various types of enzyme linked immunosorbent assays (ELISAs) and radioimmunoassays (RIA) known in the art.

In one exemplary ELISA, the anti-self gene antibodies are immobilized on a selected surface, such as a well in a polystyrene microtiter plate, dipstick or column support. Then, a test composition suspected of containing the desired antigen, such as a clinical sample, is added to the wells. After binding and washing to remove non-specifically bound immune complexes, the bound antigen may be detected. Detection is generally achieved by the addition of another antibody, specific for the desired antigen, that is linked to a detectable label. This type of ELISA is known as a "sandwich ELISA." Detection also may be achieved by the addition of a second antibody specific for the desired antigen, followed by the addition of a third antibody that has binding affinity for the second antibody, with the third antibody being linked to a detectable label.

B. Southern and Northern Blotting Techniques

Southern and Northern blotting are commonly used techniques in molecular biology and well within the grasp of one skilled in the art. Southern and Northern blotting samples are obtained from the hyperproliferative tissue. The DNA and RNA from test cells is recovered by gentle cell rupture in the presence of a cation chelator such as EDTA. The proteins and other cell milieu are removed by admixing with saturated phenol or phenol/chloroform and centrifugation of the emulsion. The DNA and RNA is in the upper aqueous phase, it is deproteinized and mixed with ethanol. This solution allows the DNA and RNA to precipitate, the DNA and RNA can then be recover using centrifugation. In the case of RNA extraction, RNAse inhibitors such as DEPC are needed to prevent RNA degradation.

Electrophoresis in agarose or polyacrylamide gels is the most usual way to separate DNA and RNA molecules. Southern blotting will confirm the identity of the self gene encoding DNA. This is achieved by transferring the DNA from the intact gel onto nitrocellulose paper. The nitrocellulose paper is then washed in buffer that has for example, a radiolabelled cDNA containing a sequence complementary to wild-type self gene DNA. The probe binds specifically to the DNA that encodes a region of self gene and can be detected using autoradiography by contacting the probed nitrocellulose paper with photographic film. Self gene-encoding mRNA can be detected in a similar manner by a process known as Northern blotting. For a more detailed description of buffers gel preparation, electrophoresis condition etc., the skilled artisan is referred to Sambrook, 1989.

C. Polymerase Chain Reaction (PCR™)

PCR™ is a powerful tool in modern analytical biology. Short oligonucleotide sequences usually 15-35 bp in length are designed, homologous to flanking regions either side of the self gene sequences to be amplified. The primers are added in excess to the source DNA, in the presence of buffer, enzyme, and free nucleotides. The source DNA is denatured at 95° C. and then cooled to 50-60° C. to allow the primers to anneal. The temperature is adjusted to the optimal temperature for the polymerase for an extension phase. This cycle is repeated 25-40 times.

In particular the present invention uses PCR™ to detect the self gene status of cells. Mutations in the self gene are first detected with Single Strand Conformation Polymorphism (SSCP) which is based on the electrophoretic determination of conformational changes in single stranded DNA molecules induced by point mutations or other forms of slight nucleotide changes. To identify where the mutation is located at within the self gene, each exon is separately amplified by PCR™ using primers specific for the particular exon. After amplification, the PCR™ product is denatured and separated out on a polyacrylamide gel to detect a shift in mobility due to a conformational change which resulted because of a point mutation or other small nucleotide change in the gene. Mutations result in a change in the physical conformation of the DNA as well as change in the electrical charge of the molecule. Thus during electrophoresis when an electrical charge is applied to the molecule, DNA that is slightly different in shape and charge as compared to wild-type will move at a different rate and thus occupy a different position in the gel.

After determination of which DNA fragment contains the mutation, the specific nucleotide changes are detected by DNA sequencing of the amplified PCR™ product. Sequencing of linear DNA breaks down the DNA molecule into its individual nucleotides in the order with which they are assembled in the intact molecule. Separation of the individual nucleotides by electrophoresis on a sequencing gel allows detection of individual nucleotide changes compared to wild-type and is used to determine homo- or heterozygocity of a mutation, which is easily distinguished by the appearance of a single or double band in the sequencing gel.

IX. SELF GENE DELIVERY

Many types of cancer have been associated with mutations in oncogenes. These mutations typically result in the overexpression of a mutant self gene protein in tumor cells. It has been further demonstrated that wild-type p53 peptide specific cytotoxic T lymphocytes were generated from human and murine responding lymphocytes and recognized p53 overexpressing tumors in vitro (Theobald et al., 1995; Ropke et al., 1996; Nijman et al., 1994). In other aspects, the resistance of a cancer to one or more therapies is related to the activity and/or expression of a self gene product, such as its overexpression. The present invention contemplates the in vivo treatment of hyperproliferative diseases by eliciting an anti-self gene immune response directed against cells presenting self gene antigen on their surface. In certain embodiments of the present invention, an expression construct comprising a self gene under the control of a promoter operable in eukaryotic cells is administered and expressed in dendritic cells in order to prime an immune response against p53, as an example.

A. Viral Transformation

1. Adenoviral Infection

One method for delivery of the recombinant DNA involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a recombinant gene construct that has been cloned therein.

The vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) have disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

The adenovirus vector may be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Animal studies have suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

2. Retroviral Infection

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, packaging cell lines are available that should greatly decrease the likelihood of recombination (Markowitz et al., 1988; Hersdorffer et al., 1990).

3. AAV Infection

Adeno-associated virus (AAV) is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin, et al., 1984; Laughlin, et al., 1986; Lebkowski, et al., 1988; McLaughlin, et al., 1988), which means it is applicable for use with the present invention. Details concerning the generation and use of rAAV vectors are described in U.S. Pat. No. 5,139,941 and U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt et al., 1994; Lebkowski et al., 1988; Samulski et al., 1989; Shelling and Smith, 1994; Yoder et al., 1994; Zhou et al., 1994; Hermonat and Muzyczka, 1984; Tratschin et al., 1985; McLaughlin et al., 1988) and genes involved in human diseases (Flotte et al., 1992; Luo et al., 1994; Ohi et al., 1990; Walsh et al., 1994; Wei et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild-type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild-type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994a; Clark et al., 1995). Cell lines carrying the rAAV DNA as an integrated provirus can also be used (Flotte et al., 1995).

4. Other Viral Vectors

Other viral vectors may be employed as constructs in the present invention. Vectors derived from viruses such as vaccinia virus (Ridgeway, 1988; Baichwal and Sugden, 1986; Coupar et al., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990). Alternatively, Alphavirus vectors and replicons may be employed (Leitner et al., 2000; Caley et al., 1999).

A molecularly cloned strain of Venezuelan equine encephalitis (VEE) virus has been genetically refined as a replication competent vaccine vector for the expression of heterologous viral proteins (Davis et al., 1996). Studies have demonstrated that VEE infection stimulates potent CTL responses and has been sugested that VEE may be an extremely useful vector for immunizations (Caley et al., 1997). It is contemplated in the present invention, that VEE virus may be useful in targeting dendritic cells.

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

B. Non-Viral Delivery

In addition to viral delivery of the self gene, the following are additional methods of recombinant gene delivery to a given host cell and are thus considered in the present invention.

1. Electroporation

In certain preferred embodiments of the present invention, the gene construct is introduced into the dendritic cells via electroporation. Electroporation involves the exposure of a suspension of cells and DNA to a high-voltage electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

It is contemplated that electroporation conditions for dendritic cells from different sources may be optimized. One may particularly wish to optimize such parameters as the voltage, the capacitance, the time and the electroporation media composition. The execution of other routine adjustments will be known to those of skill in the art.

2. Particle Bombardment

Another embodiment of the invention for transferring a naked DNA construct into cells involves particle bombardment. This method depends on the ability to accelerate DNA-coated microprojectiles to a high velocity allowing them to pierce cell membranes and enter cells without killing them (Klein et al., 1987). The microprojectiles used have consisted of biologically inert substances such as tungsten, platinum or gold beads.

It is contemplated that in some instances DNA precipitation onto metal particles would not be necessary for DNA delivery to a recipient cell using particle bombardment. It is contemplated that particles may contain DNA rather than be coated with DNA. Hence it is proposed that DNA-coated particles may increase the level of DNA delivery via particle bombardment but are not, in and of themselves, necessary.

Several devices for accelerating small particles have been developed. One such device relies on a high voltage discharge to generate an electrical current, which in turn provides the motive force (Yang et al., 1990). Another method involves the use of a Biolistic Particle Delivery System, which can be used to propel particles coated with DNA through a screen, such as stainless steel or Nytex screen, onto a filter surface covered with cells in suspension. The screen disperses the particles so that they are not delivered to the recipient cells in large aggregates. It is believed that a screen intervening between the projectile apparatus and the cells to be bombarded reduces the size of projectile aggregates and may contribute to a higher frequency of transformation by reducing the damage inflicted on the recipient cells by projectiles that are too large.

For the bombardment, cells in suspension are preferably concentrated on filters, or alternatively on solid culture medium. The cells to be bombarded are positioned at an appropriate distance below the macroprojectile stopping plate. If desired, one or more screens are also positioned between the acceleration device and the cells to be bombarded.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity or either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of primordial germ cells.

Accordingly, it is contemplated that one may wish to adjust various of the bombardment parameters in small scale studies to fully optimize the conditions. One may particularly wish to adjust physical parameters such as gap distance, flight distance, tissue distance and helium pressure. One may also optimize the trauma reduction factors by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art.

3. Calcium Phosphate Co-Precipitation or DEAE-Dextran Treatment

In other embodiments of the present invention, the transgenic construct is introduced to the cells using calcium phosphate co-precipitation. Mouse primordial germ cells have been transfected with the SV40 large T antigen, with excellent results (Watanabe et al., 1997). Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

In another embodiment, the expression construct is delivered into the cell using DEAE-dextran followed by polyethylene glycol. In this manner, reporter plasmids were introduced into mouse myeloma and erythroleukemia cells (Gopal, 1985).

4. Direct Microinjection or Sonication Loading

Further embodiments of the present invention include the introduction of the gene construct by direct microinjection or sonication loading. Direct microinjection has been used to introduce nucleic acid constructs into *Xenopus* oocytes (Harland and Weintraub, 1985), and LTK fibroblasts have been transfected with the thymidine kinase gene by sonication loading (Fechheimer et al., 1987).

5. Liposome Mediated Transformation

In a further embodiment of the invention, the gene construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL) or DOTAP-Cholesterol formulations.

Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1.

C. Vectors and Regulatory Signals

Vectors of the present invention are designed, primarily, to transform dendritic cells with the self gene under the control of regulated eukaryotic promoters (i.e., inducible, repressable, tissue specific). Also, the vectors usually will contain a selectable marker if, for no other reason, to facilitate their production in vitro. However, selectable markers may play an important role in producing recombinant cells and thus a discussion of promoters is useful here. Table 2 and Table 3 below, list inducible promoter elements and enhancer elements, respectively.

TABLE 2

Inducible Elements

| Element | Inducer | References |
|---|---|---|
| MT II | Phorbol Ester (TPA) Heavy metals | Palmiter et al., 1982; Haslinger and Karin, 1985; Searle et al., 1985; Stuart et al., 1985; Imagawa et al., 1987; Karin et al., 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Yamamoto et al., 1983; Lee et al., 1984; Ponta et al., 1985; Si.e., i et al., 1986 |
| β-Interferon | poly(rI) × poly(rc) | Tavernier et al., 1983 |
| Adenovirus 5 E2 | Ela | Imperiale and Nevins, 1984 |
| Collagenase | Phorbol Ester (TPA) | Angel et al., 1987a |
| Stromelysin | Phorbol Ester (TPA) | Angel et al., 1987b |
| SV40 | Phorbol Ester (TFA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | Ela, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | PMA | Hensel et al., 1989 |
| Thyroid Stimulating Hormone α Gene | Thyroid Hormone | Chatterjee et al., 1989 |

TABLE 3

Other Promoter/Enhancer Elements

| Promoter/Enhancer | References |
|---|---|
| Immunoglobulin Heavy Chain | Banerji et al., 1983; Gillies et al., 1983; Grosschedl and Baltimore, 1985; Atchinson and Perry, 1986, 1987; Imler et al., 1987; Neuberger et al., 1988; Kiledjian et al., 1988; |

TABLE 3-continued

Other Promoter/Enhancer Elements

| Promoter/Enhancer | References |
|---|---|
| Immunoglobulin Light Chain | Queen and Baltimore, 1983; Picard and Schaffner, 1985 |
| T-Cell Receptor | Luria et al., 1987, Winoto and Baltimore, 1989; Redondo et al., 1990 |
| HLA DQ α and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRα | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987, Tronche et al., 1989, 1990 |
| α-Fetoprotein | Godbout et al., 1988; Campere and Tilghman, 1989 |
| γ-Globin | Bodine and Ley, 1987; Perez-Stable and Constantini, 1990 |
| β-Globin | Trudel and Constantini, 1987 |
| c-fos | Cohen et al., 1987 |
| c-HA-ras | Triesman, 1985; Deschamps et al., 1985 |
| Insulin | Edlund et al., 1985 |
| Neural Cell Adhesion Molecule (NCAM) | Hirsch et al., 1990 |
| $a_1$-Antitrypain | Latimer et al., 1990 |
| H2B (TH2B) Histone | Hwang et al., 1990 |
| Mouse or Type I Collagen | Rippe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; Hen et al., 1986; Si.e., i et al., 1988; Campbell and Villarreal, 1988 |
| Retroviruses | Kriegler and Botchan, 1983; Kriegler et al., 1984a, b; Bosze et al., 1986; Miksicek et al., 1986; Celander and Haseltine, 1987; Thiesen et al., 1988; Celander et al., 1988; Chol et al., 1996; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987, Stephens and Hentschel, 1987 |
| Hepatitis B Virus | Bulla and Siddiqui, 1988; Jameel and Siddiqui, 1986; Shaul and Ben-Levy, 1987; Spandau and Lee, 1988 |
| Human Immunodeficiency Virus | Muesing et al., 1987; Hauber and Cullan, 1988; Jakobovits et al., 1988; Feng and Holland, 1988; Takebe et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

Preferred for use in the present invention is the cytomegalovirus (CMV) promoter. This promoter is commercially available from Invitrogen in the vector pcDNAIII, which is preferred for use in the present invention. Also contemplated as useful in the present invention are the dectin-1 and dectin-2 promoters. Below are a list of additional viral promoters, cellular promoters/enhancers and inducible promoters/enhancers that could be used in combination with the present invention. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

The use of internal ribosome binding sites (IRES) elements are used to create multigene, or polycistronic, messages. IRES elements are able to bypass the ribosome scanning model of 5'-methylated cap-dependent translation and begin translation at internal sites (Pelletier and Sonenberg, 1988). IRES elements from two members of the picomavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message. Another signal that may prove useful is a polyadenylation signal (hGH, BGH, SV40).

As discussed above, in certain embodiments of the invention, a cell may be identified and selected in vitro or in vivo by including a marker in the expression construct. Such markers confer an identifiable change to the cell permitting easy identification of cells containing the expression construct. Usually, the inclusion of a drug selection marker aids in cloning and in the selection of transformants, for example, genes that confer resistance to neomycin, puromycin, hygromycin, DHFR, GPT, zeocin, tetracycline and histidinol are useful selectable markers. Alternatively, enzymes such as herpes simplex virus thymidine kinase (tk) or chloramphenicol acetyltransferase (CAT) may be employed.

The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either co-operatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements On the other hand, a promoter must have one or more elements that direct initiation of RNA synthesis at a particular site and in a particular orientation, whereas enhancers lack these specificities. Aside from this operational distinction, enhancers and promoters are very similar entities.

Promoters and enhancers have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

In any event, it will be understood that promoters are DNA elements which when positioned functionally upstream of a gene leads to the expression of that gene. Most transgene constructs of the present invention are functionally positioned downstream of a promoter element.

X. PHARMACEUTICAL COMPOSITIONS AND ROUTES OF SELF GENE DELIVERY

In a preferred embodiment of the present invention, a method of treating a subject with a hyperproliferative disease in which self gene expression is increased or altered is contemplated, and in particular aspects one or more cells of the subject are resistant to one or more therapies of the hyperproliferative disease. Hyperproliferative diseases or resistance of a therapy thereto that are most likely to be treated in the present invention are those that result from mutations in the self gene and the overexpression of self gene protein in the resistant hyperproliferative cells. Examples of hyperproliferative diseases contemplated for treatment are lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon, breast and bladder and any other hyperproliferative diseases that involve mutations and upregulation of self gene expression, for example. An important aspect of this embodiment is the delivery of a self gene adenoviral vector to dendritic cells, for processing and presentation of self gene antigenic peptides to immune effector cells, thereby stimulating an anti-self gene response. In one embodiment, a self gene adenovirus concentration range of 100-300 PFU/cell transduces greater than 50% of the dendritic cells. The preferred mode of delivering the self gene construct in the present invention is by adenoviral vector, in a certain aspect of the invention.

In a preferred embodiment of the present invention, a method of treating a subject with a therapy-resistant hyperproliferative disease in which p53 expression is upregulated is contemplated. Hyperproliferative diseases and therapy resistances thereof that are most likely to be treated in the present invention are those that result from mutations in the p53 gene and the overexpression of p53 protein in the hyperproliferative cells. Examples of hyperproliferative diseases contemplated for treatment are lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon, rectal, breast and -bladder and any other hyperproliferative diseases that involve mutations and upregulation of p53 expression. An important aspect of this embodiment is the delivery of a p53 adenoviral vector to dendritic cells, for processing and presentation of p53 antigenic peptides to immune effector cells, thereby stimulating an anti-p53 response. In one embodiment, a p53 adenovirus concentration range of 100-300 PFU/cell transduces greater than 50% of the dendritic cells. The preferred mode of delivering the p53 adenoviral vector construct in the present invention is by intradermal injection of dendritic cells, although other modes are contemplated. In certain embodiments, the injection site is pretreated with chemokines or cytokines to elicit dendritic cell migration and maturation to the site of intradermal injection. In further embodiments, administration of the self gene adenoviral vector to dendritic cells comprises multiple intradermal injections. For example, the treatment of certain cancer types may require at least 3 or more immunizations, every 2-4 weeks. Dendritic cell intradermal injection may further be performed local, regional, or distal to the site of tumor growth, as well as subcutaneous, intraperitoneal or injection into or near a draining lymph node, for example. Identifying, isolating, and obtaining dendritic cells are described herein.

In certain embodiments, the present invention also concerns formulations of one or more self gene adenovirus compositions for administration to a mammal, that transduces dendritic cells of the mammal. For the treatment of therapy-resistant hyperproliferative disease in humans, it is contemplated that the adenovirus vector is replication-defective, comprising a self gene under the control of a promoter operable in eukaryotic cells (e.g., CMV IE, dectin-1, dectin-2). It will also be understood that, if desired, the self gene compositions disclosed herein may be administered in combination with other agents as well, such as, e.g., various pharmaceutically-active agents. As long as the composition comprises at least one self gene expression construct, there is virtually no limit to other components which may also be included, given that the additional agents do not cause a significant adverse effect upon contact with the dendritic cells.

Adjuvants are substances that non-specifically enhance or potentiate the immune response (e.g., CTLs) to an antigen, and would thus be considered useful in formulations of the present invention. For example, cholera toxin acts locally as a mucosal adjuvant for the induction of peptide-specific CTLs following intranasal immunization of dendritic cells with CTL epitope peptides (Porgador et al., 1997; Porgador et al., 1998). Several immunological adjuvants (e.g., MF59) specific for dendritic cells and their preparation have been described previously (Dupis et al., 1998; Allison, 1997; Allison, 1998). The use of such adjuvants in the present invention are considered. In another embodiment of the present invention, cytokines are used in combination with the delivery of the p53 expression construct. Cytokines are secreted, low-molecular weight proteins that regulate the intensity and duration of the immune response by exerting a variety of effects on lymphocytes and other immune cells. Several cytokines have been directly linked to influencing dendritic cell migration to lymphoid tissues (e.g., TNF-α), accelerating the maturation of dendritic cells into efficient antigen-presenting cells for T-lymphocytes (e.g., GM-CSF, IL-1 and IL-4) (Dupis et al., 1998; Allison, 1997; Allison, 1998; U.S. Pat. No. 5,849,589, specifically incorporated herein by reference in its entirety) and acting as immunoadjuvants (e.g., IL-12) (Gabrilovich et al., 1996). The use of these and other cytokines (e.g., FLT-3 ligand, CD 40) are considered in the present invention.

The formulation of pharmaceutically-acceptable excipients and carrier solutions are well-known to those of skill in the art, as is the development of suitable dosing and treatment regimens for using the particular compositions described herein in a variety of treatment regimens, including, e.g., intradermal, parenteral, intravenous, intramuscular, intranasal, intratumoral, intrathecal, and/or oral administration and formulation.

A. Injectable Compositions and Delivery

The preferred method of the self gene adenovirus expression construct delivery to dendritic cells in the present invention is via intradermal injection. However, the pharmaceutical compositions disclosed herein may alternatively be administered parenterally, intravenously, intramuscularly, or even intraperitoneally as described in U.S. Pat. No. 5,543,158; U.S. Pat. No. 5,641,515 and U.S. Pat. No. 5,399,363 (each specifically incorporated herein by reference in its entirety). Injection of self gene constructs and transduced dendritic cells may be delivered by syringe or any other method used for injection of a solution, as long as the expression construct or transduced cells can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils, for example. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety, and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

B. Oral Compositions and Delivery

The pharmaceutical compositions disclosed herein may be delivered via oral administration to an animal, and as such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. No. 5,641,515; U.S. Pat. No. 5,580,579 and U.S. Pat. No. 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium-borate solution (Dobell's Solution). Alternatively, the active ingredient may be incorporated into an oral solution such as those containing sodium borate, glycerin and potassium bicarbonate, or dispersed in a dentifrice, including: gels, pastes, powders and slurries, or added in a therapeutically effective amount to a paste dentifrice that may include water, binders, abrasives, flavoring agents, foaming agents, and humectants, or alternatively fashioned into a tablet or solution form that may be placed under the tongue or otherwise dissolved in the mouth.

C. Additional Modes of Delivery

In addition to the methods of delivery described above, the following techniques are also contemplated as alternative methods of self gene delivery. Sonophoresis (i.e., ultrasound) has been used and described in U.S. Pat. No. 5,656,016 (specifically incorporated herein by reference in its entirety) as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. No. 5,770,219 and U.S. Pat. No. 5,783,208), rectal delivery (U.S. Pat. No. 5,811,128) and feedback controlled delivery (U.S. Pat. No. 5,697,899), each specifically incorporated herein by reference in its entirety.

XI. MONITORING IMMUNE RESPONSE

In one embodiment of the present invention, self gene adenovirus vectors are intradermally administered to dendritic cells. Subsequently, the dendritic cells express and present self gene antigens to immune effector cells, thereby stimulating an anti-self gene response. In another embodiment, the immune effector cells are cytotoxic T lymphocytes (CTLs). Thus, an important aspect of the invention is the ability to monitor immune responses, specifically CTLs.

A. CTL Assay

Cytotoxic T lymphocyte activity can be assessed in freshly isolated peripheral blood mononuclear cells (PBMC), in phytohaemaglutinin-stimulat-ed IL-2 expanded cell lines established from PBMC (Bernard et al., 1998) or by T cells isolated from previously immunized subjects and restimulated for 6 days with DC infected with Adenovirus self gene using standard 6 h $^{51}$Cr release microtoxicity assays. Colonic T-cells have been tested for their ability to mediate both perforin and Fas ligand-dependent killing in redirected cytotoxicity assays (Simpson et al., 1998). The colon cytotoxic T lymphocytes displayed both Fas- and perforin-dependent killing. Recently, an in vitro dehydrogenase release assay has been developed that takes advantage of a new fluorescent amplification system (Page et al., 1998). This approach is sensitive, rapid, reproducible and may be used advantageously for mixed lymphocyte reaction (MLR). It may easily be further automated for large scale cytotoxicity testing using cell membrane integrity, and is thus considered in the present invention. In another fluorometric assay developed for detecting cell-mediated cytotoxicity, the fluorophore used is the non-toxic molecule alamar blue (Nociari et al., 1998). The alamarBlue is fluorescently quenched (i.e., low quantum yield) until mitochondrial reduction occurs, which then results in a dramatic increase in the alamarBlue fluorescence intensity (i.e., increase in the quantum yield). This assay is reported to be extremely sensitive, specific and requires a significantly lower number of effector cells than the standard $^{51}$Cr release assay.

B. Anti-CTL Antibodies

It is also contemplated in the present invention, that antibodies directed against specific CTL epitopes may be used to assay CTL immune responses. The culturing and activation of mononuclear leukocytes with a standard stimulus known to activate such cells has been described in U.S. Pat. No. 5,843,689 (specifically incorporated herein by reference in its entirety). After culturing, aliquots of the cells are incubated with fluorophore-conjugated monoclonal antibodies to antigenic determinants of a particular mononuclear subclass (e.g., CTLs). The incubated aliquots are analyzed on a flow cytofluorometer. It is contemplated that the use of CTL specific monoclonal antibodies and fluorophore-conjugated monoclonal antibodies (e.g., CD8+, FasL, CD4+) will be of particular use as assays in the present invention.

XII. EX VIVO PREPARATION OF DENDRITIC CELLS

In one embodiment of the present invention, a method for a self gene-directed (such as p53-directed, for example) immune response in a subject is induced by at least one of the following: 1) obtaining dendritic cells from the subject, 2) infecting dendritic cells with an adenoviral vector comprising a p53 gene under the control of a promoter operable in eukaryotic cells; and 3) the p53 adenovirus-infected dendritic cells are administered to the subject. It is contemplated that infected dendritic cells will present p53 antigens to immune effector cells and therefore stimulate an anti-p53 response in the subject. Thus, an important aspect of the present invention is to obtain dendritic cells from the subject or induce precursor cells (e.g., monocytes) to differentiate into dendritic cells—for infection with p53 adenoviral vectors for use in treatment of hyperproliferative disease.

It has been observed experimentally that patients with advanced stages of certain types of cancer have reduced function of dendritic cells (i.e., defective antigen presentation), but that these patients could give rise to functional dendritic cells through the in vitro growth and stimulation of stem cells (Gabrilovich et al., 1997). The stem cells were obtained from the cancer patients, stimulated to differentiate into dendritic cells by the addition of granulocyte/macrophage colony-stimulating factor and IL4, and observed to elicit much higher levels of CTL responses than mature dendritic cells obtained from the cancer patients (Gabrilovich et al., 1997). Thus, it is contemplated in the present invention that stem cell precursor stimulated dendritic cell differentiation is used as a method for ex vivo treatment of hyperproliferative disease.

A method of culturing and inducing the differentiation of monocytes into dendritic cells has been described in U.S. Pat. No. 5,849,589 (specifically incorporated herein by reference in its entirety). The method of monocyte differentiation into dendritic cells consists of a culture medium stimulated with GM-CSF, IL-4 and TNFα. An alternate method of isolating dendritic cells has been described by Cohen et al. (U.S. Pat. No. 5,643,786, specifically incorporated herein by reference in its entirety). This method involves elutriating peripheral blood samples in at least four flow rates from an elutriation rotor. Calcium ionophore is used to stimulate monocytes isolated during the process into dendritic cells and treatment for diseases involving re-introduction of the activated dendritic cells are also disclosed. It is also possible to prepare immortalized precursor cells that is considered useful in the present invention (U.S. Pat. No. 5,830,682; U.S. Pat. No. 5,811,297, each specifically incorporated herein by reference in its entirety). In another example, an immature dendritic cell line derived from p53 growth suppressor gene deficient animals are prepared (U.S. Pat. No. 5,648,219, specifically incorporated herein by reference in its entirety). The immature dendritic cell line may be induced to become an activated, immortalized dendritic cell line that will stimulate T-cell proliferation and is thus contemplated for use in the present invention. Methods and compositions for use of human dendritic cells to activate T-cells for immunotherapeutic responses against primary and metastatic prostate cancer have also been described (U.S. Pat. No. 5,788,963, specifically incorporated herein by reference in its entirety). After the exposure of the dendritic cells to prostate cancer antigen in vitro, the dendritic cells are administered to a prostate cancer patient to activate T-cell responses in vivo. An important embodiment of the invention described above (U.S. Pat. No. 5,788,963) is a method to extend the life span of the human dendritic cells by cryopreservation. This method may be of important utility in the present invention for long term storage of p53 adenoviral-infected dendritic cells.

XIII. PHARMACEUTICALS AND METHODS OF TREATING CANCER

In a particular aspect, the present invention provides methods for the treatment of various therapy-resistant hyperproliferative diseases. Treatment methods will involve treating an individual with an effective amount of dendritic cells comprising a self gene of interest. An effective amount is described, generally, as that amount sufficient to detectably and repeatedly to ameliorate, reduce, minimize or limit the extent of the disease or its symptoms, including its resistance to one or more therapies. More rigorous definitions may apply, including elimination, eradication or cure of a therapy-resistant disease.

To kill cells, inhibit cell growth, inhibit metastasis, decrease tumor or tissue size and otherwise reverse or reduce the malignant phenotype of therapy-resistant tumor cells, using the methods and compositions of the present invention, one would generally contact a dendritic cell with the therapeutic expression construct. This may be combined with compositions comprising other agents effective in the treatment of therapy-resistant hyperproliferative cells. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent. Although in particular embodiments the exemplary p53 construct is administered within a dendritic cell, the additional therapy may or may not be administered in a dendritic cell or in the dendritic cell housing the exemplary p53 construct.

Alternatively, the dendritic cell therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell or individual with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, such as the exemplary case wherein the dendritic cell comprising the self gene product is "A" and the other therapy is "B":

A/B/A  B/A/B  B/B/A  A/A/B  A/B/B  B/A/A  A/B/B/B

B/A/B/B  B/B/B/A  B/B/A/B  A/A/B/B  A/B/A/B  A/B/B/A

B/B/A/A  B/A/B/A  B/A/A/B  A/A/A/B  B/A/A/A  A/B/A/A

A/A/B/A

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described dendritic cell therapy.

Aqueous compositions of the present invention comprise an effective amount of the compound, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

The treatments may include various "unit doses." Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time. Unit dose of the present invention may conveniently may be described in terms of plaque forming units (pfu) of the viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher.

Preferably, patients will have adequate bone marrow function (defined as a peripheral absolute granulocyte count of >2,000/mm$^3$ and a platelet count of 100,000/mm$^3$), adequate liver function (bilirubin<1.5 mg/dl) and adequate renal function (creatinine<1.5 mg/dl).

A. Gene Therapy

One of the preferred embodiments of the present invention involves the use of viral vectors to deliver therapeutic genes to dendritic cells for the treatment of cancer, and this embodiment may concern the dendritic cell/self gene product, the other therapy, or both therapies. Resistant cancer cells to be treated include cancers of the lung, brain, prostate, kidney, liver, ovary, breast, skin, stomach, esophagus, head and neck, testicles, colon, cervix, lymphatic system and blood. Of particular interest are non-small cell lung carcinomas including squamous cell carcinomas, adenocarcinomas and large cell undifferentiated carcinomas, tumor suppressors, antisense oncogenes, and inhibitors of apoptosis.

According to the present invention, one may treat the resistant cancer by directly injection a tumor with the viral vector. Alternatively, the resistant tumor may be infused or perfused with the vector using any suitable delivery vehicle. Local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe or catherization is preferred. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs.

For tumors of >4 cm, the volume to be administered will be about 4-10 ml (preferably 10 ml), while for tumors of <4 cm, a volume of about 1-3 ml will be used (preferably 3 ml). Multiple injections delivered as single dose comprise about 0.1 to about 0.5 ml volumes. The viral particles may advantageously be contacted by administering multiple injections to the tumor, spaced at approximately 1 cm intervals.

In certain embodiments, the tumor being treated may not, at least initially, be resectable. Treatments with therapeutic viral constructs may increase the resectability of the tumor due to shrinkage at the margins or by elimination of certain particularly invasive portions. Following treatments, resection may be possible. Additional viral treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two-week period. The two-week regimen may be repeated one, two, three, four, five, six or more times. During a course of treatment, the need to complete the planned dosings may be re-evaluated.

B. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, paclitaxel, transplatinum, 5-fluorouracil, vincristin, vinblastin and methotrexate or any analog or derivative variant thereof.

In specific embodiments, chemotherapy is employed that upregulates expression of p53.

C. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

XIV. CHEMOTHERAPY

In some embodiments of the invention, chemotherapy relates to the invention. For example, a subject may be or a subject may become resistant to one or more particular chemotherapies, and/or a chemotherapy may be employed in conjunction with a method of the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylomithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor and a HER2 expression inhibitor; vaccines such as gene therapy vaccines and pharmaceutically acceptable salts, acids or derivatives of any of the above.

List of FDA-approved oncology drugs. The generic product terminology is followed by the trademarked product name, then the approved indications and date of approval, which may be obtained on the world wide web address of the U.S. Food and Drug Administration:

| | | | | |
|---|---|---|---|---|
| Aldesleukin | Proleukin | | Chiron Corp | May 05, 1992 |
| Alemtuzumab | Campath | Accel. Approv. (clinical benefit not established) Campath is indicated for the treatment of B-cell chronic lymphocytic leukemia (B-CLL) in patients who have been treated with alkylating agents and who have failed fludarabine therapy. | Millennium and ILEX Partners, LP | May 07, 2001 |
| alitretinoin | Panretin | Topical treatment of cutaneous lesions in patients with AIDS-related Kaposi's sarcoma. | Ligand Pharmaceuticals | Feb. 02, 1999 |
| allopurinol | Zyloprim | Patients with leukemia, lymphoma and solid tumor malignancies who are receiving cancer therapy which causes elevations of serum and urinary uric acid levels and who cannot tolerate oral therapy. | GlaxoSmithKline | May 17, 1996 |
| altretamine | Hexalen | Single agent palliative treatment of patients with persistent or recurrent ovarian cancer following first-line therapy with a cisplatin and/or alkylating agent based combination. | US Bioscience | Dec. 26, 1990 |
| amifostine | Ethyol | To reduce the cumulative renal toxicity associated with repeated administration of cisplatin in patients with advanced ovarian cancer | US Bioscience | Dec. 08, 1995 |
| amifostine | Ethyol | Accel. Approv. (clinical benefit not established) Reduction of platinum toxicity in non-small cell lung cancer | US Bioscience | Mar. 15, 1996 |
| amifostine | Ethyol | To reduce post-radiation xerostomia for head and neck cancer where the radiation port includes a substantial portion of the parotid glands. | US Bioscience | Jun. 24, 1999 |
| anastrozole | Arimidex | Accel. Approv. (clinical benefit not established) for the adjuvant treatment of postmenopausal women with hormone receptor positive early breast cancer | AstraZeneca | Sep. 05, 2002 |
| anastrozole | Arimidex | Treatment of advanced breast cancer in postmenopausal women with disease progression following tamoxifen therapy. | AstraZeneca Pharmaceuticals | Dec. 27, 1995 |
| anastrozole | Arimidex | For first-line treatment of postmenopausal women with hormone receptor positive or hormone receptor unknown locally advanced or metastatic breast cancer. | AstraZeneca Pharmaceuticals | Sep. 01, 2000 |
| arsenic trioxide | Trisenox | Second line treatment of relapsed or refractory APL following ATRA plus an anthracycline. | Cell Therapeutic | Sep. 25, 2000 |
| Asparaginase | Elspar | ELSPAR is indicated in the therapy of patients with acute lymphocytic leukemia. This agent is useful primarily in combination with other chemotherapeutic agents in the induction of remissions of the disease in pediatric patients. | Merck & Co, Inc | Aug. 01, 2002 |
| BCG Live | TICE BCG | | Organon Teknika Corp | Aug. 21, 1998 |
| bexarotene capsules | Targretin | For the treatment by oral capsule of cutaneous manifestations of cutaneous T-cell lymphoma in patients who are refractory to at least one prior systemic therapy. | Ligand Pharmaceuticals | Dec. 29, 1999 |
| bexarotene gel | Targretin | For the topical treatment of cutaneous manifestations of cutaneous T-cell lymphoma in patients who are refractory to at least one prior sytemic therapy. | Ligand Pharmaceuticals | Jun. 28, 2000 |
| bleomycin | Blenoxane | | Bristol-Myers Sqiubb | Jul. 31, 1973 |
| bleomycin | Blenoxane | Sclerosing agent for the treatment of malignant pleural effusion (MPE) and prevention of recurrent pleural effusions. | Bristol-Myers Squibb | Feb. 20, 1996 |
| busulfan intravenous | Busulfex | Use in combination with cyclophoshamide as conditioning regimen prior to allogeneic hematopoietic progenitor cell transplantation for chronic myelogenous leukemia. | Orphan Medical, Inc | Feb. 04, 1999 |
| busulfan oral | Myleran | Chronic Myelogenous Leukemia-palliative therapy | GlaxoSmithKline | Jun. 26, 1954 |
| calusterone | Methosarb | | Pharmacia & Upjohn Company | Feb. 20, 1973 |
| capecitabine | Xeloda | Accel. Approv. (clinical benefit subsequently established) Treatment of metastatic breast cancer resistant to both paclitaxel and an anthracycline containing chemotherapy regimen or resistant to paclitaxel and for whom further anthracycline therapy may be contraindicated, e.g., patients | Roche | Apr. 30, 1998 |

| | | | | |
|---|---|---|---|---|
| | | who have received cumulative doses of 400 mg/m2 of doxorubicin or doxorubicin equivalents | | |
| capecitabine | Xeloda | Initial therapy of patients with metastatic colorectal carcinoma when treatment with fluoropyrimidine therapy alone is preferred. Combination chemotherapy has shown a survival benefit compared to 5-FU/LV alone. A survival benefit over 5_FU/LV has not been demonstrated with Xeloda monotherapy. | Roche | Apr. 30, 2001 |
| capecitabine | Xeloda | Treatment in combination with docetaxel of patients with metastatic breast cancer after failure of prior anthracycline containing chemotherapy | Roche | Sep. 07, 2001 |
| carboplatin | Paraplatin | Palliative treatment of patients with ovarian carcinoma recurrent after prior chemotherapy, including patients who have been previously treated with cisplatin. | Bristol-Myers Squibb | Mar. 03, 1989 |
| carboplatin | Paraplatin | Initial chemotherapy of advanced ovarian carcinoma in combination with other approved chemotherapeutic agents. | Bristol-Myers Squibb | Jul. 05, 1991 |
| carmustine | BCNU, BiCNU | | Bristol-Myers Squibb | Mar. 07, 1997 |
| carmustine with Polifeprosan 20 Implant | Gliadel Wafer | For use in addition to surgery to prolong survival in patients with recurrent glioblastoma multiforme who qualify for surgery. | Guilford Pharmaceuticals Inc. | Sep. 23, 1996 |
| celecoxib | Celebrex | Accel. Approv. (clinical benefit not established) Reduction of polyp number in patients with the rare genetic disorder of familial adenomatous polyposis. | Searle | Dec. 23, 1999 |
| chlorambucil | Leukeran | Chronic Lymphocytic Leukemia - palliative therapy | GlaxoSmithKline | |
| chlorambucil | Leukeran | | GlaxoSmithKline | Mar. 18, 1957 |
| cisplatin | Platinol | Metastatic testicular-in established combination therapy with other approved chemotherapeutic agents in patients with metastatic testicular tumors whoc have already received appropriate surgical and/or radiotherapeutic procedures. An established combination therapy consists of Platinol, Blenoxane and Velbam. | Bristol-Myers Squibb | Dec. 19, 1978 |
| cisplatin | Platinol | Metastatic ovarian tumors - in established combination therapy with other approved chemotherapeutic agents: Ovarian-in established combination therapy with other approved chemotherapeutic agents in patients with metastatic ovarian tumors who have already received appropriate surgical and/or radiotherapeutic procedures. An established combination consists of Platinol and Adriamycin. Platinol, as a single agent, is indicated as secondary therapy in patients with metastatic ovarian tumors refractory to standard chemotherapy who have not previously received Platinol therapy. | Bristol-Myers Squibb | Dec. 19, 1978 |
| cisplatin | Platinol | as a single agent for patients with transitional cell bladder cancer which is no longer amenable to local treatments such as surgery and/or radiotherapy. | Bristol-Myers Squibb | Apr. 22, 1993 |
| cladribine | Leustatin, 2-CdA | Treatment of active hairy cell leukemia. | R. W. Johnson Pharmaceutical Research Institute | Feb. 26, 1993 |
| cyclophosphamide | Cytoxan, Neosar | | Bristol-Myers Squibb | Nov. 16, 1959 |
| cyclophosphamide | Cytoxan Injection | | Bristol-Myers Squibb | Nov. 16, 1959 |
| cyclophosphamide | Cytoxan Injection | | Bristol-Myers Squibb | Apr. 29, 1987 |
| cyclophosphamide | Cytoxan Tablet | | Bristol-Myers Squibb | Apr. 29, 1987 |
| cytarabine | Cytosar-U | | Pharmacia & Upjohn Company | Jun. 17, 1969 |
| cytarabine liposomal | DepoCyt | Accel. Approv. (clinical benefit not established) Intrathecal therapy of lymphomatous meningitis | Skye Pharmaceuticals | Apr. 01, 1999 |
| dacarbazine | DTIC-Dome | | Bayer | May 27, 1975 |
| dactinomycin, actinomycin D | Cosmegen | | Merck | Feb. 04, 1964 |
| dactinomycin, actinomycin D | Cosmegan | | Merck | Dec. 10, 1964 |

-continued

| | | | | |
|---|---|---|---|---|
| Darbepoetin alfa | Aranesp | Treatment of anemia associated with chronic renal failure. | Amgen, Inc | Sep. 17, 2001 |
| Darbepoetin alfa | Aranesp | Aranesp is indicated for the treatment of anemia in patients with non-myeloid malignancies where anemia is due to the effect of concomitantly administered chemotherapy. | Amgen, Inc | Jul. 19, 2002 |
| daunorubicin liposomal | DanuoXome | First line cytotoxic therapy for advanced, HIV related Kaposi's sarcoma. | Nexstar, Inc. | Apr. 08, 1996 |
| daunorubicin, daunomycin | Daunorubicin | Leukemia/myelogenous/monocytic/erythroid of adults/remission induction in acute lymphocytic leukemia of children and adults. | Bedford Labs | Jan. 30, 1998 |
| daunorubicin, daunomycin | Cerubidine | In combination with approved anticancer drugs for induction of remission in adult ALL. | Wyeth Ayerst | Mar. 11, 1987 |
| Denileukin diftitox | Ontak | Accel. Approv. (clinical benefit not established) treatment of patients with persistent or recurrent cutaneous T-cell lymphoma whose malignant cells express the CD25 component of the IL-2 receptor | Seragen, Inc | Feb. 05, 1999 |
| dexrazoxane | Zinecard | Accel. Approv. (clinical benefit subsequently established) Prevention of cardiomyopathy associated with doxorubicin administration | Pharmacia & Upjohn Company | May 26, 1995 |
| dexrazoxane | Zinecard | reducing the incidence and severity of cardiomyopathy associated with doxorubicin administration in women with metastatic breast cancer who have received a cumulative doxorubicin dose of 300 mg/m2 and who will continue to receive doxorubicin therapy to maintain tumor control. It is not recommended for use with the initiation of doxorubicin therapy. | Pharmacia & Upjohn Company | Oct. 31, 2002 |
| docetaxel | Taxotere | Accel. Approv. (clinical benefit subsequently established) Treatment of patients with locally advanced or metastatic breast cancer who have progressed during anthracycline-based therapy or have relapsed during anthracycline-based adjuvant therapy. | Aventis Pharmaceutical | May 14, 1996 |
| docetaxel | Taxotere | For the treatment of locally advanced or metastatic breast cancer which has progressed during anthracycline-based treatment or relapsed during anthracycline-based adjuvant therapy. | Aventis Pharmaceutical | Jun. 22, 1998 |
| docetaxel | Taxotere | For locally advanced or metastatic non-small cell lung cancer after failure or prior platinum-based chemotherapy. | Aventis Pharmaceutical | Dec. 23, 1999 |
| docetaxel | Taxotere | | Aventis Pharmaceutical | Nov. 27, 2002 |
| docetaxel | Taxotere | in combination with cisplatin for the treatment of patients with unresectable, locally advanced or metastatic non-small cell lung cancer who have not previously received chemotherapy for this condition. | Aventis Pharmaceutical | Nov. 27, 2002 |
| doxorubicin | Adriamycin, Rubex | | Pharmacia & Upjohn Company | Aug. 07, 1974 |
| doxorubicin | Adriamycin PFS Injectionintravenous injection | Antibiotic, antitumor agent. | Pharmacia & Upjohn Company | Dec. 23, 1987 |
| doxorubicin liposomal | Doxil | Accel. Approv. (clinical benefit not established) Treatment of AIDS-related Kaposi's sarcoma in patients with disease that has progressed on prior combination chemotherapy or in patients who are intolerant to such therapy. | Sequus Pharmaceuticals, Inc. | Nov. 17, 1995 |
| doxorubicin liposomal | Doxil | Accel. Approv. (clinical benefit not established) Treatment of metastatic carcinoma of the ovary in patient with disease that is refractory to both paclitaxel and platinum based regimens | Sequus Pharmaceuticals, Inc. | Jun. 28, 1999 |
| DROMOSTANOLONE PROPIONATE | DROMOSTANOLONE | | Eli Lilly | Oct. 26, 1961 |
| DROMOSTANOLONE PROPIONATE | MASTERONE INJECTION | | SYNTEX | Oct. 08, 1964 |
| Elliott's B Solution | Elliott's B Solution | Diluent for the intrathecal administration of methotrexate sodium and cytarabine for the prevention or treatment of meningeal leukemia or lymphocytic lymphoma. | Orphan Medical, Inc | Sep. 27, 1996 |
| epirubicin | Ellence | A component of adjuvant therapy in patients with evidence of axillary node tumor involvement following resection of primary breast cancer. | Pharmacia & Upjohn Company | Sep. 15, 1999 |
| Epoetin alfa | epogen | EPOGENB is indicated for the reatment of anemia related to therapy with zidovudine in HIV-infected patients. EPOGENB is indicated to elevate or maintain the red blood cell level (as manifested by the hematocrit or hemoglobin determinations) and to decrease the need for transfusions in these patients. EPOGEND is not indicated for the treatment of anemia in HIV- | Amgen, Inc | Jul. 26, 1999 |

| | | | | |
|---|---|---|---|---|
| Epoetin alfa | epogen | infected patients due to other factors such as iron or folate deficiencies, hemolysis or gastrointestinal bleeding, which should be managed appropriately. EPOGENB is indicated for the treatment of anemic patients (hemoglobin >10 to_<13 g/dL) scheduled to undergo elective, noncardiac, nonvascular surgery to reduce the need for allogeneic blood transfusions. | Amgen, Inc | Jul. 26, 1999 |
| Epoetin alfa | epogen | EPOGENB is indicated for the treatment of anemia in patients with non-myeloid malignancies where anemia is due to the effect of concomitantly administered chemotherapy. EPOGEND is indicated to decrease the need for transfusions in patients who will be receiving concomitant chemotherapy for a minimum of 2 months. EPOGENB is not indicated for the treatment of anemia in cancer patients due to other factors such as iron or folate deficiencies, hemolysis or gastrointestinal bleeding, which should be managed appropriately. | Amgen, Inc | Jul. 26, 1999 |
| Epoetin alfa | epogen | EPOGEN is indicated for the treatment of anemia associated with CRF, including patients on dialysis (ESRD) and patients not on dialysis. | Amgen, Inch | Jul. 26, 1999 |
| estramustine | Emcyt | palliation of prostate cancer | Pharmacia & Upjohn Company | Dec. 24, 1981 |
| etoposide phosphate | Etopophos | Management of refractory testicular tumors, in combination with other approved chemotherapeutic agents. | Bristol-Myers Squibb | May 17, 1996 |
| etoposide phosphate | Etopophos | Management of small cell lung cancer, first-line, in combination with other approved chemotherapeutic agents. | Bristol-Myers Squibb | May 17, 1996 |
| etoposide phosphate | Etopophos | Management of refractory testicular tumors and small cell lung cancer. | Bristol-Myers Squibb | Feb. 27, 1998 |
| etoposide, VP-16 | Vepesid | Refractory testicular tumors-in combination therapy with other approved chemotherapeutic agents in patients with refractory testicular tumors who have already received appropriate surgical, chemotherapeutic and radiotherapeutic therapy. | Bristol-Myers Squibb | Nov. 10, 1983 |
| etoposide, VP-16 | VePesid | In combination with other approved chemotherapeutic agents as first line treatment in patients with small cell lung cancer. | Bristol-Myers Squibb | Dec. 30, 1986 |
| etoposide, VP-16 | Vepesid | In combination with other approved chemotherapeutic agents as first line treatment in patients with small cell lung cancer. | Bristol-Myers Squibb | Dec. 30, 1986 |
| exemestane | Aromasin | Treatment of advance breast cancer in postmenopausal women whose disease has progressed following tamoxifen therapy. | Pharmacia & Upjohn Company | Oct. 21, 1999 |
| Filgrastim | Neupogen | | Amgen, Inc | Feb. 20, 1991 |
| Filgrastim | Neupogen | NEUPOGEN is indicated to reduce the duration of neutropenia and neutropenia-related clinical sequelae, eg, febrile neutropenia, in patients with nonmyeloid malignancies undergoing myeloablative chemotherapy followed by marrow transplantation. | Amgen, Inc | Apr. 02, 1998 |
| Filgrastim | Neupogen | NEUPOGEN is indicated to decrease the incidence of infection, as manifested by febrile neutropenia, in patients with nonmyeloid malignancies receiving myelosuppressive anticancer drugs associated with a significant incidence of severe neutropenia with fever. | Amgen, Inc | Apr. 02, 1998 |
| Filgrastim | Neupogen | NEUPOGEN is indicated for reducing the time to neutrophil recovery and the duration of fever, following induction or consolidation hemotherapy treatment of adults with AML. | Amgen, Inc | Apr. 02, 1998 |
| floxuridine (intraarterial) | FUDR | | Roche | Dec. 18, 1970 |
| fludarabine | Fludara | Palliative treatment of patients with B-cell lymphocytic leukemia (CLL) who have not responded or have progressed during treatment with at least one standard alkylating agent containing regimen. | Berlex Laboratories Inc. | Apr. 18, 1991 |
| fluorouracil, 5-FU | Adrucil | prolong survival in combination with leucovorin | ICN Puerto Rico | Apr. 25, 1962 |
| fulvestrant | Faslodex | the treatment of hormone receptor-positive metastatic breast cancer in postmenopausal women with disease progression following antiestrogen therapy | IPR | Apr. 25, 2002 |
| gemcitabine | Gemzar | Treatment of patients with locally advanced (nonresectable stage II or III) or metastatic (stage IV) adenocarcinoma of the pancreas. Indicated for first-line treatment and for patients previously treated with a 5-fluorouracil-containing regimen. | Eli Lilly | May 15, 1996 |
| gemcitabine | Gemzar | For use in combination with cisplatin for the first-line treatment of patients with inoperable, locally advanced (Stage IIIA or IIIB) or metastatic (Stage IV) non-small cell lung cancer. | Eli Lilly | Aug. 25, 1998 |

-continued

| | | | | |
|---|---|---|---|---|
| gemtuzumab ozogamicin | Mylotarg | Accel. Approv. (clinical benefit not established) Treatment of CD33 positive acute myeloid leukemia in patients in first relapse who are 60 years of age or older and who are not considered candidates for cytotoxic chemotherapy. | Wyeth Ayerst | May 17, 2000 |
| goserelin acetate | Zoladex Implant | Palliative treatment of advanced breast cancer in pre- and perimenopausal women. | AstraZeneca Pharmaceuticals | Dec. 18, 1995 |
| goserelin acetate | Zoladex | | AstraZeneca Pharmaceuticals | Dec. 18, 1995 |
| hydroxyurea | Hydrea | | Bristol-Myers Squibb | Dec. 07, 1967 |
| hydroxyurea | Hydrea | Decrease need for transfusions in sickle cell anemia | Bristol-Myers Squibb | Feb. 25, 1998 |
| Ibritumomab Tiuxetan | Zevalin | Accel. Approv. (clinical benefit not established) treatment of patients with relapsed or refractory low-grade, follicular, or transformed B-cell non-Hodgkin's lymphoma, including patients with Rituximab refractory follicular non-Hodgkin's lymphoma. | IDEC Pharmaceuticals Corp | Feb. 19, 2002 |
| idarubicin | Idamycin | For use in combination with other approved antileukemic drugs for the treatment of acute myeloid leukemia (AML) in adults. | Adria Laboratories | Sep. 27, 1990 |
| idarubicin | Idamycin | In combination with other approved antileukemic drugs for the treatment of acute non-lymphocytic leukemia in adults. | Pharmacia & Upjohn Company | Feb. 17, 1997 |
| ifosfamide | IFEX | Third line chemotherapy of germ cell testicular cancer when used in combination with certain other approved antineoplastic agents. | Bristol-Myers Squibb | Dec. 30, 1988 |
| imatinib mesylate | Gleevec | Accel. Approv. (clinical benefit not established) Initial therapy of chronic myelogenous leukemia | Novartis | May 10, 2001 |
| imatinib mesylate | Gleevec | Accel. Approv. (clinical benefit not established) metastatic or unresectable malignant gastrointestinal stromal tumors | Novarits | Feb. 01, 2002 |
| imatinib mesylate | Gleevec | Accel. Approv. (clinical benefit not established) Initial treatment of newly diagnosed Ph+ chronic myelogenous leukemia (CML). | Novartis | Dec. 20, 2002 |
| Interferon alfa-2a | Roferon-A | | Hoffmann-La Roche Inc | Nov. 01, 1996 |
| Interferon alfa-2b | Intron A | Interferon alfa-2b, recombinant for injection is indicated as adjuvant to surgical treatment in patients 18 years of age or older with malignant melanoma who are free of disease but at high risk for systemic recurrence within 56 days of surgery. | Schering Corp | Nov. 06, 1997 |
| Interferon alfa-2b | Intron A | Interferon alfa-2b, recombinant for Injection is indicated for the initial treatment of clinically aggressive follicular Non-Hodgkin's Lymphoma in conjunction with anthracycline-containing combination chemotherapy in patients 18 years of age or older. | Schering Corp | Nov. 06, 1997 |
| Interferon alfa-2b | Intron A | Interferon alfa-2b, recombinant for Injection is indicated for intralesional treatment of selected patients 18 years of age or older with condylomata acuminata involving external surfaces of the genital and perianal areas. | Schering Corp | Nov. 06, 1997 |
| Interferon alfa-2b | Intron A | Interferon alfa-2b, recombinant for Injection is indicated for the treatment of chronic hepatitis C in patients 18 years of age or older with compensated liver disease who have a history of blood or blood-product exposure and/or are HCV antibody positive. | Schering Corp | Nov. 06, 1997 |
| Interferon alfa-2b | Intron A | Interferon alfa-2b, recombinant for Injection is indicated for the treatment of chronic hepatitis B in patients 18 years of age or older with compensated liver disease and HBV replication. | Schering Corp | Nov. 06, 1997 |
| Interferon alfa-2b | Intron A | Interferon alfa-2b, recombinant for Injection is indicated for the treatment of patients 18 years of age or older with hairy cell leukemia. | Schering Corp | Nov. 06, 1997 |
| Interferon alfa-2b | Intron A | Interferon alfa-2b, recombinant for Injection is indicated for the treatment of selected patients 18 years of age or older with AIDS-Related Kaposi's Sarcoma. The likelihood of response to INTRON A therapy is greater in patients who are without systemic symptoms, who have limited lymphadenopathy and who have a relatively intact immune system as indicated by total CD4 count. | Schering Corp | Nov. 06, 1997 |
| Interferon alfa-2b | Intron A | | Schering Corp | Jun. 21, 2002 |
| Interferon alfa-2b | Intron A | | Schering Corp | Jun. 21, 2002 |
| Interferon alfa-2b | Intron A Intron A | | Schering Corp | Jun. 21, 2002 |

| | | | | |
|---|---|---|---|---|
| irinotecan | Camptosar | Accel. Approv. (clinical benefit subsequently established) Treatment of patients with metastatic carcinoma of the colon or rectum whose disease has recurred or progressed following 5-FU-based therapy. | Pharmacia & Upjohn Company | Jun. 14, 1996 |
| irinotecan | Camptosar | Follow up of treatment of metastatic carcinoma of the colon or rectum whose disease has recurred or progressed following 5-FU-based therapy. | Pharmacia & Upjohn Company | Oct. 22, 1998 |
| irinotecan | Camptosar | For first line treatment n combination with 5-FU/leucovorin of metastatic carcinoma of the colon or rectum. | Pharmacia & Upjohn Company | Apr. 20, 2000 |
| letrozole | Femara | Treatment of advanced breast cancer in postmenopausal women. | Novartis | Jul. 25, 1997 |
| letrozole | Femara | First-line treatment of postmenopausal women with hormone receptor positive or hormone receptor unknown locally advanced or metastatic breast cancer. | Novartis | Jan. 10, 2001 |
| letrozole | Femara | | Novartis | Jan. 17, 2003 |
| leucovorin | Wellcovorin, Leucovorin | Leucovorin calcium is indicated fro use in combination with 5-fluorouracil to prolong survival in the palliative treatment of patients with advanced colorectal cancer. | Immunex Corporation | Jun. 20, 1952 |
| leucovorin | Leucovorin | | Immunex Corporation | Jan. 30, 1987 |
| leucovorin | Leucovorin | | Immunex Corporation | Jan. 30, 1987 |
| leucovorin | Leucovorin | | Immunex Corporation | Aug. 31, 1988 |
| leucovorin | Leucovorin | In combination with fluorouracil to prolong survival in the palliative treatment of patients with advanced colorectal cancer. | Lederle Laboratories | Dec. 12, 1991 |
| levamisole | Ergamisol | Adjuvant treatment in combination with 5-fluorouracil after surgical resection in patients with Dukes' Stage C colon cancer. | Janssen Research Foundation | Jun. 18, 1990 |
| lomustine, CCNU | CeeBU | | Bristol-Myers Squibb | Aug. 04, 1976 |
| mechlorethamine, nitrogen mustard | Mustargen | | Merck | Mar. 15, 1949 |
| megestrol acetate | Megace | | Bristol-Myers Squibb | Aug. 18, 1971 |
| melphalan, L-PAM | Alkeran | | GlaxoSmithKline | Jan. 17, 1964 |
| melphalan, L-PAM | Alkeran | Systemic administration for palliative treatment of patients with multiple myeloma for whom oral therapy is not appropriate. | GlaxoSmithKline | Nov. 18, 1992 |
| mercaptopurine, 6-MP | Purinethol | | GlaxoSmithKline | Sep. 11, 1953 |
| mesna | Mesnex | Prevention of ifosfamide-induced hemorrhagic cystitis | Asta Medica | Dec. 30, 1988 |
| methotrexate | Methotrexate | | Lederle Laboratories | Dec. 07, 1953 |
| methotrexate | Methotrexate | | Lederle Laboratories | Aug. 10, 1959 |
| methotrexate | Methotrexate | | Lederle Laboratories | Nov. 01, 1971 |
| methotrexate | Methotrexate | | Lederle Laboratories | Nov. 01, 1971 |
| methotrexate | Methotrexate | osteosarcoma | Lederle Laboratories | Apr. 07, 1988 |
| methotrexate | Methotrexate | | Lederle Laboratories | Oct. 31, 1988 |
| methoxsalen | Uvadex | For the use of UVADEX with the UVAR Photopheresis System in the palliative treatment of the skin manifestations of cutaneous T-cell lymphoma (CTCL) that is unresponsive to other forms of treatment. | Therakos | Feb. 25, 1999 |

| | | -continued | | |
|---|---|---|---|---|
| mitomycin C | Mutamycin | | Bristol-Myers Squibb | May 28, 1974 |
| mitomycin C | Mitozytrex | therapy of disseminated adenocarcinoma of the stomach or pancreas in proven combinations with other approved chemotherapeutic agents and as palliative treatment when other modalities have failed. | Supergen | Nov. 14, 2002 |
| mitotane | Lysodren | | Bristol-Myers Squibb | Jul. 08, 1970 |
| mitoxantrone | Novantrone | For use in combination with corticosteroids as initial chemotherapy for the treatment of patients with pain related to advanced hormone-refractory prostate cancer. | Immunex Corporation | Nov. 13, 1996 |
| mitoxantrone | Novantrone | For use with other approved drugs in the initial therapy for acute nonlymphocytic leukemia (ANLL) in adults. | Lederle Laboratories | Dec. 23, 1987 |
| nandrolone phenpropionate | Durabolin-50 | | Organon | Oct. 30, 1959 |
| Nofetumomab | Verluma | | Boehringer Ingelheim Pharma KG (formerly Dr. Karl Thomae GmbH) | Aug. 20, 1996 |
| Oprelvekin | Neumega | | Genetics Institute, Inc | Nov. 25, 1997 |
| Oprelvekin | Neumega | | Genetics Institute, Inc | Sep. 18, 2002 |
| Oprelvekin | Neumega | Neumega is indicated for the prevention of severe thrombocytopenia and the reduction of the need for platelet transfusions following myelosuppressive chemotherapy in adult patients with nonmyeloid malignancies who are at high risk of severe thrombocytopenia. | Genetics Institute, Inc | Sep. 18, 2002 |
| oxaliplatin | Eloxatin | Accel. Approv. (clinical benefit not established) in combination with infusional 5-FU/LV, is indicated for the treatment of patients with metastatic carcinoma of the colon or rectum whose disease has recurred or progressed during or within 6 months of completion of first line therapy with the combination of bolus 5-FU/LV and irinotecan. | Sanofi Synthelabo | Aug. 09, 2002 |
| paclitaxel | Paxene | treatment of advanced AIDS-related Kaposi's sarcoma after failure of first line or subsequent systemic chemotherapy | Baker Norton Pharmaceuticals, Inc | Dec. 24, 1997 |
| paclitaxel | Taxol | Treatment of patients with metastatic carcinoma of the ovary after failure of first-line or subsequent chemotherapy. | Bristol-Myers Squibb | Dec. 29, 1992 |
| paclitaxel | Taxol | Treatment of breast cancer after failure of combination chemotherapy for metastatic disease or relapse within 6 months of adjuvant chemotherapy. Prior therapy should have included an anthracycline unless clinically contraindicated. | Bristol-Myers Squibb | Apr. 13, 1994 |
| paclitaxel | Taxol | New dosing regimen for patients who have failed initial or subsequent chemotherapy for metastatic carcinoma of the ovary | Bristol-Myers Squibb | Jun. 22, 1994 |
| paclitaxel | Taxol | second line therapy for AIDS related Kaposi's sarcoma. | Bristol-Myers Squibb | Aug. 04, 1997 |
| paclitaxel | Taxol | For first-line therapy for the treatment of advanced carcinoma of the ovary in combination with cisplatin. | Bristol-Myers Squibb | Apr. 09, 1998 |
| paclitaxel | Taxol | for use in combination with cisplatin, for the first-line treatment of non-small cell lung cancer in patients who are not candidates for potentially curative surgery and/or radiation therapy. | Bristol-Myers Squibb | Jun. 30, 1998 |
| paclitaxel | Taxol | For the adjuvant treatment of node-positive breast cancer administered sequentially to standard doxorubicin-containing combination therapy. | Bristol-Myers Squibb | Oct. 25, 1999 |
| paclitaxel | Taxol | First line ovarian cancer with 3 hour infusion. | Bristol-Myers Squibb | Jun. 20, 2000 |
| pamidronate | Aredia | Treatment of osteolytic bone metastases of breast cancer in conjunction with standard antineoplastic therapy. | Novartis | Sep. 22, 1998 |
| pegademase | Adagen (Pegademase Bovine) | Enzyme replacement therapy for patients with severe combined immunodeficiency asa result of adenosine deaminase deficiency. | Enzon | Mar. 21, 1990 |
| Pegaspargase | Oncaspar | | Enzon, Inc | Feb. 01, 1994 |
| Pegfilgrastim | Neulasta | Neulasta is indicated to decrease the incidence of infection, as manifested by febrile neutropenia, in patients with non-myeloid malignancies receiving myelosuppressive anti-cancer drugs | Amgen, Inc | Jan. 31, 2002 |

| | | -continued | | |
|---|---|---|---|---|
| | | associated with a clinically significant incidence of febrile neutropenia. | | |
| pentostatin | Nipent | Single agent treatment for adult patients with alpha interferon refractory hairy cell leukemia. | Parke-Davis Pharmaceutical Co. | Oct. 11, 1991 |
| pentostatin | Nipent | Single-agent treatment for untreated hairy cell leukemia patients with active disease as defined by clinically significant anemia, neutropenia, thrombocytopenia, or disease-related symptoms. (Supplement for front-line therapy.) | Parke-Davis Pharmaceutical Co. | Sep. 29, 1993 |
| pipobroman | Vercyte | | Abbott Labs | Jul. 01, 1966 |
| plicamycin, mithramycin | Mithracin | | Pfizer Labs | May 05, 1970 |
| porfimer sodium | Photofrin | For use in photodynamic therapy (PDT) for palliation of patients with completely obstructing esophageal cancer, or patients with partially obstructing esophageal cancer who cannot be satisfactorily treated with ND-YAG laser therapy. | QLT Phototherapeutics Inc. | Dec. 27, 1995 |
| porfimer sodium | Photofrin | For use in photodynamic therapy for treatment of microinvasive endobronchial nonsmall cell lung cancer in patients for whom surgery and radiotherapy are not indicated. | QLT Phototherapeutics Inc. | Jan. 09, 1998 |
| porfimer sodium | Photofrin | For use in photodynamic therapy (PDT) for reduction of obstructing and palliation of symptoms in patients with completely or partially obstructing endobroncial nonsmall cell lung cancer (NSCLC). | QLT Phototherapeutics Inc. | Dec. 22, 1998 |
| procarbazine | Matulane | | Sigma Tau Pharms | Jul. 22, 1969 |
| quinacrine | Atabrine | | Abbott Labs | Dec. 07, 1964 |
| Rasburicase | Elitek | ELITEK is indicated for the initial management of plasma uric acid levels in pediatric patients with leukemia, lymphoma, and solid tumor malignancies who are receiving anti-cancer therapy expected to result in tumor lysis and subsequent elevation of plasma uric acid. | Sanofi-Synthelabo, Inc | Jul. 12, 2002 |
| Rituximab | Rituxan | | Genentech, Inc | Nov. 26, 1997 |
| Sargramostim | Prokine | | Immunex Corp | Nov. 07, 1996 |
| streptozocin | Zanosar | Antineoplastic agent. | Pharmacia & Upjohn Company | May 07, 1982 |
| talc | Sclerosol | For the prevention of the recurrence of malignant pleural effusion in symptomatic patients. | Bryan | Dec. 24, 1997 |
| tamoxifen | Nolvadex | | AstraZeneca Pharmaceuticals | Dec. 30, 1977 |
| tamoxifen | Nolvadex | As a single agent to delay breast cancer recurrence following total mastectomy and axillary dissection in postmenopausal women with breast cancer (T1-3, N1, M0) | AstraZeneca Pharmaceuticals | Dec. 03, 1986 |
| tamoxifen | Nolvadex | For use in premenopausal women with metastatic breast cancer as an alternative to oophorectomy or ovarian irradiation | AstraZeneca Pharmaceuticals | Mar. 16, 1989 |
| tamoxifen | Nolvadex | For use in women with axillary node-negative breast cancer adjuvant therapy. | AstraZeneca Pharmaceuticals | Jun. 21, 1990 |
| tamoxifen | Nolvadex | Metastatic breast cancer in men. | AstraZeneca Pharmaceuticals | Apr. 01, 1993 |
| tamoxifen | Nolvadex | Equal bioavailability of a 20 mg Nolvadex tablet taken once a day to a 10 mg Nolvadex tablet taken twice a day. | AstraZeneca Pharmaceuticals | Mar. 21, 1994 |
| tamoxifen | Nolvadex | to reduce the incidence of breast cancer in women at high risk for breast cancer | AstraZeneca Pharmaceuticals | Oct. 29, 1998 |
| tamoxifen | Nolvadex | In women with DCIS, following breast surgery and radiation, Nolvadex is indicated to reduce the risk of invasive breast cancer. | AstraZeneca Pharmaceuticals | Jun. 29, 2000 |
| temozolomide | Temodar | Accel. Approv. (clinical benefit not established) Treatment of adult patients with refractory anaplastic astrocytoma, i.e., patients at first relapse with disease progression on a nitrosourea and procarbazine containing regimen | Schering | Aug. 11, 1999 |
| teniposide, VM-26 | Vumon | In combination with other approved anticancer agents for induction therapy in patients with refractory childhood acute lymphoblastic leukemia (all). | Bristol-Myers Squibb | Jul. 14, 1992 |

-continued

| | | | | |
|---|---|---|---|---|
| testolactone | Teslac | | Bristol-Myers Squibb | Jun. 03, 1969 |
| testolactone | Teslac | | Bristol-Myers Squibb | May 27, 1970 |
| thioguanine, 6-TG | Thioguanine | | GlaxoSmithKline | Jun. 18, 1966 |
| thiotepa | Thioplex | | Immunex Corporation | Mar. 09, 1959 |
| thiotepa | Thioplex | | Immunex Corporation | Dec. 22, 1994 |
| thiotepa | Thioplex | | Lederle Laboratories | Aug. 15, 1990 |
| topotecan | Hycamtin | Treatment of patients with metastatic carcinoma of the ovary after failure of initial or subsequent chemotherapy. | GlaxoSmithKline | May 28, 1996 |
| topotecan | Hycamtin | Treatment of small cell lung cancer sensitive disease after failure of first-line chemotherapy. In clinical studies submitted to support approval, sensitive disease was defined as disease responding to chemotherapy but subsequently progressing at least 60 days (in the phase 3 study) or at least 90 days (in the phase 2 studies) after chemotherapy | GlaxoSmithKline | Nov. 30, 1998 |
| toremifene | Fareston | Treatment of advanced breast cancer in postmenopausal women. | Orion Corp. | May 29, 1997 |
| Tositumomab | Bexxar | Accel. Approv. (clinical benefit not established) Treatment of patients with CD20 positive, follicular, non-Hodgkin's lymphoma, with and without transformation, whose disease is refractory to Rituximab and has relapsed following chemotherapy | Corixa Coporation | Jun. 27, 2003 |
| Trastuzumab | Herceptin | HERCEPTIN as a single agent is indicated for the treatment of patients with metastatic breast cancer whose tumors overexpress the HER2 protein and who have received one or more chemotherapy regimens for their metastatic disease. | Genentech, Inc | Sep. 25, 1998 |
| Trastuzumab | Herceptin | Herceptin in combination with paclitaxel is indicated for treatment of patients with metastatic breast cancer whose tumors overexpress the HER-2 protein and had not received chemotherapy for their metastatic disease | Genentech, Inc | Feb. 09, 2000 |
| Trastuzumab | Herceptin | | Genentech, Inc | Dec. 11, 2001 |
| Trastuzumab | Herceptin | | Genentech, Inc | Aug. 28, 2002 |
| Trastuzumab | Herceptin | | Genentech, Inc | Aug. 28, 2002 |
| tretinoin, ATRA | Vesanoid | Induction of remission in patients with acute promyelocytic leukemia (APL) who are refractory to or unable to tolerate anthracycline based cytotoxic chemotherapeutic regimens. | Roche | Nov. 22, 1995 |
| Uracil Mustard | Uracil Mustard Capsules | | Roberts Labs | Sep. 13, 1962 |
| valrubicin | Valstar | For intravesical therapy of BCG-refractory carcinoma in situ (CIS) of the urinary bladder in patients for whom immediate cystectomy would be associated with unacceptable morbidity or mortality. | Anthra -> Medeva | Sep. 25, 1998 |
| vinblastine | Velban | | Eli Lilly | Nov. 05, 1965 |
| vincristine | Oncovin | | Eli Lilly | Jul. 10, 1963 |
| vincristine | Oncovin | | Eli Lilly | Jul. 10, 1963 |
| vincristine | Oncovin | | Eli Lilly | Jul. 10, 1963 |
| vincristine | Oncovin | | Eli Lilly | Jul. 10, 1963 |
| vincristine | Oncovin | | Eli Lilly | Jul. 10, 1963 |

| | | -continued | | |
|---|---|---|---|---|
| vincristine | Oncovin | | Eli Lilly | Jul. 10, 1963 |
| vincristine | Oncovin | | Eli Lilly | Jul. 10, 1963 |
| vinorelbine | Navelbine | Single agent or in combination with cisplatin for the first-line treatment of ambulatory patients with unresectable, advanced non-small cell lung cancer (NSCLC). | GlaxoSmithKline | Dec. 23, 1994 |
| vinorelbine | Navelbine | Navelbine is indicated as a single agent or in combination with cisplatin for the first-line treatment of ambulatory patients with unreseactable, advanced non-small cell lung cancer (NSCLC). In patients with Stage IV NSCLC, Navelbine is indicated as a single agent or in combination with cisplatin. In Stage III NSCLC, Navelbine is indicated in combination with cisplatin. | GlaxoSmithKline | Nov. 05, 2002 |
| zoledronate | Zometa | the treatment of patients with multiple myeloma and patients with documented bone metastases fmm solid tumors, in conjunction with standard antineoplastic therapy. Prostate cancer should have progressed after treatment with at least one hormonal therapy | Novartis | Feb. 22, 2002 |

XV. VACCINE AND OTHER PHARMACEUTICAL COMPOSITIONS AND ADMINISTRATION

A. Vaccines

The present invention includes methods for preventing or ameliorating therapy-resistant hyperproliferative disease. As such, the invention contemplates vaccines for use in both active and passive immunization embodiments. Immunogenic compositions, proposed to be suitable for use as a vaccine, may be prepared most readily directly from the dendritic cell comprising the self gene product or polynucleotide encoding same and are prepared for ready formulation into a desired vehicle.

Preparation of the vaccine may involve introducing nucleic acids encoding the self gene into the dendritic cell to be used as a vaccine. Vaccines comprising the dendritic cells are prepared as injectables either as liquid solutions or suspensions: solid forms suitable for solution in or suspension in liquid prior to injection may also be prepared. The preparation may also be emulsified. The active immunogenic ingredient may be mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, which are incorporated herein by reference in their entirety.

Vaccines may be conventionally administered parenterally, by injection, for example, either subcutaneously or intramuscularly. Additional formulations that are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, films, mouthwashes, sustained release formulations or powders and contain about 10% to about 95% of active ingredient, preferably about 25% to about 70%.

Typically, vaccines are administered in a manner compatible with the dosage formulation, and in such amount as will be therapeutically effective and immunogenic. The quantity to be administered depends on the subject to be treated, including the capacity of the individual's immune system to react to the composition, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection and the like. The dosage of the vaccine will depend on the route of administration and will vary according to the size and health of the subject.

In many instances, it will be desirable to have multiple administrations of the vaccine, usually not exceeding six vaccinations, more usually not exceeding four vaccinations, and preferably one or more, usually at least about three vaccinations. The vaccinations may be at two to twelve week intervals, more usually from three to five week intervals. Periodic boosters at intervals of 1-5 years, usually three years, will be desirable to maintain protective levels of the antibodies. The course of the immunization may be followed by assays for antibodies against the antigens, as described supra, U.S. Pat. Nos. 3,791,932; 4,174,384; and 3,949,064, are illustrative of these types of assays.

B. Carriers

A given composition may vary in its immunogenicity. It is often necessary therefore to boost the host immune system. Exemplary and preferred carriers are keyhole limpet hemocyanin (KLH) and bovine serum albumin (BSA). Other albumins such as ovalbumin, mouse serum albumin, or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde, and bis-biazotized benzidine.

C. Adjuvants

The immunogenicity of compositions can be enhanced by the use of non-specific stimulators of the immune response, known as adjuvants. Suitable adjuvants include all acceptable immunostimulatory compounds, such as cytokines, toxins, or synthetic compositions. Adjuvants can facilitate one or more of the following: 1) trap the antigen in the body to cause a slow release; 2) attract cells involved in the immune response to the site of administration; 3) induce proliferation or activation of immune system cells; or 4) improve the spread of the antigen throughout the subject's body.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GMCSP, BCG, aluminum hydroxide or other aluminum compound, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM), and cell wall skeleton (CWS) in a 2% squalene/Tween 80 emulsion. MHC antigens may even be used. Others adjuvants or methods are exemplified in U.S. Pat. Nos. 6,814,971; 5,084,269; 6,656,462, each of which is incorporated herein by reference.

Various methods of achieving adjuvant affect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin-treated (Fab) antibodies to albumin; mixture with bacterial cells (e.g., *C. parvum*), endotoxins or lipopolysaccharide components of Gram-negative bacteria; emulsion in physiologically acceptable oil vehicles (e.g., mannide mono-oleate (Aracel A)); or emulsion with a 20% solution of a perfluorocarbon (Fluosol-DA®) used as a block substitute may also be employed to produce an adjuvant effect.

Exemplary, often preferred adjuvants include complete Freund's adjuvant (a non-specific stimulator of the immune response containing killed *Mycobacterium tuberculosis*), incomplete Freund's adjuvants, and aluminum hydroxide.

In addition to adjuvants, it may be desirable to coadminister biologic response modifiers (BRM) to enhance immune responses. BRMs have been shown to upregulate T cell immunity or downregulate suppresser cell activity. Such BRMs include, but are not limited to, Cimetidine (CIM; 1200 mg/d) (Smith/Kline, PA); or low-dose Cyclophosphamide (CYP; 300 mg/m2) (Johnson/Mead, NJ) and cytokines such as g-interferon, IL-2, or IL-12 or genes encoding proteins involved in immune helper functions, such as B-7.

D. Lipid Components and Moieties

In certain embodiments, the present invention concerns compositions comprising one or more lipids associated with a nucleic acid or a polypeptide/peptide or a dendritic cell comprising same. A lipid is a substance that is insoluble in water and extractable with an organic solvent. Compounds other than those specifically described herein are understood by one of skill in the art as lipids, and are encompassed by the compositions and methods of the present invention. A lipid component and a non-lipid may be attached to one another, either covalently or non-covalently.

A lipid may be a naturally occurring lipid or a synthetic lipid. However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

In certain embodiments, a composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or any range therebetween, of a particular lipid, lipid type, or non-lipid component such as an adjuvant, antigen, peptide, polypeptide, sugar, nucleic acid or other material disclosed herein or as would be known to one of skill in the art. In a non-limiting example, a composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a non-lipid component. Thus, it is contemplated that compositions of the present invention may comprise any of the lipids, lipid types or other components in any combination or percentage range.

E. In Vitro, Ex Vivo, or In Vivo Administration

As used herein, the term in vitro administration refers to manipulations performed on cells removed from or outside of an animal, including, but not limited to cells in culture. The term ex vivo administration refers to cells which have been manipulated in vitro, and are subsequently administered to a living animal. The term in vivo administration includes all manipulations performed within an animal.

In certain aspects of the present invention, the compositions may be administered either in vitro, ex vivo, or in vivo. U.S. Pat. Nos. 4,690,915 and 5,199,942, both incorporated herein by reference, disclose methods for ex vivo manipulation of blood mononuclear cells and bone marrow cells for use in therapeutic applications.

XVI. KITS

Various kits may be provided as part of the present invention. A kit may comprise components to identify hyperproliferative disease and/or components to treat hyperproliferative disease, and in particular embodiments the hyperproliferative disease comprises one that is resistant to at least one cancer treatment. In particular embodiments, the kit comprises an apparatus and/or reagent(s) for collection of one or more dendritic cells from an individual in need of a therapy. The kit may also comprise an apparatus and/or reagent(s) for delivery of an expression construct to a dendritic cell. In further embodiments, the kit comprises an apparatus and/or reagent(s) for a therapy in addition to a dendritic cell comprising a self gene product expression construct, such as a chemotherapy, one or more tools for surgery, a reagent or apparatus for radiation, and so forth.

When the components of the kit are provided in one or more liquid solutions, the liquid solution preferably is an aqueous solution, with a sterile aqueous solution being particularly preferred. The components of the kit may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet outlining suggested therapies relevant to the present invention.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with sample collection, evaluation, therapy administration, and so forth. Such an instrument may be an inhalant, syringe, pipette, forceps, measured spoon, eye dropper or any such medically approved delivery vehicle, for example.

XVII. PREVENTION EMBODIMENTS

In certain aspects of the invention, the methods and compositions of the invention relate to the prevention of developing therapy-resistant hyperproliferative disease. The prevention of developing therapy-resistant hyperproliferative disease may occur before the subject has been diagnosed with cancer, after the subject has been diagnosed with cancer but before the subject has received cancer treatment, or after a subject has received cancer treatment but before resistance to the therapy has developed, for example.

"Prevention" and "preventing" are used according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking the onset of a disease or health-related condition. In certain embodiments of the present invention, the methods involving delivery a dendritic cell expressing a self gene product to prevent a disease or health-related condition in a subject. An amount of a pharmaceutical composition that is suitable to prevent a disease or condition is an amount that is known or suspected of blocking the onset of the disease or health-related condition. The invention contemplates that a dendritic cell expressing a self gene product may be provided to a subject to prevent the onset of therapy-resistant cancer or prevent an increase in the number of cancer cells that are resistant to the therapy.

XVIII. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Exemplary Advexin®-Dendritic Cell Studies

In specific embodiments, individuals with cancer are treated with methods and compositions of the present invention, such as, for example, dendritic cells comprising Advexin®. The cancer is resistant to at least one cancer treatment. The following description concerns exemplary embodiments only and may be applied to cancers other than small cell lung cancer (SCLC).

Patients with extensive stage disease (metastatic disease that has spread beyond the supraclavicular areas) may be de-bulked with chemotherapy (or surgery, or radiation, in specific embodiments), and then vaccinated with autologous dendritic cells transduced with Advexin®. Vaccines #1-3 are given every 2 weeks; patients are then staged (2 weeks after vaccine #3), and if no evidence of disease progression, are given an additional 3 vaccinations on a monthly schedule, for example.

Twenty-four patients have completed or are currently undergoing treatment. Most patients progressed during the first course of vaccinations (3 patients completed 6 vaccinations). Thus the overall response rate to vaccine therapy was 0%.

Thirteen patients received second line chemotherapy and are evaluable for response (n=9 taxol; n=2 CDDP/CPT11; n=1 topotecan; n=1 carboNVP16). Response to second line CTX was impressive with the following: 0 that were CR; 7 that were PR; 2 that were SD; and 4 that were PD, to give an overall response rate of 54%.

For these 13 evaluable patients, median survival from time of first vaccine was 9 months (Note—time from diagnosis to vaccine #1 is approx. 6 months, i.e., 15 month survival). For the 24 evaluable patients, survival from vaccine #1=8 months (Note—time from diagnosis to vaccine #1 is approx. 6 months, i.e., 14 mo survival) A predicted survival time for patients with extensive disease is 9 months (Kurup and Hanna, 2004 (median survival is 8-10 months); Neubauer et al., 2004 (median survival is 7.2 months); Thomas et al., 2001 (median survival is 38 weeks)).

Thus it appears as though the vaccine is well-tolerated and provides a significant survival advantage to patients with extensive stage disease.

For the vaccine study, a total number enrolled was 47 (up to July 2004); 22 patients were enrolled and consented but did not receive any study drug (wrong haplotype; rapidly expired etc.). Of the remaining subjects, 9/24 subjects received vaccines and have died (survival from vaccine #1 ranges 2-12 mo); the average was 6.5 months from vaccine #1.

For 5 evaluable patients, time from enrollment to death=16; 13; 10; 7; 3 months, with an average being 10 months. The response to primary CTX (n=24) was as follows: 5 that were CR; 12 that were PR; 1 that was SD; and 6 that were PD. Primary CTX was 75% patients carbo/VP16; and 25% CDDP/CPT11 (50% patients treated at Moffitt; 50% in community). Twenty four patients received vaccine: n=3 patients received 6 vaccines; 21 received 1-3 vaccines. Then, 23/24 patients progressed during or at the end of course 1 (vaccine 1-3). 1 patient was SD after 3 vaccinations and PD after 6 vaccinations. The TTP after vaccine #6 was 1 month (n=3), and the ORR to vaccine=0%. In platinum-refractory patients, RR to second CTX was 10%, wherein 13 patients received second line CTX; and ORR to second line CTX was 54%.

Example 2

Exemplary Small Cell Lung Cancer Embodiment of the Invention

Although the methods and compositions of the invention are applicable to a variety of cancer types, in a specific and exemplary embodiment of the invention they are employed for treatment of small cell lung cancer (SCLC), which accounts for 20% of all lung cancers. SCLC is the most aggressive of any pulmonary tumor, with a 5-year survival rate of <5%. Without treatment, the median survival from diagnosis is 2-4 months.

Compared with other cell types of lung cancer, small cell carcinoma has a greater tendency to be widely disseminated by the time of diagnosis, but is much more responsive to chemotherapy and irradiation. However, the responses to therapy are generally short-lived, and disease recurrence is frequent. Platinum and etoposide combination chemotherapy remains the standard of care in SCLC, although epirubicin/cisplatin shows similar activity with slightly reduced toxicity. Triplet therapy, dose intensification, and maintenance therapy have not demonstrated meaningful survival improvements given the increased associated toxicity. In specific embodiments, treatment of limited stage disease results in median survival of 16-24 months, for example with one of more of the following: (Etoposide (VP16)/cisplatin (CDDP)/radiotherapy (XRT)/prophylactic cranial irradiation (PCI).

The disease is divided into two classes: 33% of patients present with limited stage disease, where disease is confined to the hemithorax of origin, the mediastinum, or supraclavicular lymph nodes. In limited-stage disease, median survival is 16 to 24 months. The majority (67%) of patients present with extensive stage disease, which is classified as tumors that have spread beyond the supraclavicular areas: these patients have a worse prognosis than patients with limited-stage disease. Median survival ranges from 7-9 months, however, long-term disease-free survival is rare. Both disease classes exhibit frequent recurrence after therapy. Recent studies have further classified patients with extensive disease with regards to duration of response to primary therapy: those that do not progress within 8-12 weeks of chemotherapy are considered chemo-sensitive and may be re-treated with the same class of CTX. Those who recur or progress in less than 8-12 weeks are considered CTX-resistant/refractory and require treatment with a different class of CTX.

Aggressive treatment of extensive stage disease results in median survival of 7-9 months, but there is a very poor prognosis for recurrent disease in patients who have progressed during chemotherapy (CTX), with a median survival of 2-3 months.

This example applies the methods and compositions of the present to SCLC as an example only. In particular, a review of SCLC Vaccine Phase I/II Trial in patients with extensive stage small cell lung cancer is described. A novel patient-specific treatment comprising Advexin®-treated dendritic cells is evaluated in a Phase I/II clinical trial for extensive stage SCLC. In specific embodiments of the invention, the treatment is well-tolerated. A subset of patients have received second line chemotherapy with a median survival exceeding 9 months after vaccination (Advexin®-DC vaccination is initiated 6-8 months after primary chemotherapy), indicating a survival advantage of >50% compared to historical controls.

In particular aspects, twenty-four patients with extensive stage disease have completed or are currently undergoing treatment (eight patients received their first vaccine since June 2004). Five patients demonstrated disease stabilization during the first cycle of vaccination (3 vaccine injections) and three of these have received 6 vaccinations. Two additional patients are in process to receive the second cycle of vaccine.

Of these 24 evaluable patients, nine have died, thus median survival has not yet been attained, although the projected median survival from vaccine #1 is 8+ months (the time from diagnosis to vaccine #1 is 6-8 months). Historically, the predicted survival time for patients with extensive SCLC is 7-9 months. Thus these 24 patients appear to have significantly improved survival (>14 months) compared to standard chemotherapy.

A subset of thirteen patients received second line chemotherapy and were evaluable for response (n=9 taxol; n=2 CDDP/CPT11; n=1 topotecan; n=1 carboNVP16). Response to second line CTX was impressive with 0 that were CR; 7 that were PR; 2 that were SD; and 4 that were PD, to give an overall response rate of 54%. For these 13 evaluable patients, median survival from time of first vaccine was 8+ months, wherein the time from diagnosis to vaccine #1 is 6-8 months, i.e., 14+ month survival.

In specific embodiments of the invention, the vaccine protocol is utilized in earlier disease stage patients, i.e., those with limited stage SCLC.

Historically, vaccine therapies for cancer have failed to demonstrate significant efficacy that translated into survival advantage. This is believed to be due to the local immunosupression afforded by bulky disease, and thus more recent studies have focused on use of adjuvant vaccination after debulking (surgery to remove a large portion of tumor, which is usually done in preparation of further treatment such as chemotherapy and/or radiotherapy). In this study, 5/5 patients who responded with CR to primary chemotherapy are still alive, although prolonged survival has not been observed. Of the 12 patients with PR to primary chemotherapy, 5 have died. Fifty percent (n=3) of patients with PD after first line chemotherapy are still alive. Thus, in particular embodiments of the invention, patients who respond well to primary chemotherapy demonstrate potentiation of second line chemotherapy by vaccination.

The recent Provenge Phase III trial showed a statistically significant survival benefit in patients with asymptomatic, metastatic, androgen-independent prostate cancer. Note that inclusion criteria limited patients who were asymptomatic and had Gleason scores of <7: it is likely that these patients had low-volume disease upon vaccination. The recent Biomira trial in stage IIIb NSCLC also enrolled patients who exhibited stable disease or who had responded to first line chemotherapy or radiotherapy. Study results did not support statistically improved survival in a larger group of patients with stage IIIB and stage IV disease, further suggesting that minimal residual disease is a good target.

Thus the current study indicates that the vaccine is well tolerated and provides a significant survival advantage to patients with extensive stage disease. In particular aspects of the invention, patient charts are reviewed, survival analyses are updated, and p53 immunity with survival benefit is correlated. In additional embodiments, a controlled multi-center Phase II/III study is employed to evaluate and optimize the benefit of Advexin®-DC vaccination in patients with extensive disease who have responded to first line chemotherapy.

Figure 2:
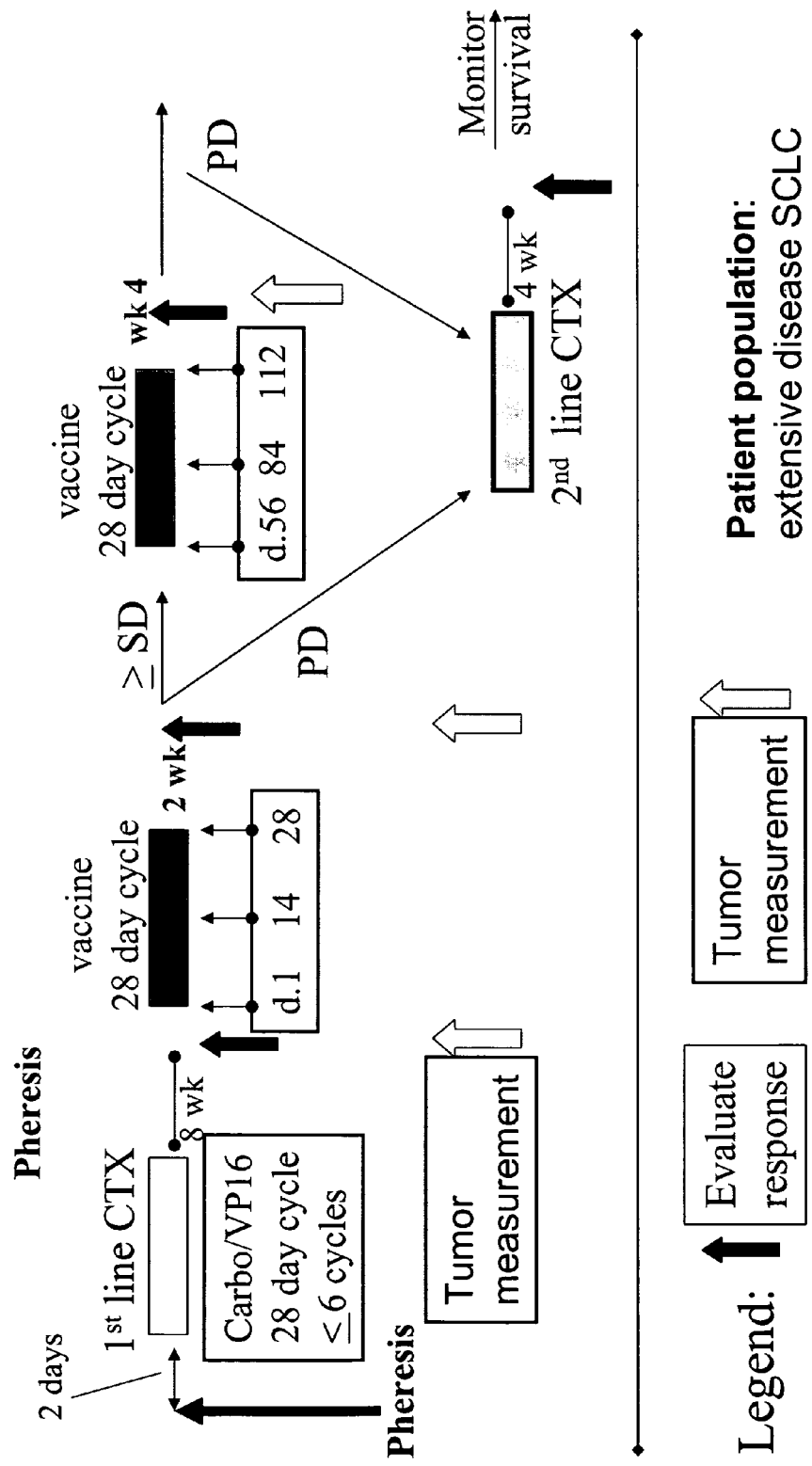
FIG. 2 provides an exemplary Advexin®-DC vaccine phase I/II trial in patients with extensive SCLC.
Figure 3:
FIG. 3 demonstrates exemplary Advexin® vaccine schema first line responses.
Figure 4:
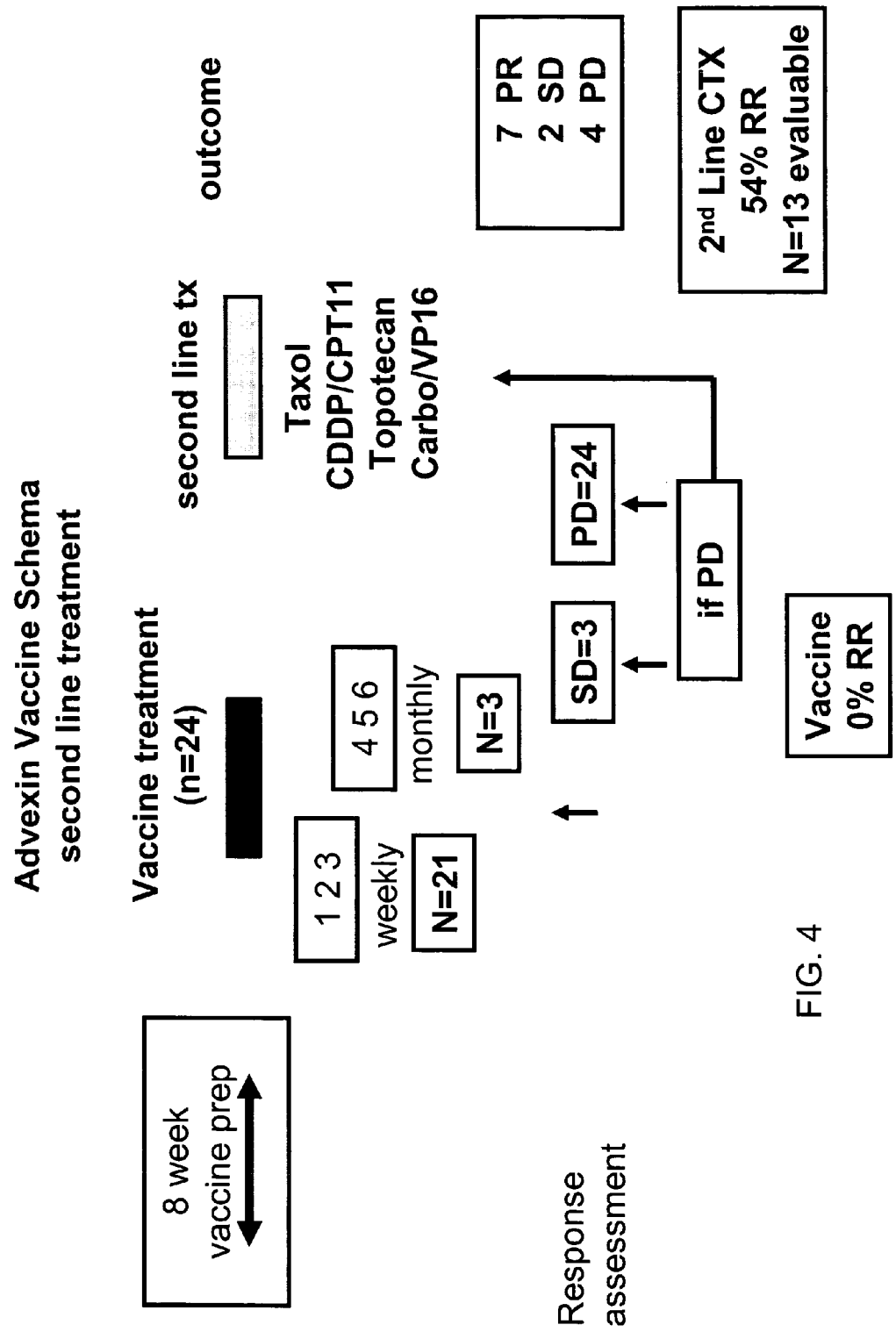
FIG. 4 shows Advexin® vaccine schema second line treatment.
Figure 5:
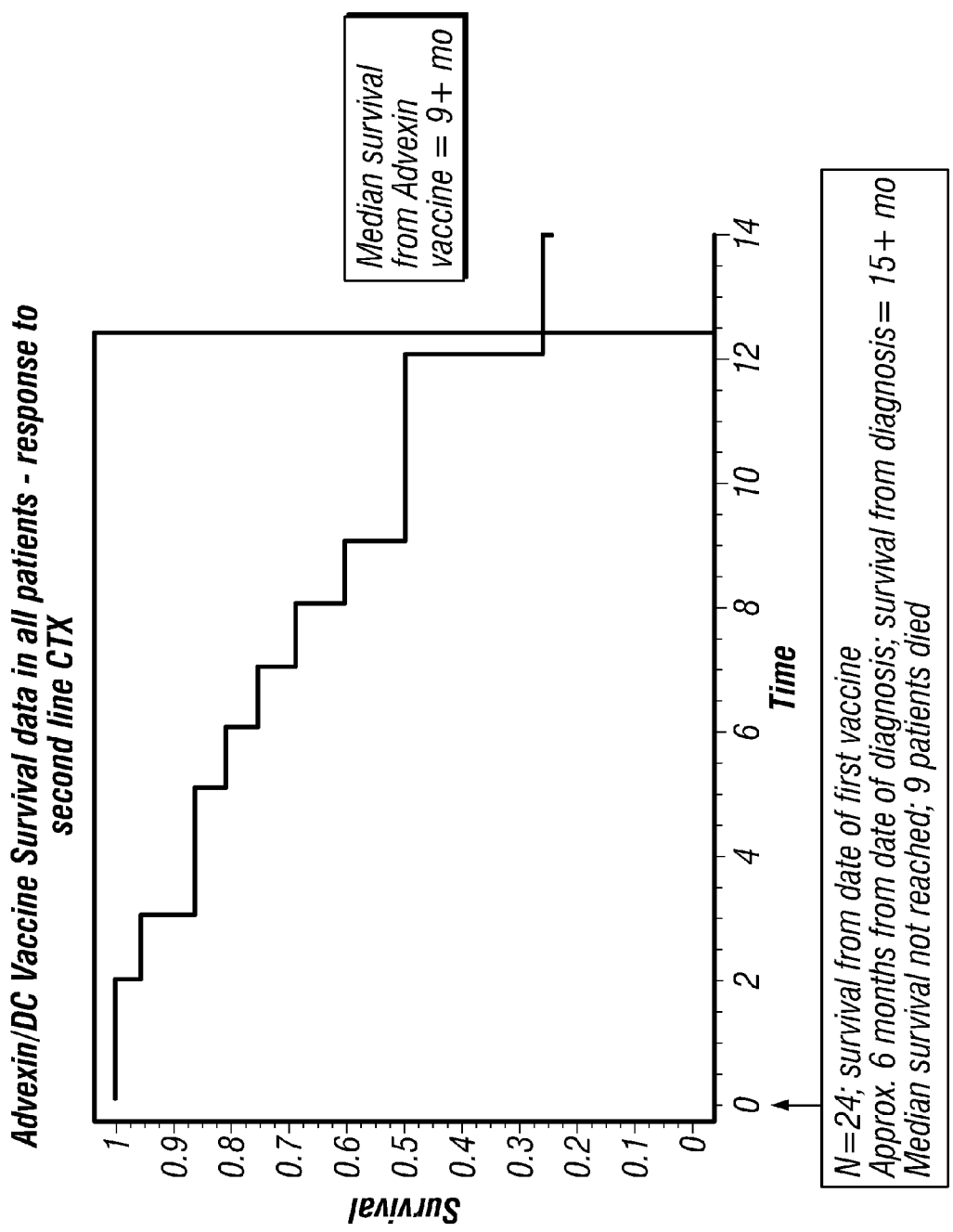
FIG. 5 shows Advexin®/DC vaccine survival data in all patients for response to second line treatment.

FIG. 1 provides an exemplary conventional SCLC treatment schema. In contrast, FIG. 2 provides an exemplary Advexin®-DC vaccine phase I/II trial in patients with extensive SCLC. FIG. 3 demonstrates exemplary Advexin® vaccine schema first line responses, whereas FIG. 4 shows Advexin® vaccine schema second line treatment. FIG. 5 shows Advexin®/DC vaccine survival data in all patients for response to second line treatment.

FIG. 6 provides a chart of response to second line chemotherapy. In particular, 13 patients were evaluable after second line CTX. TTP averaged 1.75 months after first line CTX, but a TTP<3 months defined the majority of these patients as "drug-resistant." For responses to second line CTX, 7 were PR; 2 that were SD; 4 that were PD; the overall response rate (ORR) is 54%; median survival is 9+ months from vaccine 1. Historically, median survival in drug-resistant patients is 3-6 months. For example, Taxol showed median survival of 100 days with life-threatening toxicity in 20% of patients (Smit, 1998).

FIG. 7 shows drug activity in resistant SCLC compared to that of the present invention.

Figure 8:
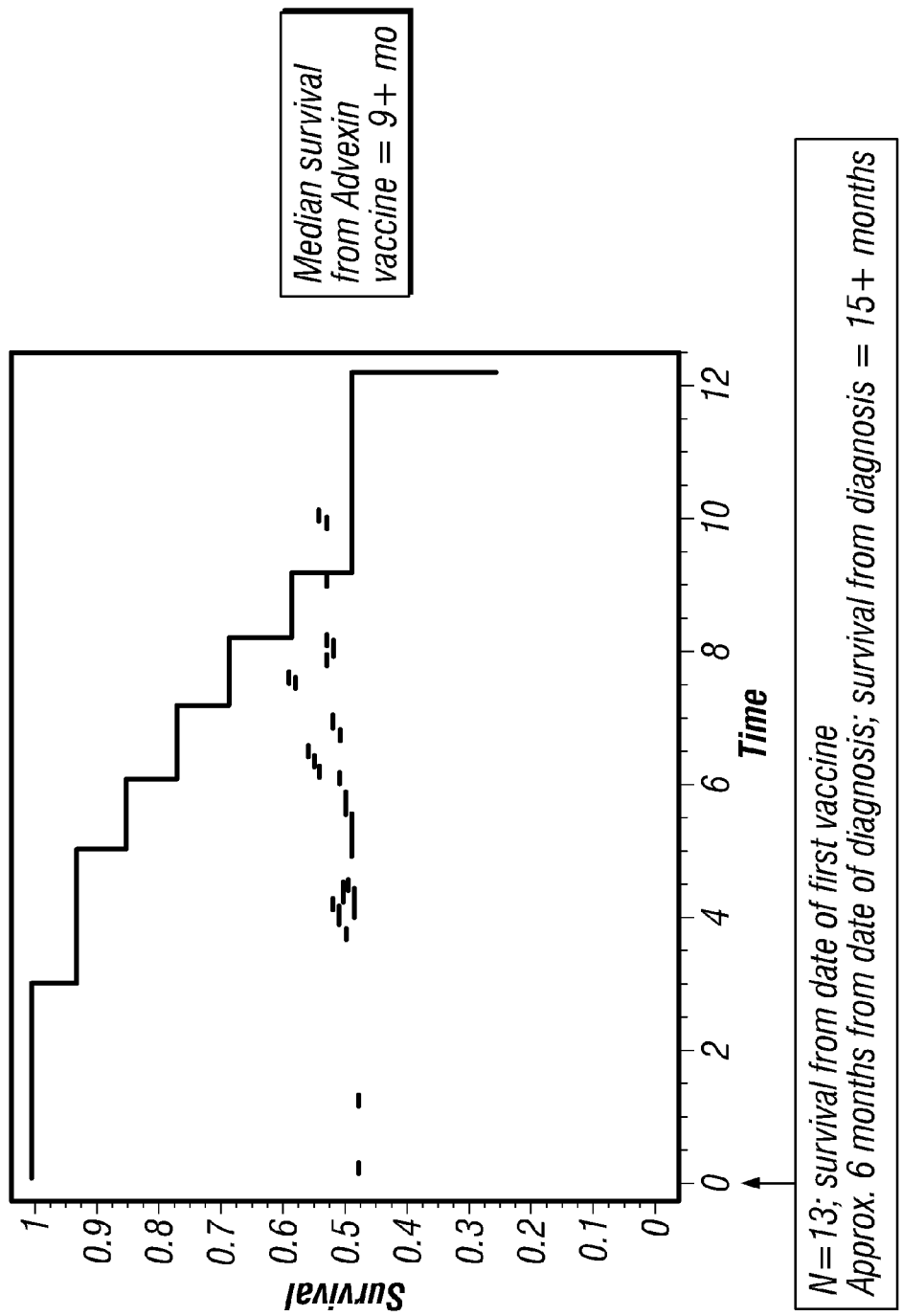
FIG. 8 shows Advexin®/DC vaccine survival data in evaluable patients receiving second line vaccine/CTX.

FIG. 8 shows Advexin®/DC vaccine survival data in evaluable patients receiving second line vaccine/CTX. Median survival from Advexin® vaccine is greater than 9 months, which is considerably longer than a median survival of 6.1 months in resistant cancer as demonstrated in Ardizzoni et al. (2003).

Figure 9:
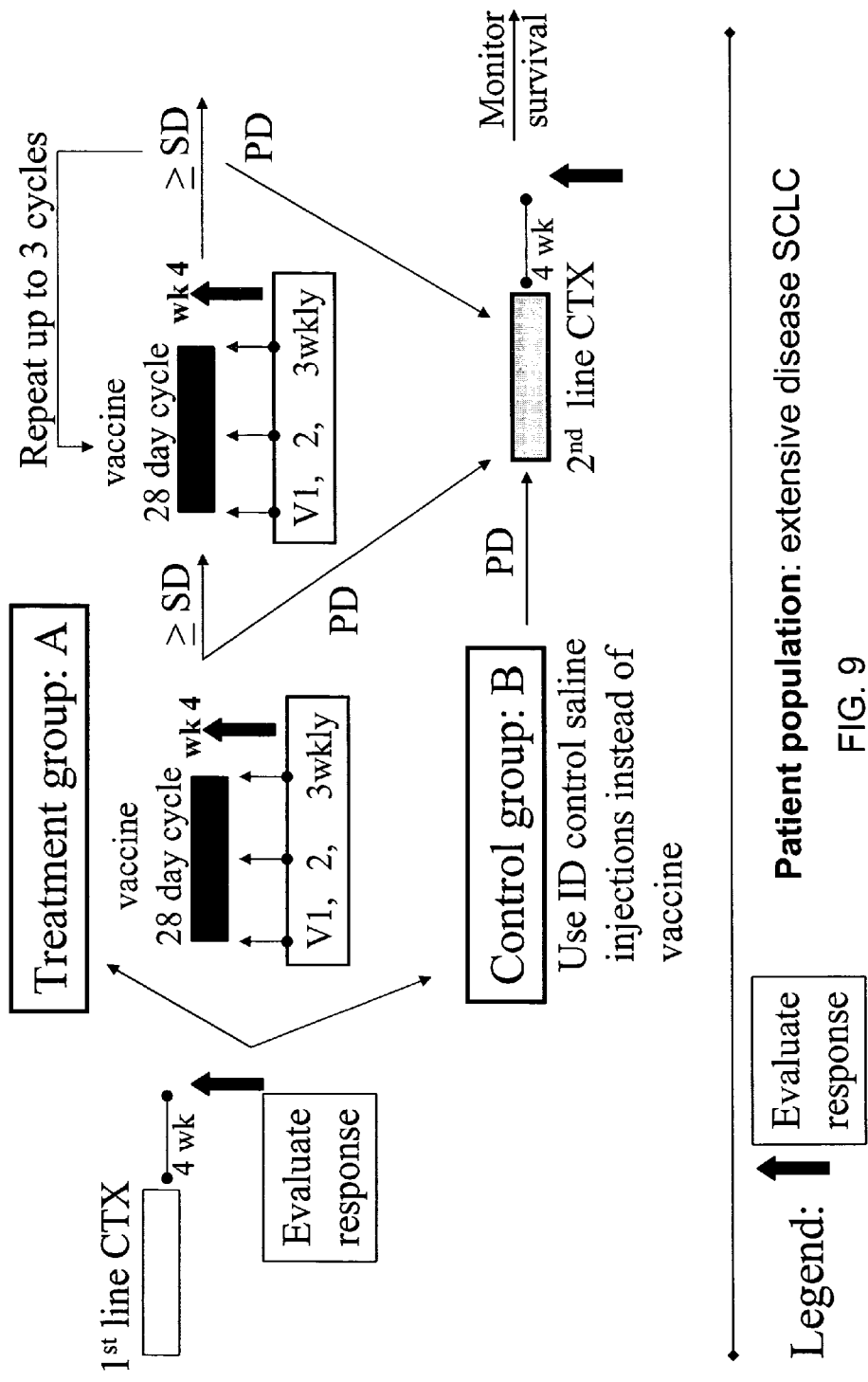
FIG. 9 provides an exemplary Advexin®-DC vaccine phase II trial in patients with extensive SCLC.

FIG. 9 provides an exemplary Advexin®-DC vaccine phase II trial in patients with extensive SCLC.

In conclusion, Advexin® therapy was well-tolerated and sensitized to second line CTX in patients with recurrent disease. In particular, Advexin® vaccine therapy provided substantial survival advantage in patients with extensive and recurrent SCLC.

Example 3

Exemplary Clinical Trial Outline

Between January 2003 and June 2005, 29 fully-evaluable patients for both immune response and clinical response were treated with the vaccine. All patients had ES SCLC at the time of vaccination (17 patients with newly diagnosed ES disease and 12 with relapsed disease; Table 4). The median age was 63 years (range 39-76). Twenty patients were vaccinated after only one prior chemotherapy regimen (six patients after two regimens, and three patietns after three regimens). All patients had received prior platinum therapy. Patient characteristics are listed in Table 4.

TABLE 4

Patient Characteristics

| | | No. | % |
|---|---|---|---|
| Total | | 29 | 100 |
| Gender | M | 13 | 45 |
| | F | 16 | 55 |
| Age | Median | | 63 |
| | Range | | 39-76 |
| Performance Status | ECOG 0-1 | 28 | 98 |
| (PS) | ECOG 2 | 1 | 2 |

TABLE 4-continued

Patient Characteristics

| | | No. | % |
|---|---|---|---|
| Clinical Stage | Extensive | 17 | 59 |
| | Relapsed | 12 | 41 |
| No. Chemo Regimens | 1 | 20 | 69 |
| Before Vaccine | 2 | 6 | 21 |
| | ≥3 | 3 | 10 |
| No. Leukophereses | 1 | 18 | 62 |
| | ≥2 | 11 | 38 |
| No. Vaccines | <3 | 1 | 3 |
| | 3 | 20 | 69 |
| | >3 | 8 | 28 |

Figure 10:
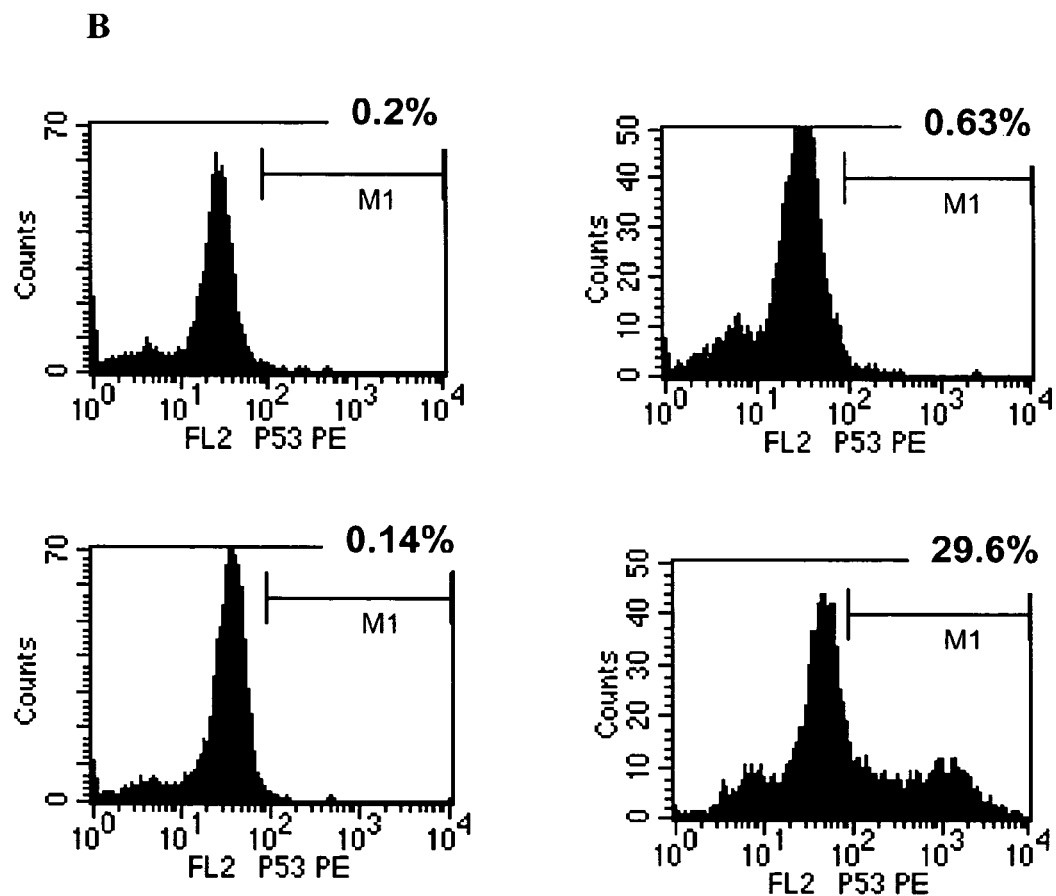
FIGS. 10A-10B show characteristics of DCs generated from mononuclear cells. DCs were prepared from frozen sample of mononuclear cells and infected with Adv-p53 as described in the text. On day 7, cells were collected and labeled with cocktail of FITC-conjugated lineage specific antibodies and PerCP conjugated HLA-DR antibody (FIG. 10A—bottom panel) or isotype control IgG (FIG. 10A—top panel). Surface staining cells were fixed, permeabilized, and stained with isotype control (FIG. 10B—right top panel) or anti-p53 antibody (FIG. 10B—right bottom panel). To illustrate specificity of the staining non-infected cells were stained with isotype control IgG (FIG. 10B—left top panel) or anti-p53 antibody (FIG. 10B—left bottom panel). Lin-HLA-DR+ cells were gated and staining with p53 was analyzed within this population of DCs.

DC were generated from peripheral blood mononuclear precursors and then infected with an adenoviral construct containing wild-type p53 (ADVEXIN®) as described in Methods. A typical example of the cell phenotype after Ad-p53 treatment is presented in FIG. 10A. The number of p53-positive DC was evaluated using flow cytometry (FIG. 10B). Patients were scheduled to receive 3 doses of vaccine with 2-week interval injected intradermally. If patients demonstrated stable disease, they were given 3 more doses of the vaccine, once per month. The total number of administered vaccines ranged from 2 to 6 (median=3) with a total of 82 vaccines administered throughout the study. The Phase I component of the trial had an initial goal to escalate vaccine dose from $5 \times 10^6$ to $5 \times 10^7$ p53+DC. However, generation of greater than $5 \times 10^6$ p53+DC per dose was difficult to achieve ($>10^7$ p53+ DC were generated in less than 10% of all cases). Therefore, to maintain consistency throughout the trial, the present inventors decided not to escalate the single dose of p53+DC to greater than $5 \times 10^6$ cells. On average, $7.7 \times 10^7$ DC and $8.6 \times 10^6$ p53+DC were generated per dose (Table 5).

TABLE 5

The number of DCs generated for vaccines

| | Total number of DCs generated per vaccine | The number of p53 + DCs generated per vaccine | The number of p53 + DCs injected per vaccine |
|---|---|---|---|
| Median | $2.42 \times 10^7$ | $4.66 \times 10^6$ | $4.78 \times 10^6$ |
| Average | $7.69 \times 10^7$ | $8.64 \times 10^6$ | $3.84 \times 10^6$ |
| Maximum | $1.59 \times 10^8$ | $2.7 \times 10^8$ | $5 \times 10^6$ |
| Minimum | $1.47 \times 10^6$ | $2.4 \times 10^5$ | $2.4 \times 10^5$ |

The number of injected p53+DC was limited to $5 \times 10^6$ even if more cells were generated. On average each patient received $3.8 \times 10^6$ p53+DC per vaccination. In 5 cases, patients received less than $10^6$ p53+DC because of difficulties in vaccine production.

Example 4

Antigen-Specific Cellular Immune Response to the Vaccine

To evaluate immunological response, samples of peripheral blood from patients were collected before immunization, 2-3 weeks after completion of 3 rounds of immunization and 2 months later. p53 specific immune response was evaluated in IFN-γ ELISPOT using canarypox virus (ALVAC) containing wild-type p53 or control virus. Use of ALVAC containing the full-length p53 gene allowed for evaluation of p53 specific response regardless of patients' HLA type. Development of an immune response to p53 was considered significant if it was at least 2 SD higher than the response to control ALVAC. Response to vaccination was considered significant if p53-specific response after immunization was more than 2 SD higher than p53-specific response before immunization and at least 2 SD higher than response to control ALVAC.

Figure 11B:
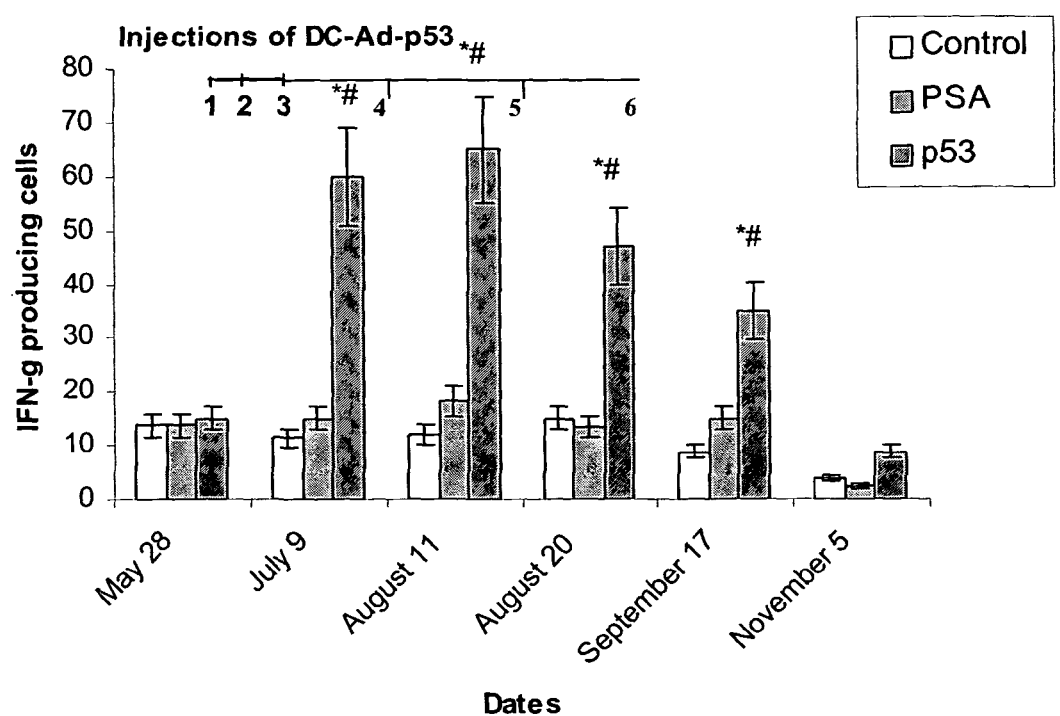
Figure 11C:
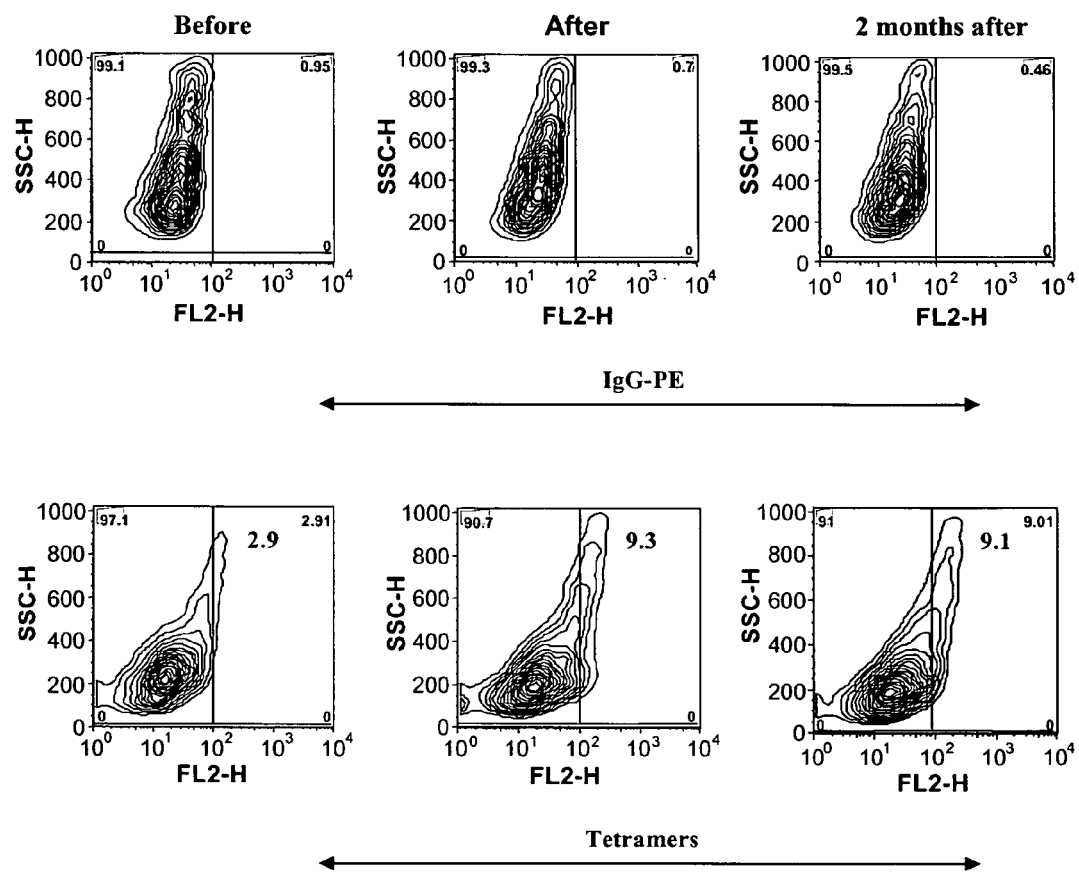

Representative ELISPOT data are shown for exemplary patients 1 and 2 (FIG. 11A). Although baseline immune reactivity against control ALVAC and p53 were lower in patient 2 than patient 1, in both cases significant immune reactivity was generated against p53 three weeks post-vaccination (p=0.045; FIG. 11A). The magnitude of the response had decreased by 2 months post-vaccine, however signals were still significantly above pre-vaccine levels. Immune response was further evaluated in a subset of 12 HLA-A2 positive patients, using HLA-A2 matched p53-derived or control peptides. Illustrative results are shown in FIG. 11B. In this patient, pre-vaccine immune reactivity was identical for control, PSA and p53 peptides. One month after vaccination, significant p53-specific reactivity was evident. The immune response was maintained during the subsequent three monthly vaccine treatments and appeared to return to baseline levels three months after the last vaccine (FIG. 11B). No induction of immune reactivity was observed against the control PSA peptide indicating the specificity of the response. Response to the p53 peptide allows for more precise evaluation of CD8+ T-cell specific responses. In these patients the presence of antigen-specific CD8+ T cells was also evaluated and confirmed using tetramer staining (FIG. 11C).

Figure 12:
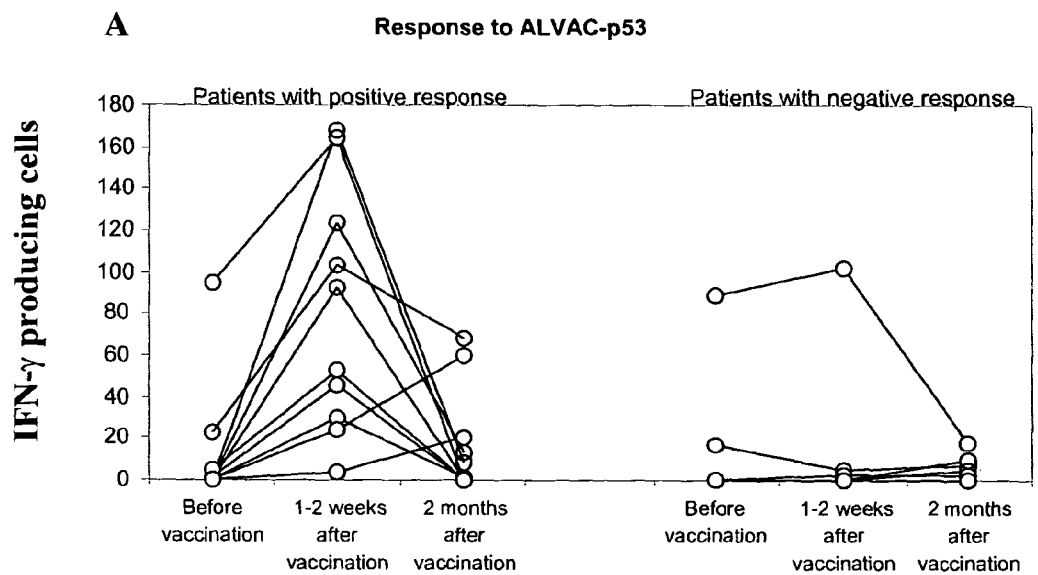
FIGS. 12A-12D show p53-specific response to vaccination. The results of IFN-γ ELISPOT assay from all tested patients are presented. The background level of non-specific IFN-γ production (ALVAC-control or irrelevant peptide) was subtracted. The number of spots per $2 \times 10^5$ cells are shown. All measurements were done in quadruplicate. Only average for each sample is shown. Not all HLA-A2 positive patients were tested both with ALVAC-p53 and p53-derived peptide.
Figure 12:
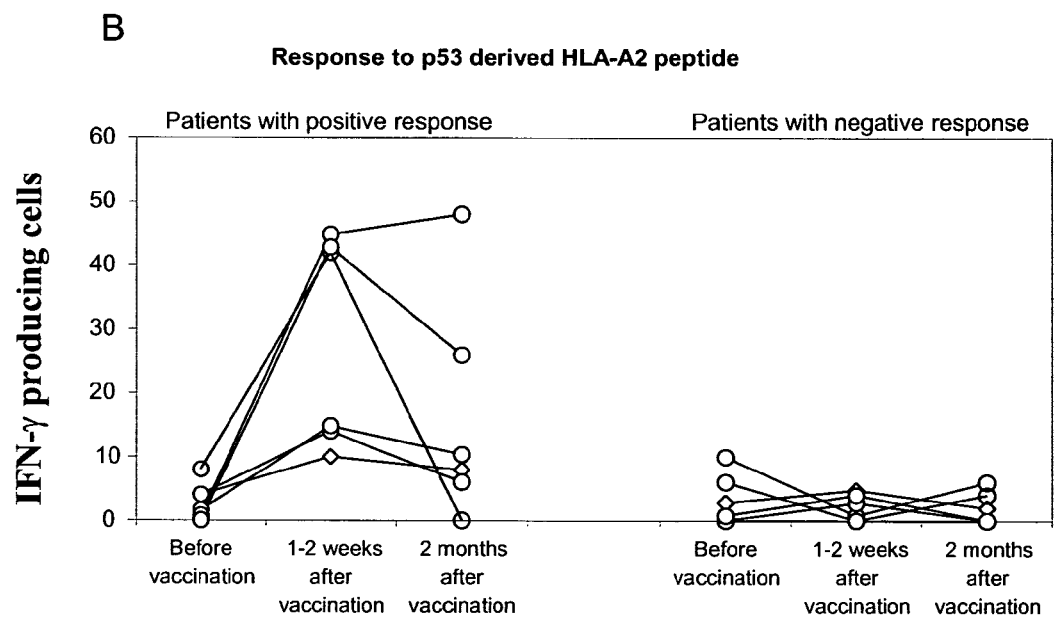
Figure 12:
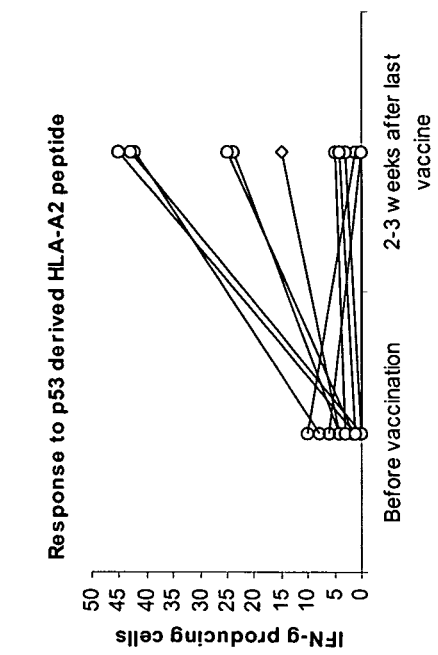

Significant p53 specific response to vaccination was found in 9 out of 19 patients (47.3%) using ALVAC-p53 and in 7 out of 12 patients (58.3%) using p53-derived peptide (FIGS. 12A and 12B). FIGS. 12C and 12D show modest but significant p53-specific T cell responses to vaccination in 13 out of 25 patients (52%) using ALVAC-p53, and in 7 out of 12 patients (58.3%) using the p53-derived peptide. Three patients who had significant response to vaccination measured using p53-derived peptide had not been tested with ALVAC-p53 due to technical reasons. Overall, 12 out of 22 tested patients (54.5%; termed p53 responders) had statistically significant p53-specific response to immunization. When both assays were tested using the same patient cells, the response rate to ALVAC-p53 compared to p53-derived peptide was not significantly different (p>0.1), however a lower response was seen using tetramer staining. Only 3 out of 11 tested patients (27.2%) demonstrated significant increase in tetramer staining (data not shown). Pre-vaccination level of p53-specific immunity was similar in patients who immunologically responded to the vaccine and those who did not (FIGS. 12A and 12B). The level of p53-specific immune response decreased dramatically 2 months after completion of vaccination. This coincided with second line chemotherapy, which started in most patients 3-4 weeks after the end of vaccination.

Example 5

Association Between Cellular and Humoral Immune Response to the Vaccine

Detectable pre-immunization level of anti-p53 antibody was observed in 10 out of 22 tested patients and only 3 patients demonstrated significant increase in the level of anti-p53 antibody after immunization. Interestingly, all those patients had detectable pre-vaccine level of the antibody. Four out of 10 patients (40%) with detectable pre-immunization level of anti-p53 antibody had positive p53-specific cellular response to vaccination, which was not statistically different from the response rate in patients with no pre-existing level of anti-p53 antibody.

Figure 13:
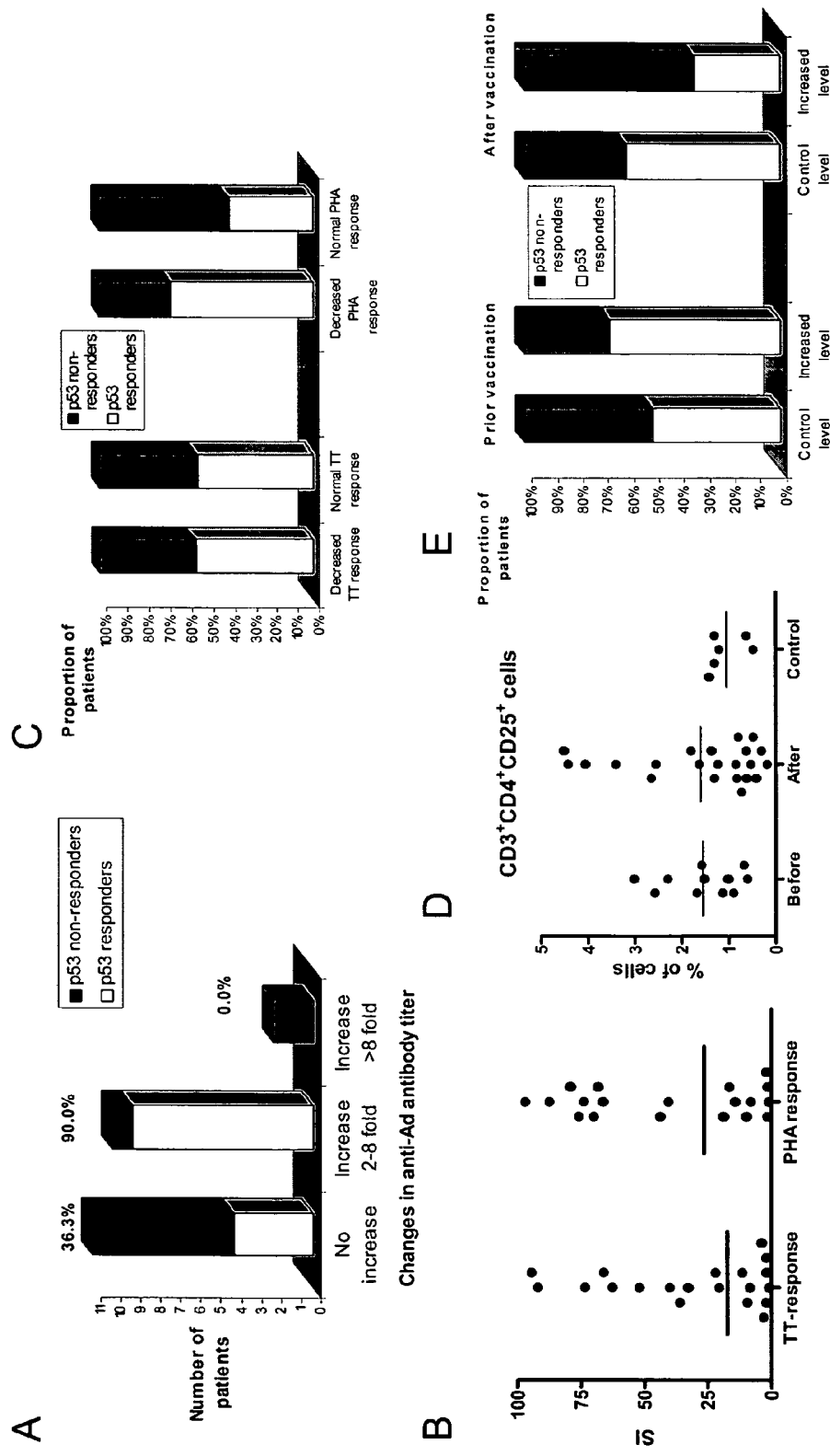
FIGS. 13A-13E show association between p53-specific cellular response, anti-adenoviral humoral response and T-cell function prior vaccination.

Anti-adenovirus antibody may play a critical role in limiting the effect of adenovirus based cancer vaccines. The present inventors measured anti-Adv IgG and IgM antibodies by ELISA using serial dilution of patients' sera. Most patients had detectable pre-immunization level of anti-Adv IgG antibody. After three rounds of immunization with Adv-p53 DC, the titer of anti-Adv antibody increased in 12 of 23 patients (52.1%). Moderate increase (>2 and <8 fold) was observed in 10 patients and substantial (>8-fold) increase in 2 patients. Both patients with substantial increase of anti-adenovirus response did not develop p53-specific cellular response to immunization. p53-specific cellular immune response to vaccination was observed in 9 out of 10 patients (90%) with moderately increased titer of anti-Adv antibody, and in only 4 out of 11 (36.3%) patients with no detectable increase in antibody titer (two-tailed p-value in Fisher's Exact Test=0.011) (FIG. 13A). Thus, moderately increased production of anti-Adv antibody in response to immunization not only did not prevent the development of a cellular p53-specific immune response to vaccination, but was associated with positive response. Anti-adenovirus antibody detected in those patients had neutralizing activity with median neutralizing titer of 1600 (data not shown).

Example 6

Association of Immune Response to Vaccination with Pre-Vaccination Level of T-Cell, DC Activity, and the Presence of Immature Myeloid Cells Generation of p53-specific cellular response may depend not only on the quality of antigen stimulation but also on the functional activity of T-cells and host antigen presenting cells, specifically DCs. The present inventors characterized the pre-existing condition of host immune system influenced the outcome of vaccination. To address this question, MNC isolated from patients prior to vaccination were stimulated with either tetanus toxoid (TT) or PHA and cell proliferation was measured by uptake of $^3$H-thymidine. The normal level of response was established using MNC from healthy volunteers and donors. Stimulation index (SI) was used to assess T cell proliferation in response to stimuli. It was calculated as the ratio between cell proliferation in the presence of 0.1 µg TT or 5 µg/ml PHA and the medium alone. In healthy donors SI for TT stimulation ranged from 15 to 80 with median of 30.4, whereas SI for PHA stimulation ranged from 25 to 90 with median 53.5. Nine out of 20 (45%) tested patients had TT response below the lower limit of normal samples and 9 out of 19 (47.3%) tested patients had PHA response below control range (FIG. 13B). However, patients with decreased T-cell response to TT or PHA developed p53-specific immunity to vaccination at the same rate as the patients with normal levels of T-cell response (FIG. 13C).

Recent studies have suggested that natural CD4+CD25+ regulatory T cells ($T_{reg}$) might play important role in down-regulation of antitumor immune response (reviewed in Chattopadhyay et al., 2005). For initial evaluation of $T_{reg}$ population we calculated the presence CD25$^{high}$ cells within the total population of CD3+CD4+ T cells. No differences in the proportion of these cells were found between group of healthy donors and SCLC patients prior vaccination or immediately after completion of vaccination (FIG. 13D). The present inventors characterized p53 specific response to vaccination in the group of patients with elevated levels of CD4$^+$CD25$^+$ T cells. However, no statistically significant link between the presence of CD3$^+$CD4$^+$CD25$^+$ cells in patients' blood before or after vaccination and p53 specific T-cell response to vaccination was observed (FIG. 13E).

Figure 14:
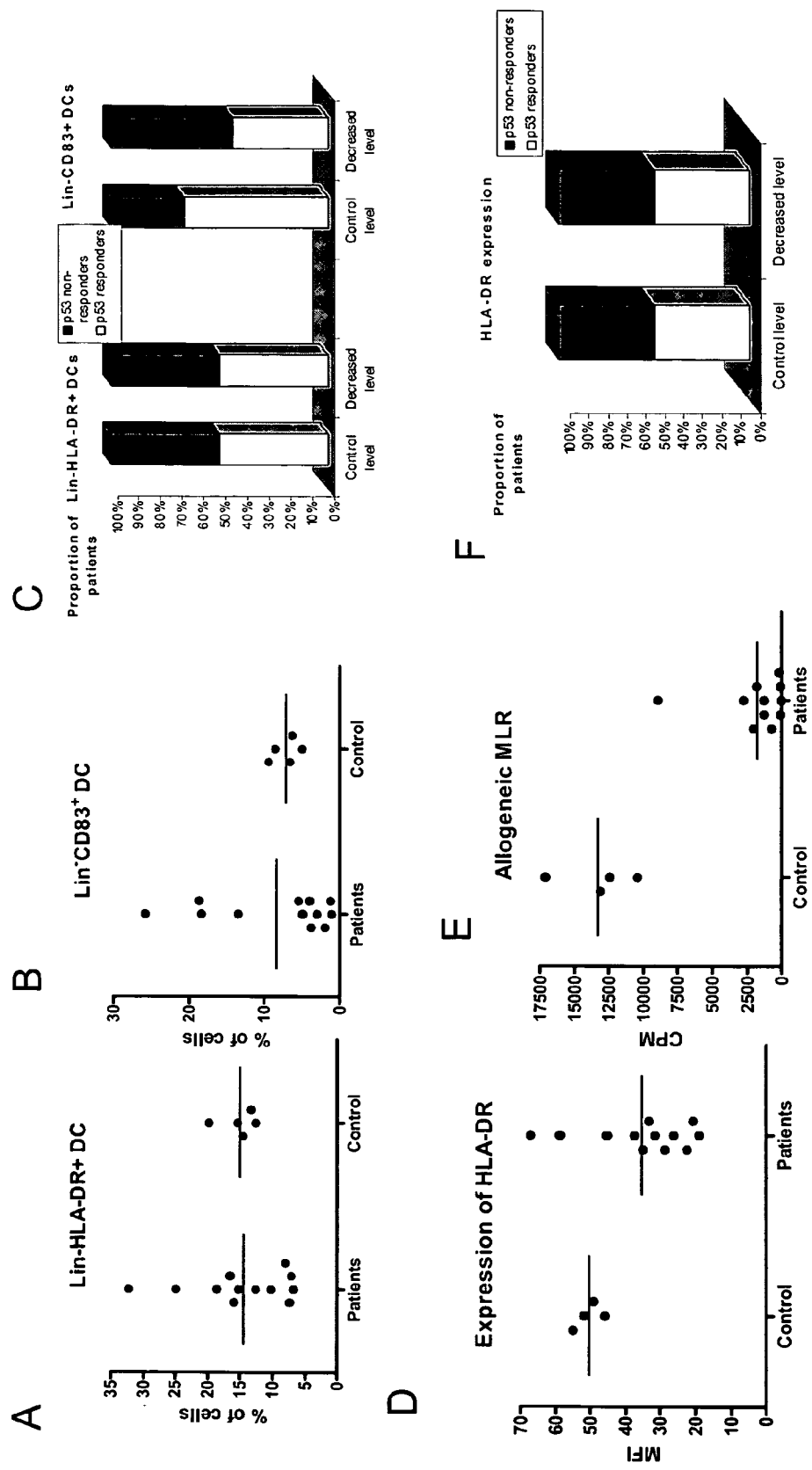
FIGS. 14A-14K show association between p53-specific response to vaccination and DC phenotype and function. MNC were isolated from control donors and SCLC patients prior vaccination. Cells were stained with cocktail of antibodies and analyzed using multicolor flow cytometry as described in Methods. The proportion of DC (Lin-HLA-DR+) (FIG. 14A), mature DCs (Lin-CD83+) (FIG. 14B), and ImC (Lin-HLA-DR-CD33+) (FIG. 14G) were evaluated. Two-tailed p values were calculated using Munn Whitney test.
Figure 14:
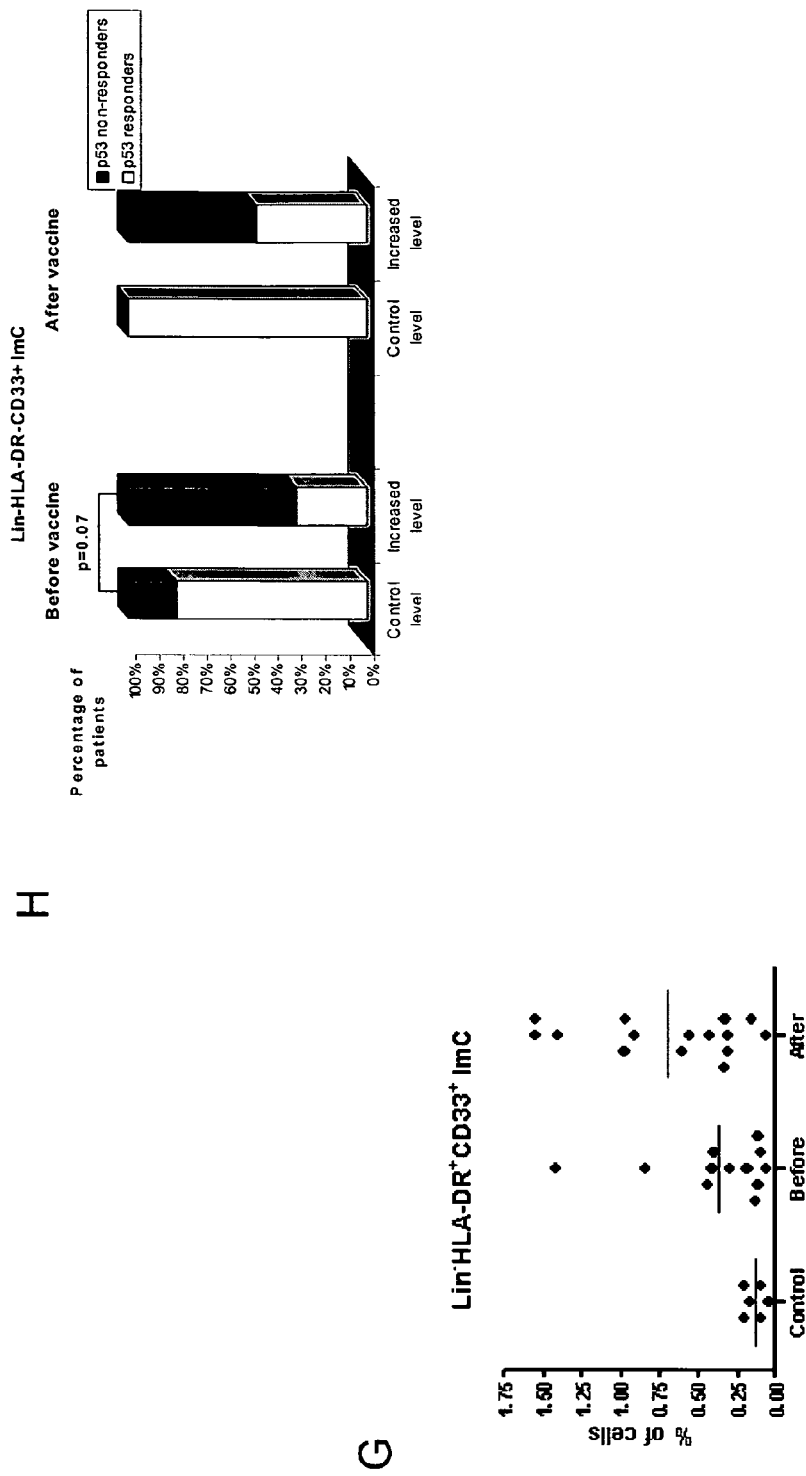
Figure 14:
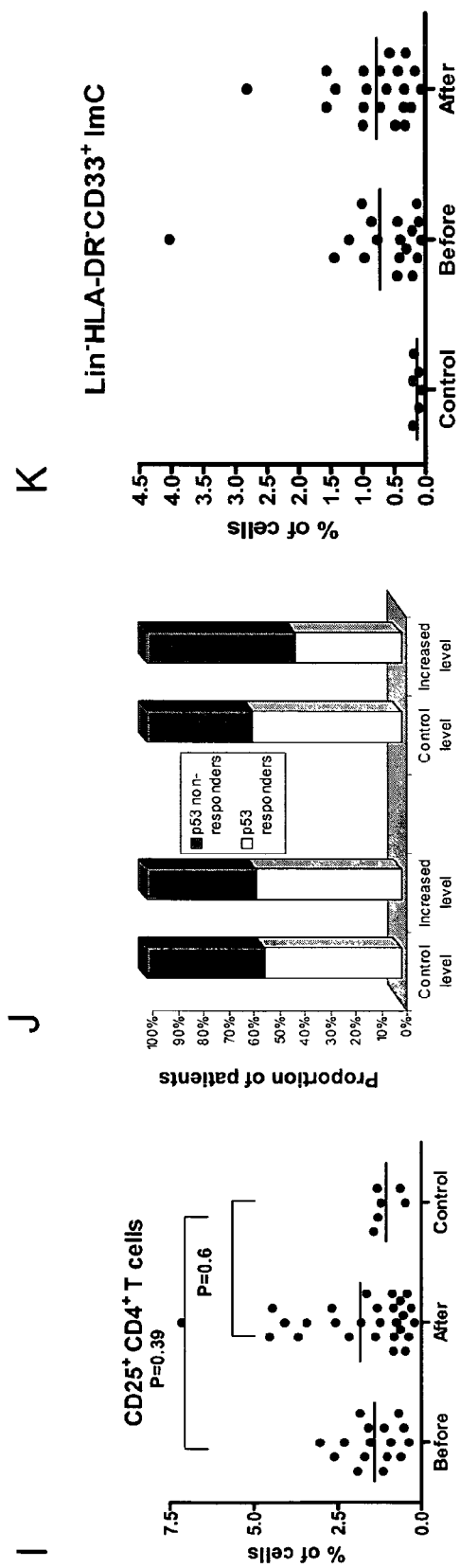

Recent studies have suggested that CD4$^+$CD25$^+$ regulatory T cells (T$_{reg}$) might play an important role in the down-regulation of antitumor immune responses (reviewed in Chattophadhyay et al., 2005). As an initial evaluation of the T$_{reg}$ population, CD25$^{high}$ cells were enumeratd within the total population of CD3$^+$CD4$^+$ T cells. No differences in the proportion of these cells were found between the groups of healthy subjects and patients with SCLC prior to vaccination or 2 to 3 weeks after completion of vaccination (FIG. 14I). Furthermore, no statistically significant link was found between the presence of these cells in the patients' blood before or after vaccination, and p53-specific T cell responses to vacination (FIG. 14J).

The present inventors characterized association between the presence and functional activity of DCs prior vaccination and antigen-specific response to vaccination. No statistically significant decrease in the proportion of DCs (Lin$^-$HLA$^-$DR$^+$) and their mature CD83+ subset was found in SCLC patients (FIGS. 14A and 14B). A substantial number of patients had decreased level of DCs. The present inventors compared the level of p53 specific immune response to vaccination in patients who had decreased proportion of DCs (below minimum values in control group) with those who had normal level of DCs. No differences were found (FIG. 14C). Expression of HLA-DR on DCs from patients with SCLC was significantly lower than in healthy donors. Mean fluorescence intensity was decreased from 50.5±1.9 in control group to 35.5±4.3 in SCLC prior vaccination (p=0.03) (FIG. 14D). Even more substantial decrease was seen in allogeneic mixed leukocyte reaction, the function specifically attributed to DCs. Proliferation of responders, allogeneic T cells, was decreased from 13279±140.7 CPM after stimulation by MNC from control group to 1740±767.4 CPM after stimulation with MNC from SCLC patients (p<0.001) (FIG. 14E). However, immunological response to vaccination (p53 specific response) was the same in groups of patients with control and decreased expression of HLA-DR (FIG. 14F). For allogeneic MLR such analysis was not possible since all patients had reduced level of this test.

Next, the present inventors evaluated the level of immature myeloid cells (ImC) implicated into immunosuppressive activity in cancer (Kusmartsev and Gabrilovich, 2002; Gabrilovich, 2004). Patients with SCLC had elevated level of Lin$^-$HLA-DR$^+$CD33$^+$ ImC prior vaccination (0.47±0.13% vs. 0.13±0.03% in control, p=0.03). After vaccination their presence increased even further to 0.70±0.13 (p=0.002) (FIG. 14G). In patients with SCLC that had Lin$^-$HLA-DR$^-$CD33$^+$ immature myeloid cells prior to vaccination, after vaccination, their presence increased even further (P=0.002) (FIG. 14K). All patients with normal level of ImC prior vaccination had developed p53 specific immune response to vaccination (100%), compared with only 25.0% of patients with elevated level of ImC (two-tail p=0.06 in Fisher's exact test) (FIG. 14H). Two patients had normal level of ImC after vaccination. Both these patients had p53 specific response comparing with 46.1% of patients with elevated level of ImC after vaccination demonstrated p53 specific immune response. Because of small sample size in a group with normal level of ImC statistical analysis of post-vaccination data was not possible. Thus, it appears that p53 specific immune response to vaccination was associated with increased presence of ImC prior vaccination. Because of small sample size statistical analysis of post-vaccination data was not possible.

Example 7

Clinical Response to Vaccination and its Association with Antigen-Specific Immune Response Toxicities associated with the administration of the vaccine were infrequent and mostly mild. Only 2 patients experienced grade 2 toxicities (1 fatigue, 1 arthralgia) with vaccine administration, and vaccinations were never withheld due to the presence of any toxicity. The most frequently noted toxicities were: grade 1 arthralgia/myalgia (9 pts.), fatigue and erythema at the site of vaccination (5 pts. each) and pain at the site of vaccination (4 pts.). The occurrence of toxicities was independent of the number of vaccines previously received.

Figure 15:
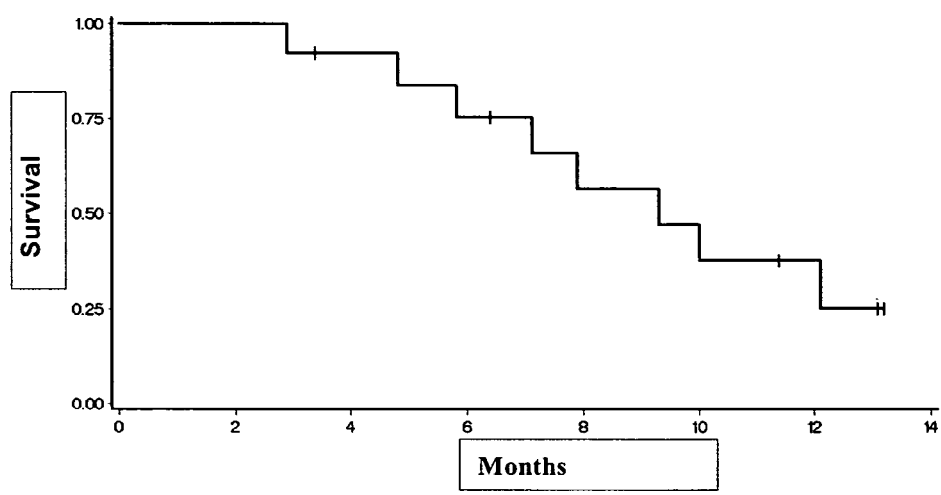
FIGS. 15A-15D show clinical response to vaccination.
Figure 15:
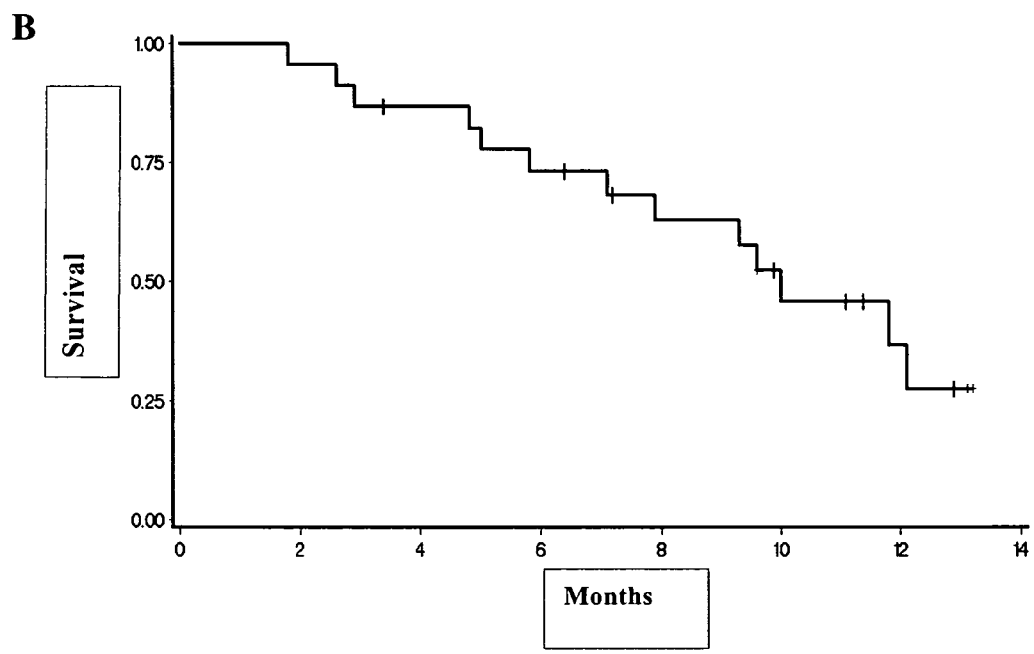
Figure 15:
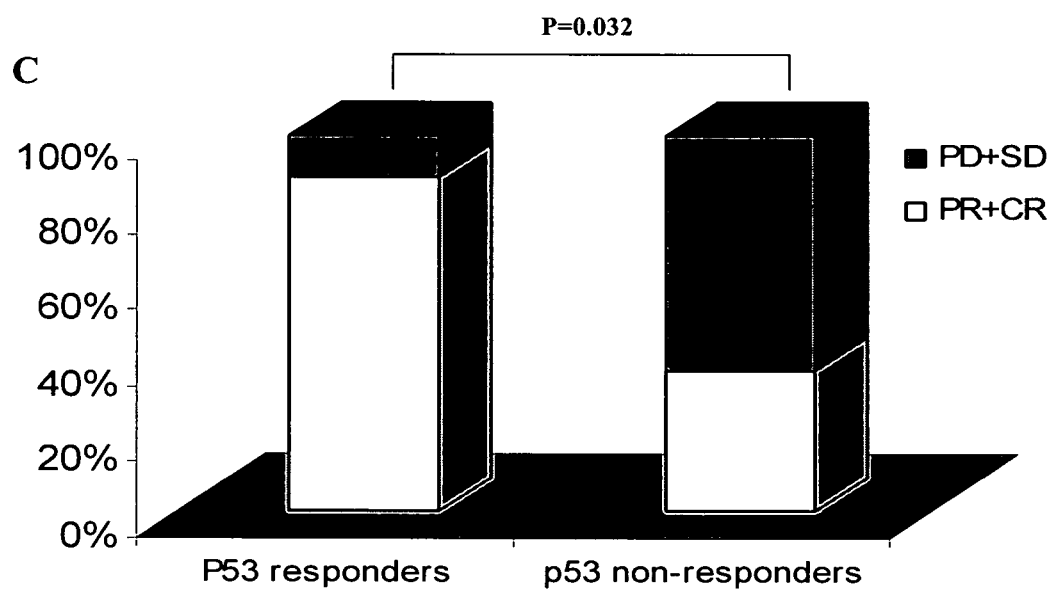
Figure 15:
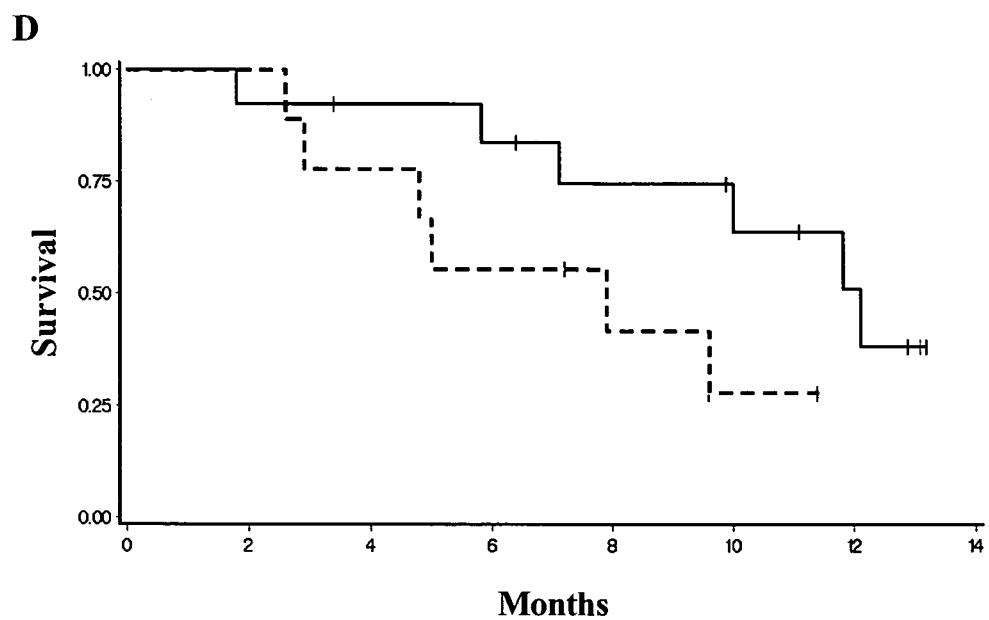

Twenty-three treated patients to date are evaluable for immune and clinical responses. One patient was removed from the immune response analysis due to the loss of a blood specimen. One patient achieved a PR after vaccination but has not been included in the clinical response analysis because she has not yet completed the immune response analysis. None of 23 fully evaluable patients who had measurable lesions had tumor regressions in response to the vaccines, but five had stable disease. All but 2 of the 23 patients eventually developed progressive disease. Eighteen of the 21 patients with progressive disease were treated with additional chemotherapy (3 patients declined). Of these, 13 were platinum resistant (refractory) (progressed within 90 days of receiving a platinum containing regimen). Thirteen patients received Paclitaxel (Taxol), two patients—carboplatin/CPT-11, two patients CDDP/CPT-11, and one patient carboplatin/VP-16. Historic objective response rate to second-line chemotherapy in patients with platinum resistant extensive stage SCLC is 2%-5% and for studies where >50% patients had refractory disease (as in our patient population), 6%-16% (Davies et al., 2004). However, the present inventors found objective clinical response (PR+CR) in 66.7% of all 18 patients treated with second-line chemotherapy (Table 6). Of the 13 platinum resistant patients treated with the vaccine, who received various chemotherapeutic regimens when they progressed after receiving the vaccine, response rate was 61.5% (Table 6). The median survival of these platinum resistant patients (n=13) from the time of the first vaccine administration was 9.3 months with a lower 95% confidence interval of 7.1 months (FIG. 15A). The overall survival of all 23 evaluable patients was 10 months from the time of the first vaccine administration, with a lower 95% confidence interval of 7.1 months (FIG. 15B).

TABLE 6

Response to second-line chemotherapy in vaccinated patients

| All patients who received chemo after vaccine: n = 21 | | | Platinum resistant patients who received chemo after vaccine: n = 13 | | |
|---|---|---|---|---|---|
| Response | # | % | Response | # | % |
| CR | 3 | 14.3% | CR | 1 | 8% |
| PR | 10 | 47.6% | PR | 7 | 54% |
| SD | 4 | 19.05% | SD | 3 | 23% |
| PD | 4 | 19.05% | PD | 2 | 15% |
| CR + PR | 13 | 61.9% | CR + PR | 8 | 61.5% |

The present inventors evaluated the connection between immunological response to immunization and clinical response to second-line chemotherapy. Eight out of 9 patients (88.9%) with positive immunological response to immunization had CR or PR to second-line chemotherapy compared with 3 out of 9 patients (33.3%) with no detectable immunological response (two-tailed p=0.0497 in Fisher's exact test) (FIG. 15C). Patients with positive immunological response to vaccination had improved overall survival (median 12.1 months) than patients who did not respond immunologically to vaccination (median survival, 7.9 months)(FIG. 15D). However, the difference between the two survival curves did not reach statistical significance (p=0.075).

The administration of second line chemotherapy started in most patients 3 to 4 weeks after the end of the vaccination. To follow-up the status of the specific immune response in these patients, we evaluated p53-specific immune response 2 months after the last vaccination. In most patients, there was a significant decrease in the p53-specific immune responses (FIGS. 12A, 17A). This decrease was not associated with significant chemotherapy-induced lymphopenia (FIG. 17B).

Example 8

Clinical Response in One Patient After 3 Vaccines

Figure 16:
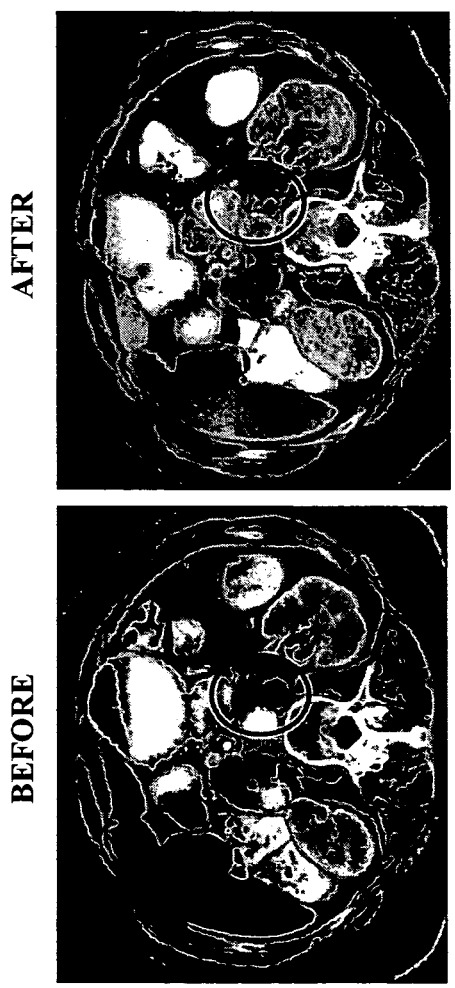
FIG. 16 shows a clinical response to vaccine. A patient with progressive disease in retroperitoneal lymph nodes (new, and positive on PET scan) 2 months after cisplatin/etoposide was treated with 3 vaccines at the time of progression. A PR was observed six weeks after the first vaccine administration. On the left, an abdominal CT scan performed 1 week prior to the first vaccine demonstrates 2 enlarged retroperitoneal lymph nodes (circled, each 2 cm in diameter). Two weeks after the third vaccine, the CT scan on the right was obtained demonstrating a greater than 60% reduction in the size of both lesions.

One patient was not included in the clinical analysis above because she has not yet completed the immune response analysis. This patient achieved a PR after the third vaccine administration. This patient received 4 cycles of cisplatin and etoposide concurrent with thoracic radiation therapy immediately after the initial diagnosis. She subsequently progressed 2 months after her last dose of cisplatin, with the appearance of several PET positive enlarged retroperitoneal lymph nodes. She received 3 vaccines at that time, and was restaged 2 weeks later. Overall RECIST measurements revealed a 60% decrease in the size of all of her measurable lesions (FIG. 16).

Example 9

Significance of the Present Invention

The present invention regards an immune response generated after intradermal administration of the exemplary Ad-p53 treated dendritic cells (DC). Since both Adv associated antigens and p53-derived epitopes are presented on the same DC, evaluation of anti-Adv immunity can serve as a correlate for functional activity of DC, in specific embodiments. However, very high levels of anti-Adv response may be detrimental due to immunologic competition between presenting epitopes. In three patients who failed second line chemotherapy, two did not have detectable increase in anti-Adv antibody response and one had very high (>8-fold) increase, whereas 6 out of 8 patients who responded to chemotherapy had moderately increased level of anti-Adv antibody and 2 did not have that increase. However, the data are consistent with the concept of shared antigen presentation by DC, and thus anti-Adv immunity may serve as a surrogate marker for induction of np53 immunity.

To optimize p53-specific response of immune system, the present inventors used DCs loaded with adenovirus containing wild-type p53 gene. Adenovirus is not only excellent tool for gene delivery into DCs (rev. in Humrich and Jenne, 2003; Gamvrellis et al., 2004) but also induced activation of these cells that manifests in up-regulation of MHC class II and co-stimulating molecules on DC surface, production of IL-12, Th1, and pro-inflammatory cytokines as well as functional potency (Nikitina et al., 2002; Tan et al., 2005; Herrera et al., 2002; Miller et al., 2002; Korst et al., 2002; Miller et al., 2003). Thus, adenovirus provides a unique opportunity to combine Ag delivery and DC activation and may provide additional benefits for DC based cancer immunotherapy.

In specific aspects, Adv provide high-level transduction efficacy for many cell types, regardless of the mitotic status of the cell (Becker et al., 1994). Replication defective Adv with deletions in the E1 region have been directly injected into people in many clinical trials (reviewed in Roth and Cristiano, 1997). Successful transduction of APC, and DC in particular, with model Ags has been reported (Broassart et al., 1997; Dietz and vuk-Pavlovic, 1998). Transduced DCs were able to effectively present the recombinant protein Ags. The results of pre-clinical studies using tumor bearing murine models and initial results evaluating human p53-specific CTL precursors have demonstrated that Ad-p53 transduced DC were able to induce potent antitumor responses (Nikitina et al., 2002). This response recognized epitopes associated with different mutant p53 and led to tumor protection from p53-associated tumors as well as to a significant decrease in the growth of established tumors (Nikitina et al., 2002; Ishida et al., 1999). Thus, p53 has many characteristics of "ideal" TAA and is a very attractive candidate for use in cancer immunotherapy.

DC play a crucial role in an antitumor immune response. Tumor protection as well as limited therapeutic effects were induced when DC were used for induction of immune responses (reviewed in Gabrilovich, 2002). Thus, DC are ideal candidates as vehicles to deliver specific Ags for induction of immunity. A number of clinical trials have utilized DC based vaccines in various types of cancers. These studies show that Ag-loaded DC immunizations are safe and promising in the treatment of cancer. They include trials in Non-Hodgkin's lymphoma, B-cell lymphoma, multiple myeloma, prostate cancer, malignant melanoma, colorectal cancer, etc. Currently it appears that one of the critical factors in DC based immunization is the activation status of DC. Immature DC are not able to stimulate potent immune responses. Moreover, they may induce inhibition of Ag-specific T-cells (Dhodapkar et al., 2001. Adenovirus provides a unique opportunity to combine Ag delivery and DC activation. DC transduced with Adv clearly become more mature using the phenotypic criterion of up-regulation of CD83 and down-regulation of CD14. Transduced DC also decrease production of IL-10, and a subset of transduced DC produce increased levels of IL-12 p70. This level of maturation is superior to that achieved by treatment of these cells with tumor necrosis factor-alpha or interferon-alpha but less pronounced than with CD40L trimer or a combination of CD40L plus interferon-gamma (Schumacher et al., 2004). Maturation by Adv transduction alone leads to efficient stimulation of Ag-specific T cells from both healthy donors and patients with advanced cancer using two defined human tumor-associated Ags, MART-1 and AFP (Schumacher et al., 2004). The ability of Adv to induce DC maturation/activation has been well established (Nikitina et al., 2002; Miller et al., 2003; Miller et al., 2002; Korst et al., 2002). These data indicate that the adenoviral construct can provide additional benefits for DC based cancer immunotherapy.

Selection of patients with ES SCLC allowed the present inventors not only administered vaccine to patients with relatively low tumor volume (after initial chemotherapy) but also provide an opportunity to evaluate clinical response to vaccination. The present invention evaluated the immune response generated after intradermal administration of Ad-p53 treated DC. IFN-γ ELISPOT currently is one of the most sensitive measure of immune response to vaccination. In the invention, the inventors used two different variants of this test: one using ALVAC p53 and the other one using HLA-A2 matched peptide. ALVAC allowed for evaluation of p53 specific response regardless of HLA-type of the patients. However, it did not allow for discrimination between CD4+ and CD8+ T cells response. Peptides allowed for the analysis of the specific CD8+ T cell response but could be used only in HLA-A2 positive patients. In the hands of the inventors, no differences in the frequency of the responses were seen between ALVAC and the peptide approach. Overall, 54.5% of all patients demonstrated a p53-specific response to vaccination. This rate is consistent with a previously reported immunological response rate in patients treated with other DC-based vaccines. The present inventors characterized the factors limiting p53-specific response to vaccination. Using samples of blood collected prior to vaccination, there was comparison of pre-vaccination level of T cell and DC function with antigen-specific response to vaccine. Although presence of DCs in peripheral blood was decreased only in a fraction of patients, many patients had decreased T-cell and DC function. These data are consistent with previously reported observations (reviewed in Gabrilovich, 2004; Gabrilovich and Pisarev, 2003). However, no association between these parameters and p53-specific response to vaccination have been found. $CD4^+$ $CD25^+$ $T_{reg}$ have been implicated in cancer association immune defects (Zou et al., 2005). Increase in the population of these cells is not always indicative of up-regulation of $T_{reg}$, since a substantial proportion of $CD4^+CD25^+$ T cells are represented by activated T cells. Currently, several markers could be used for more precise identification of $T_{reg}$ population; however, functional tests remains the only reliable method to determine the nature of these cells (Chattopadhyay et al., 2005; Zou et al., 2005). The present inventors could not detect a substantial increase in the presence of a $CD4^+$ $CD25^{high}$ population of T cells, which made further analysis unnecessary. The data does not necessarily indicate lack of involvement of $T_{reg}$ in SCLC. Patients were treated with platinum-based chemotherapy just six weeks before the analysis. In specific embodiments, chemotherapy could eliminate some of these cells, as it was previously reported for cyclophosphamide (Ghiringhelli et al., 2004). Patients with ES SCLC had increased level of ImC, the cells implicated in tumor-associated immune suppression (Kusmartsev and Gabrilovich, 2002; Gabrilovich, 2004; Bronte et al., 2001). Importantly, 80% of patients with normal pre-vaccine level of ImC had a p53-specific response to vaccination, compared with only 28.6% of patients with elevated pre-vaccine level of ImC. Although those differences did not reach statistical significance (p=0.07), they demonstrate a strong trend and suggest that an increase in ImC may negatively affect an antigen-specific response to vaccine. After vaccination the presence of ImC increased even further, with only two patients having normal level of these cells (both had positive response to vaccination). An increase in ImC may be caused by the fact that most of the patients had progressive disease by the time of evaluation. In specific embodiments, removal of ImC is beneficial in enhancing the effect of cancer vaccines.

Induction of anti-adenovirus antibody response is considered as one of the major limiting factor for use of this vector in gene therapy. In these studies, 12 out of 23 patients showed increased titer of anti-adenovirus antibody. Interestingly, a p53-specific response to vaccination was found primarily in patients with moderate increase in the titer (90%). Only ⅓ of patients without increase in the titer had developed a positive p53-specific response to vaccination (p=0.011). Since both adenovirus and p53-derived antigens are presented on the same DC, evaluation of anti-Adv immunity may serve as a correlate for functional activity of DC. However, very high levels of anti-Adv response may be detrimental due to immunologic competition between presenting epitopes. Patients who developed very strong anti-adenovirus response failed to generate p53-specific response to vaccination. These data are consistent with the results obtained in animal models that demonstrated that limited anti-adenovirus response generated after immunization of mice with DCs transduced with different adenoviral constructs did not affect antigen-specific CTL activity (Nikitina et al., 2002; Brossart et al., 1997).

Despite induction of an antigen-specific immune response in more than half of the patients, objective clinical response was observed in only one patient (4.2%). Importantly, it was similar to that described in previous clinical trials (Rosenberg et al., 2004). However, after treatment of patients with second-line chemotherapy, most of the vaccinated patient had objective clinical response (CR or PR) to the treatment. Importantly, clinical response to vaccination correlated with immunological response. Less than 40% of patients who did not have a p53-specific response to vaccination responded clinically to second-line chemotherapy, whereas almost 90% of p53 responders had objective clinical response to vaccination. Induction of p53 cellular immunity correlated with improved survival in this group of incurable patients. These data indicate that vaccination synergizes with chemotherapy in patients with SCLC. Chemotherapy eventually blunted antigen-specific T-cell response, since it was practically undetectable 6-8 weeks after start of the chemotherapy. In particular aspects, a synergistic effect of immunotherapy and chemotherapy is taking place during the first couple of weeks after start of the treatment. In specific embodiments, one or more of the following mechanisms of the observed effect may be employed: chemotherapy may down-regulate the effect of tumor-produced immunosuppressive factors that prevent CTLs to kill tumor cells; chemotherapy can up-regulate p53 in tumor cells, making them more susceptible to recognition by CTLs; chemotherapy may activate CTLs by up-regulating the level of expression of perforin or granzymes; and a pro-apoptotic effect of granzymes and chemotherapy may be synergized on molecular level.

It has been recently suggested that combination of cancer immunotherapy and immunotherapy may provide potential significant benefit (Lake and Robinson, 2005). The present invention provides the first direct clinical demonstration in support of this new emerging paradigm in the practical application of cancer immunotherapy. A cancer vaccine is enhanced in combination with other methods of treatment, specifically chemotherapy.

In summary, the data presented herein indicate that active immunization with the exemplary Ad-p53 treated DC in patients with ES or relapsed SCLC is safe and results in induction of p53-specific immune activation in >50% of patients. The present inventors provide a comprehensive analysis of p53 and Adv immune induction at both the humoral and cellular level. Induction of p53 cellular immunity correlated with improved survival in this group of incurable patients.

Example 10

Exemplary Materials and Methods

Exemplary materials and methods suitable in the invention are described herein, although one of skill in the art would recognizes that these are non-limiting in nature.

Immune Activation Assays.

Briefly, mononuclear cells were infected with ALVAC-p53 or ALVAC-control and the number of IFN-γ producing cells was evaluated using automatic ELISPOT reader (CTL) as described previously (Pisarev et al., 2003). as described earlier (Nikitina et al., 2001). All ELISPOT experiments were performed in quadruplicates. The levels of anti-p53 and anti-Adv antibodies were evaluated in ELISA using at least 4 serial dilutions. Internal controls provided by manufacturers were used to establish a "cut-off" level.

Patient Eligibility.

Before enrolling patients, the protocol was reviewed and approved by the FDA (BB-IND 9792), the NIH Office of Biotechnology Activities' Recombinant DNA Advisory Committee (OBA#0205-538), the University of South Florida Institutional Review Board, and the USF Institutional Biosafety Committee. Patients aged 18 or older with a histologic diagnosis of extensive stage SCLC were eligible to participate. ECOG performance status of 0-2, and adequate organ function (WBC>3,000/mm$^3$ and ANC>1500/mm$^3$, platelets>100,000/mm$^3$, hematocrit>25%, bilirubin<2.0 mg/dl, and creatinine<2.0 mg/dl) were required. Patients with a pre-existing autoimmune disorder, an immunodeficiency condition, a serious ongoing infection, or uncontrolled brain metastases were not eligible.

Treatment Plan.

All patients were treated with conventional cytotoxic chemotherapy prior to receiving the investigational vaccine. Patients who had progressive disease after chemotherapy were eligible if they otherwise met all other inclusion criteria. At least 6 weeks after the last dose of chemotherapy, the patients underwent leukapheresis. Vaccines were produced and administered by intra-dermal injection at 4 separate sites that drain to bilateral axillary and inguinal lymph node basins. This was repeated on 3 separate occasions, every 2 weeks. Two weeks after the third set of vaccines, the patients were re-staged. Those patients who did not exhibit progressive disease at this point underwent a second leukapheresis procedure, and received 3 additional sets of vaccines, this time every 4 weeks. Patients who developed progressive disease after the third or sixth vaccine were offered additional cytotoxic chemotherapy.

Vaccine Production.

Mononuclear cells for DC production were obtained after leukapheresis and kept stored in liquid nitrogen. After thawing cells were placed in X-VIVO-15 medium (Biowhittaker, Walkersville, Md.) in tissue culture flasks at a concentration of 1.3-1.7×10$^6$ cells per cm$^2$ of available culturing surface. After 2-hr culture non-adherent cells were removed and the flasks were recharged with X-VIVO-15 medium supplemented with 5 ng/ml GM-CSF (Immunex), 5 ng/ml IL-4 (R&D Systems, Minneapolis, Minn.), and 2% human serum albumin. The flasks were incubated for 48 hours, at which time additional cytokine supplemented medium were added to the flasks. The flasks were then incubated for additional 72 hours. At the conclusion of incubation, the non-adherent and loosely adherent cells will be collected and used for 2-hr infection with Ad-p53 at a viral particle to cell ratio of 15,000:1. The optimal dose of adenovirus that would produce the highest level of human p53 expression with the least amount of toxicity to the dendritic cells was determined. At the conclusion of the two-hour incubation, X-VIVO medium was added to a final cell concentration of 10$^6$ cells/mL, and cells were incubated in flasks for an additional 46 hours, at which time the cells were harvested and analyzed. Vaccine release criteria include: (a) negative Gram's staining; (b) negative mycoplasma test by PCR analysis; (c) maximum endotoxin concentration of 5 EU/mL; and (d) a mature DC phenotype with evidence of intracellular p53 expression by flow cytometry analysis. To determine the latter, cells were treated with "fix and perm" reagent (Caltag). Staining with p53 specific antibody followed by a PE labeled anti-murine antibody. After washing of excess antibody, surface staining for linage markers (CD3, CD14, CD19, CD20, CD56) with FITC tagged monoclonal antibodies, and for HLA-DR with PE tagged monoclonal antibodies was performed. The final product was analyzed on flow cytometry.

Vaccine Administration.

On the scheduled days for vaccine administration, the appropriately tested DCs were suspended in 1 ml of sterile PlasmaLyteA medium. One quarter mL of the cell suspension was injected intradermally into four separate sites to include proximal upper and lower extremities. The patients were monitored for acute toxicity for at least 1 hour after the injections.

Briefly, mononuclear cells were infected with ALVAC-p53 or ALVAC-control and the number of IFN-γ producing cells was evaluated using automatic ELISPOT reader (CTL) as described previously (Pisarev et al., 2003) as described earlier (Nikitina et al., 2001). All ELISPOT experiments were performed in quadruplicates.

The levels of anti-p53 and anti-Adv antibodies were evaluated in ELISA using at least 4 serial dilutions. Internal controls provided by manufacturers were used to establish a "cut-off" level.

Patient Assessment.

Patients were monitored for toxicity, particularly for evidence of autoimmunity. CBC's to monitor for hematologic toxicity, serum creatinine to monitor for renal toxicity, LFT's to monitor for hepatic toxicity, an d a standard clinical toxicity assessment will be performed every other week throughout the period of immunization. In addition, a medical history and physical examination will be performed on a monthly basis.

Immune Response Evaluation.

Analysis of IFN-γ producing cells in ELISPOT assay. Peripheral blood mononuclear cells were collected from patients prior vaccination, 2-3 weeks after completion of 3 vaccination and 2 months later. Samples were kept in aliquots in liquid nitrogen. Samples from one patients were thawed and analyzed simultaneously. ALVAC-p53 a recombinant canarypoxvirus containing full-length wild-type p53 was obtained from Aventis Pasteur (Toronto, Canada). ALVAC-control contains empty vector. Mononuclear cells were infected with ALVAC-p53 or ALVAC-control for 2 hr in serum free medium at multiplicity of infection (MOI) 4 plaque forming units (PFU) per cell. After infection cells were seeded in quadruplicates in complete culture medium supplemented with IL-2 (2×10$^5$ cells pre well) in 96-well plates pre-coated with anti-IFN-γ antibody and incubated for 36 hr. The number of IFN-γ producing cells was evaluated using automatic ELISPOT reader (CTL) as described previously (Nikitina et al., 2001; Pisarev et al., 2003).

In HLA-A2 positive patients MNC in parallel were incubated for 36 hr with 10 µg/ml of either p53-derived HLA-A2 binding peptide LLGRNSFEV or control PSA-derived peptide—FLTPKKLQCV. The number of IFN-γ producing cells was evaluated in ELISPOT assay as described previously (Pisarev et al., 2003).

Tetramer Staining.

Tetramer HLA-A-0201/LLGRNSFEV was made in NIAID MHC tetramer core facility at Yerkes Regional Primate Research Center. MNC cells were stained for 60 min at 4° C. with APC-conjugated anti-CD8 antibody and PE-conjugated tetramer (1:100 dilution). The proportion of tetramer positive cells within the population CD8+ T cells was calculated.

Evaluation of Humoral Immune Response.

The levels of anti-p53 and anti-Adv antibodies (IgG and IgM) were evaluated in ELISA using at least 4 serial dilutions. Internal controls provided by manufacturers were used to establish a "cut-off" level. Samples were always assayed in duplicate. The absorbance was read on a spectrophotometer at a wavelength of 450 nm against a reference filter of 620 nm in order to compensate for differences in the material of the microtitre plate. The p53-Autoantibody Elisa PLUS kit (Oncogene Research) was used to measure circulating antibodies to p53 in human serum samples. Adenovirus IgG/IgM ELISA kits were purchased from IBL Immuno-Biological Laboratories (Hamburg, Germany).

Statistical Analysis.

All patients who received at least one vaccine were evaluable for toxicity from the time of their first treatment with the Ad-p53 DC vaccine. Three patients who received at least one vaccine had early progression and were removed from the study prior to receiving the minimum treatment with 3 vaccines, and were considered in the final analysis. Survival estimates were determined using the method of Kaplan and Meier with variances calculated using Greenwood's formula. The log rank test was used to determine the significance of a difference between two survival curves.

REFERENCES

The following references, to the extent that they provide exemplary procedural or other details supplementary to those set forth herein, are specifically incorporated herein by reference.

PATENTS AND PATENT APPLICATIONS

U.S. Pat. No. 4,430,434, issued Feb. 7, 1984
U.S. Pat. No. 4,452,901, issued Jun. 5, 1984.
U.S. Pat. No. 4,727,028, issued Feb. 23, 1988
U.S. Pat. No. 4,960,704, issued Oct. 2, 1990.
U.S. Pat. No. 5,399,363, issued Mar. 21, 1995.
U.S. Pat. No. 5,466,468, issued Nov. 14, 1995.
U.S. Pat. No. 5,543,158, issued Aug. 6, 1996.
U.S. Pat. No. 5,580,579, issued Dec. 3, 1996.
U.S. Pat. No. 5,602,306, issued Feb. 11, 1997
U.S. Pat. No. 5,633,016, issued May 27, 1997.
U.S. Pat. No. 5,639,940, issued Jun. 17, 1997.
U.S. Pat. No. 5,641,515, issued Jun. 24, 1997.
U.S. Pat. No. 5,643,786, issued Jul. 1, 1997.
U.S. Pat. No. 5,648,219, issued Jul. 15, 1997.
U.S. Pat. No. 5,656,016, issued Aug. 12, 1997.
U.S. Pat. No. 5,658,583, issued Aug. 19, 1997.
U.S. Pat. No. 5,697,899, issued Dec. 16, 1997.
U.S. Pat. No. 5,707,644, issued Jan. 13, 1998.
U.S. Pat. No. 5,718,914, issued Feb. 17, 1998.
U.S. Pat. No. 5,720,936, issued Feb. 24, 1998.
U.S. Pat. No. 5,725,871, issued Mar. 10, 1998.
U.S. Pat. No. 5,739,169, issued Apr. 14, 1998.
U.S. Pat. No. 5,747,469, issued May 5, 1998.
U.S. Pat. No. 5,756,353, issued May 26, 1998.
U.S. Pat. No. 5,770,219, issued Jun. 23, 1998.
U.S. Pat. No. 5,780,045, issued Jul. 14, 1998.
U.S. Pat. No. 5,783,208, issued Jul. 21, 1998.
U.S. Pat. No. 5,788,963, issued Aug. 4, 1998.
U.S. Pat. No. 5,789,655, issued Aug. 4, 1998.
U.S. Pat. No. 5,792,451, issued Aug. 11, 1998.
U.S. Pat. No. 5,797,898, issued Aug. 25, 1998.
U.S. Pat. No. 5,798,339, issued Aug. 25, 1998.
U.S. Pat. No. 5,801,005, issued Sep. 1, 1998.
U.S. Pat. No. 5,804,212, issued Sep. 8, 1998.
U.S. Pat. No. 5,811,128, issued Sep. 22, 1998.
U.S. Pat. No. 5,811,297, issued Sep. 22, 1998.
U.S. Pat. No. 5,814,599, issued Sep. 29, 1998.
U.S. Pat. No. 5,824,311, issued Oct. 20, 1998.
U.S. Pat. No. 5,824,346, issued Oct. 20, 1998.
U.S. Pat. No. 5,827,530, issued Oct. 27, 1998.
U.S. Pat. No. 5,830,682, issued Nov. 3, 1998.
U.S. Pat. No. 5,830,880, issued Nov. 3, 1998.
U.S. Pat. No. 5,836,935, issued Nov. 17, 1998.
U.S. Pat. No. 5,843,689, issued Dec. 1, 1998.
U.S. Pat. No. 5,846,225, issued Dec. 8, 1998.
U.S. Pat. No. 5,846,233, issued Dec. 8, 1998.
U.S. Pat. No. 5,846,928, issued Dec. 8, 1998.
U.S. Pat. No. 5,849,589, issued Dec. 15, 1998.
EPO 0273085
WPO 94/11514

PUBLICATIONS

Allen et al., "A Mutation Hot Spot in the Bcrp1 (Abcg2) Multidrug Transporter in Mouse Cell Lines Selected for Doxorubicin Resistance1," Cancer Research 62, 2294-2299, Apr. 15, 2002.

Allison, "Immunological adjuvants and their modes of action," Arch. Immunol. Ther. Exp. (Warsz), 45(203):141-147, 1997.

Allison, "The mode of action of immunological adjuvants," Dev. Biol. Stand., 92:3-11, 1998.

Alt, Kellems, Bertino and Schimke, J. Biol. Chem., 253:1357, 1978.

Ardizzoni, A. et al. Topotecan, a new active drug in the second-line treatment of small-cell lung cancer: a phase II study in patients with refractory and sensitive disease. The European Organization for Research and Treatment of Cancer Early Clinical Studies Group and New Drug Development Office, and the Lung Cancer Cooperative Group. J Clin Oncol. 15, 2090-6 (1997).

Arthur et al., "A comparison of gene transfer methods in human dendritic cells," Cancer Gene Ther., 4(1):17-25, 1997.

Austin-Ward, Villaseca, "Gene therapy and its applications," Rev. Med. Chil., 126(7):838-45, 1998.

Baichwal et al., "Vectors for gene transfer derived from animal DNA viruses: Transient and stable expression of transferred genes," In: Gene transfer, Kucherlapati R, ed., New York: Plenum Press, pp. 117-148, 1986.

Becker, T. C. et al. Use of Recombinant Adenovirus for Metabolic Engineering of Mammalian Cells. Meth. Cell Biol. 43, 161-176. (1994).

Bernard et al., "HIV-specific cytotoxic T-lymphyocyte activity in immunologically normal HIV-infected persons," AIDS, 12(16):2125-2139, 1998.

Bertholet et al., "Cytotoxic T lymphocyte responses to wild-type and mutant mouse p53 peptides," Eur. J. Immunol., 27(3):798-801, 1997.

Blaszczyk-Thurin, M., Ertl, I. O. & Ertl, H. C. An experimental vaccine expressing wild-type p53 induces protective immunity against glioblastoma cells with high levels of endogenous p53. Scand J Immunol. 56, 361-75 (2002).

Bodner, S. M. et al. Expression of mutant p53 proteins in lung cancer correlates with the class of p53 gene mutation. Oncogene. 7, 743-9. (1992).

Bourlais et al., "Opthalmic drug delivery systems-recent advances." Prog. Retin. Eye Res., 17:33-58, 1998.

Brizel, "Future directions in toxicity prevention," Semin. Radiat. Oncol., 8(4 Suppl. 1):17-20, 1998.

Brossart, P., Goldrath, A. W., Butz, E. A., Martin, S. & Bevan, M. J. Virus-mediated delivery of antigenic epitopes into dendritic cells as a means to induce CTL. J. Immunol. 158, 3270-3276 (1997).

Bukowski, Rayman, Uzzo, Bloom, Sandstrom, Peereboom, Olencki, Budd, McLain, Elson, Novick, Finke, "Signal transduiction abnormalities in T lymphocytes from patients with advanced renal carcinoma: clinical relevance and effects of cytokine therapy," Clin. Cancer Res., 4(10): 2337-47, 1998.

Caldovic and Hackett Jr., "Development of position-independent expression vectors and their transfer into transgenic fish," Mol. Mar. Biol. Biotechnol., 4(1):51-61, 1995.

Caley, Betts, Davis, Swanstrom, Frelinger, Johnston, "Venezuelan equine encephalitis virus vectors expressing HIV-1 proteins: vector design strategies for improved vaccine efficacy," Vaccine 17(23-24):3124-35, 1999.

Carver, Dalrymple, Wright, Cottom, Reeves, Gibson, Keenan, Barrass, Scott, Colman, et al., "Transgenic livestock as bioreactors: stable expression of human alpha-1-antitrypsinby a flock of sheep," Biotechnology N.Y., 1 (11): 1263-1270, 1993.

Celluzzi and Falo, "Epidermal dendritic cells induce potent antigen-specific CTL-mediated immunity," J. Invest. Dermatol., 108(5):716-720, 1997.

Chalfie et al., Science, 263:802-805, 1994.

Chang et al., "Foreign gene delivery and expression in hepatocytes using a hepatitis B virus vector," Hepatology, 14:134A, 1991.

Chattopadhyay, et al., "Regulatory T cells and tumor immunity," Cancer Immunol Immunother, 54:1153-61, 2005.

Chen and Okayama, "High-efficiency transfection of mammalian cells by plasmid DNA," Mol. Cell Biol., 7:2745-2752, 1987.

Chikamatsu, K. et al. Generation of anti-p53 cytotoxic T lymphocytes from human peripheral blood using auologous dendritic cells. Clin. Cancer Res. 5, 1281-1288 (1999).

Christodoulides, Brooks, Rattue, Heckels, "Immunization with recombinant class 1 outer-membrance protein from *Neisseria meningitidis*: influence of liposomes and adjuvants on antibody avidity, recognition of native protein and the induction of a bactericidal immune response against meningococci," Microbiology, 144(Pt 11):3027-37, 1998.

Cicinnati, V. R. et al. Impact of p53-based immunization on primary chemically-induced tumors. Int J Cancer. 113, 961-70 (2005).

Ciernik, Berzofsky, Carbone, "Induction of cytotoxic T lymphocytes and antitumor immunity with DNA vaccines expressing single T cell epitopes," J. Immunol., 156(7): 2369-75, 1996.

Clark, Voulgaropoulou, Fraley, Johnson, "Cell lines for the production of recombinant adeno-associated virus," Human Gene Therapy, 6:1329-1341, 1995.

Clarke R, Leonessa F, Trock B. Multidrug resistance/P-glycoprotein and breast cancer: review and meta-analysis. Semin Oncol. December; 32(6 Suppl 7):S9-15, 2005.

Coffin, "Retroviridae and their replication," In: Virology, Fields et al. (eds.), New York: Raven Press, pp. 1437-1500, 1990.

Colberre-Garapin et al., J. Mol. Biol., 150:1, 1981.

Cotten, Wagner, Zatloukal, Phillips, Curiel, "High efficiency receptor-mediated delivery of small and large (48 kilobase) gene constructs using the endosome disruption activity of defective or inactivated adenovirus particles," Proc. Natl. Acad. Sci. USA, 89:6094-6098, 1992.

Couch et al., "Immunization with types 4 and 7 adenovirus by selective infection of the intestinal tract," Am. Rev. Resp. Dis., 88:394-403, 1963.

Coupar et al., "A general method for the construction of recombinant vaccinia virus expressing multiple foreign genes," Gene, 68:1-10, 1988.

Cozzi, Tucker, Langford, Pino-Chavez, Wright, O'Connell, Young, Lancaster, McLanghlin, Hunt, Bordin, White, "Characterization of pigs transgenic for human decay-accelerating factor," Transplantation, 64(10):1383-1392, 1997.

Curiel, "Gene transfer mediated by adenovirus-polylysine DNA complexes," In: Viruses in Human Gene Therapy, J.-M. H. Vos (Ed.), Carolina Academic Press, Durham, N.C., pp. 179-212, 1994.

Curran, "Radiation-induced toxicities: the role of radioprotectants," Semin. Radial. Oncol., 8(4 Suppl. 1):2-4, 1998.

D'Amico, D. et al. High frequency of somatically acquired p53 mutations in small-cell lung cancer cell lines and tumors. Oncogene. 7, 339-46. (1992).

Davidson, Musk, Wood, Morey, Ilton, Yu, Drury, Shilkin, Robinson, "Intralesional cytokine therapy in cancer: a pilot study of GM-CSF infusion in mesothelioma," J. Immunother., 21(5):389-98, 1998.

Davies, A. M., Evans, W. K., Mackay, J. A. & Shepherd, F. A. Treatment of recurrent small cell lung cancer. Hematol Oncol Clin North Am. 18, 387-416 (2004).

Davies, A. M., Evans, W. K., Mackay, J. A. & Shepherd, F. A. Treatment of recurrent small cell lung cancer. Hematol Oncol Clin North Am. 18, 387-416 (2004).

De Leo, A. B. p53-based immunotherapy of cancer. Approaches ro reversing unresponsiveness to T lymphocytes and preventing tumor escape. Adv Otorhinolaryngol. 62, 134-50 (2005).

DeLeo, "p53-based immunotherapy of cancer," Crit. Rev. Immunol., 18(1-2):29-35, 1998.

Dhodapkar, M. V., Steinman, R. M., Krasovsky, J., Munz, C. & Bhardwaj, N. Antigen-specific Inhibition of Effector T Cell Function in Humans after Injection of Immature Dendritic Cells. J. Exp. Med. 193, 233-238 (2001).

Dietz, A., B., & Vuk-Pavlovic, S. High efficiency adenovirus-mediated gene transfer to human dendritic cells. Blood. 91, 392-398 (1998).

Dupuis et al., "Dendritic cells internalize vaccine adjuvant after intramuscular injection," Cell Immunol., 186(1):18-27, 1998.

Ebert, Selgrath, DiTulio, Denman, Smith, Memon, Schindler, Monastersky, Vitale, Gordon, "Transgenic production of a variant of human tissue-type plasminogen activator in goat milk: generation of transgenic goats and analysis of expression," Biotechnology N.Y., 9(9):835-838, 1991.

el-Kareh, Secomb, "Theoretical models for drug delivery in solid tumors," Crit. Rev. Biomed. Eng., 25(6):503-71, 1997.

Erlandsson, "Molecular genetics of renal cell carcinoma," Cancer Genet. Cytogenet, 104(1):1-18, 1998.

Erlandsson, "Molecular genetics of renal cell carcinoma," Cancer Genet. Cytogenet., 104(1):1-18, 1998.

Espenschied, J. et al. CTLA-4 blockade enhances the therapeutic effect of an attenuated poxvirus vaccine targeting p53 in an established murine tumor model. J Immunol. 170, 3401-7 (2003).

Eura, M. et al. A wild-type sequence p53 peptide presented by HLA-A24 induces cytotoxic T lymphocytes that recognize squamous cell carcinomas of the head and neck. Clin. Cancer Res. 6, 979-986 (2000).

Ferkol et al., FASEB J., 7:1081-1091, 1993.

Finlay et al., "Activating mutations for transformation by p53 produce a gene product that forms an hsc70-p53 complex with an altered half-life," Mol. Cell. Biol., 8:531-539, 1988.

Flotte, Afione, Conrad, McGrath, Solow, Oka, Zeitlin, Guggino, and Carter, "Stable in vivo expression of the cystic fibrosis transmembrane conductance regulator with an adeno-associated virus vector," Proc. Natl. Acad. Sci. USA, 90:10613-10617, 1993.

Flotte, Barraza-Ortiz, Solow, Afione, Carter, and Guggino, "An improved system for packaging recombinant adeno-associated virus vectors capable of in vivo transduction," Gene Therapy, 2:29-37, 1995.

Flotte, Solow, Owens, Afione, Zeitlin, and Carter, "Gene expression from adeno associated virus vector in airway epithelial cells," Am. J. Respir. Cell Mol. Biol., 7:349-356, 1992.

Fraley et al., "Entrapment of a bacterial plasmid in phospholipid vesicles: Potential for gene transfer," Proc. Natl. Acad. Sci. USA, 76:3348-3352, 1979.

Franz, Mueller, Haartong, Frey, Katus, "Transgenic animal models: new avenues in cardiovascular physiology," J. Mol. Med., 75(2):115-119, 1997.

Friedmann, "Progress toward human gene therapy," Science, 244:1275-1281, 1989.

Fulci, Ishii, Van Meir, "p53 and brain tumors: from gene mutations to gene therapy," Brain Pathol., 8(4):599-613, 1998.

Gabrilovich et al., "Decreased antigen presentation by dendritic cells in patients with breast cancer," Clin. Cancer Res., 3(3):483-490, 1997.

Gabrilovich et al., "Dendritic cells in antitumor immune responses. II. Dendritic cells grown from bone marrow precursors, but not mature DC from tumor-bearing mice, are effective antigen carriers in the therapy of established tumors," Cell Immunol, 170(1):111-119, 1996.

Gabrilovich et al., "IL-12 and mutant P53 peptide-pulsed dendritic cells for the specific immunotherapy of cancer," J. Immunother. Emphasis Tumor Immunol., 19(6):414-418, 1996.

Gabrilovich, et al., "Dendritic cells in antitumor immune responses. I. Defective antigen presentation in tumor-bearing hosts," Cell Immunol., 170(1):101-10, 1996.

Gabrilovich, D. I. Dendritic cell vaccines for cancer treatment. Curr Opin Mol Ther. 4, 452-458 (2002).

Garroway et al., "Integrative genomic analyses identify MITF as a lineage survival oncogene amplified in malignant melanoma," Nature 436(7047): 117-22, 2005.

Gertig and Hunter, "Genes and environment in the etiology of colorectal cancer," Semin. Cancer Biol., 8(4):285-298, 1997.

Ghosh and Bachhawat, "Targeting of liposomes to hepatocytes," In: Liver Diseases, Targeted Diagnosis and Therapy Using Specific Receptors and Ligands," Wu G. and C. Wu ed. New York: Marcel Dekker, pp. 87-104, 1991.

Ghosh-Choudhury et al., "Protein IX, a minor component of the human adenovirus capsid, is essential for the packaging of full-length genomes," EMBO J, 6:1733-1739, 1987.

Gomez-Foix et al., "Adenovirus-mediated transfer of the muscle glycogen phosphorylase gene into hepatocytes confers altered regulation of glycogen," J. Biol. Chem., 267:25129-25134, 1992.

Gopal., "Gene transfer method for transient gene expression, stable transfection, and cotransfection of suspension cell cultures," Mol. Cell Biol., 5:1188-1190, 1985.

Graham and Prevec, "Adenovirus-based expression vectors and recombinant vaccines," Biotechnology, 20:363-390, 1992.

Graham and Prevec, "Manipulation of adenovirus vector," In: Methods in Molecular Biology: Gene Transfer and Expression Protocol, E. J. Murray (ed.), Clifton, N.J.: Humana Press, 7:109-128, 1991.

Graham and van der Eb, "A new technique for the assay of infectivity of human adenovirus 5 DNA", Virology, 52:456-467, 1973.

Graham et al., "Characteristics of a human cell line transformed by DNA from human adenovirus type 5", J. Gen. Virol., 36:59-72, 1977.

Graham et al., "Characteristics of a human cell line transformed by DNA from human adenovirus type 5", J. Gen. Virol., 36:59-72, 1977.

Grunhaus and Horwitz, "Adenovirus as cloning vector," Seminar in Virology, 3:237-252, 1992.

Hanibuchi, Yano, Nishioka, Yanagawa, Kawano, Sone, "Therapeutic efficacy of mouse-human chimeric antiganglioside GM2 monoclonal antibody against multiple organ micrometastases of human lung cancer in NK cell-depleted SCID mice," Int. J. Cancer, 78(4):480-5, 1998.

Harland and Weintraub, "Translation of mammalian mRNA injected into *Xenopus* oocytes is specifically inhibited by antisense RNA," J. Cell Biol., 101:1094-1099, 1985.

Hartmann et al., "High frequency of p53 gene mutations in primary breast cancers in Japanese women, a low-incidence population," Br. J. Cancer, 73(8):896-901, 1996.

Hartmann et al., "Overexpression and mutations of p53 in metastatic malignant melanomas," Int. J. Cancer, 67(3): 313-317, 1996.

Haskell and Bowen, "Efficient production of transgenic cattle by retroviral infection of early embryos," Mol. Reprod. Dev., 40(3):386-390, 1995.

Hellstrand, Hermodsson, Naredi, Mellqvist, Brune, "Histamine and cytokine therapy," Acta. Oncol., 37(4):347-53, 1998.

Hermonat and Muzyczka, "Use of adeno-associated virus as a mammalian DNA cloning vector; transduction of neomycin resistance into mammalian tissue culture cells," Proc. Natl. Acad. Sci. USA, 81:6466-6470, 1984.

Hersdorffer et al., "Efficient gene transfer in live mice using a unique retroviral packaging line," DNA Cell Biol., 9:713-723, 1990.

Herz and Gerard, "Adenovirus-mediated transfer of low density lipoprotein receptor gene acutely accelerates cholesterol clearance in normal mice," Proc. Natl. Acad. Sci. USA 90:2812-2816, 1993.

Ho, Lau, Leung, Johnson, "Internal radiation therapy for patients with primary or metastatic hepatic cancer: a review," Cancer, 83(9):1894-907, 1998.

Hoffmann, T. K., Bier, H., Donnenberg, A. D., Whiteside, T. L. & De Leo, A. B. p53 as an immunotherapeutic target in head and neck cancer. Adv Otorhinolaryngol. 62, 151-60 (2005).

Horwich et al. "Synthesis of hepadenovirus particles that contain replication-defective duck hepatitis B virus genomes in cultured HuH7 cells," J. Virol., 64:642-650, 1990.

Houbiers et al., "In vitro induction of human cytotoxic T lymphocyte responses against peptides of mutant and wild-type p53," Eur. J. Immunol., 23(9):2072-2077, 1993.

Hui, Hashimoto, "Pathways for potentiation of immunogenicity during adjuvant-assisted immunizations with *Plasmodium falciparum* major merozoite surface protein 1," Infect. Immun., 66(11):5329-36, 1998.

Hurpin et al., "The mode of presentation and route of administration are critical for the induction of immune responses to p53 and antitumor immunity," Vaccine, 16(2-3):208-215, 1998.

Ishida, T. et al. Dendritic cells transduced with wild type p53 gene elicit potent antitumor immune responses. Clinic. Exper. Immunol. 117, 244-251 (1999).

Ishida, T. et al. Dendritic cells transduced with wild-type p53 gene elicit potent anti-tumour immune responses. Clin Exp Immunol. 117, 244-51. (1999).

Johnson and Hamdy, "Apoptosis regulating genes in prostate cancer (review)," Oncol. Rep., 5(3):553-557, 1998.

Johnson, Hamdy, "Apoptosis regulating genes in prostate cancer (review)," Oncol. Rep., 5(3):553-7, 1998.

Jones and Shenk, "Isolation of deletion and substitution mutants of adenovirus type 5," Cell, 13:181-188, 1978.

Kaneda et al., "Increased expression of DNA cointroduced with nuclear protein in adult rat liver," Science, 243:375-378, 1989.

Kang, Cho, Kole, "Up-regulation of luciferase gene expression with antisense oligonucleotides: implications and applications in functional assay development," Biochemistry, 37(18):6235-6239, 1998.

Kaptitt, Leone, Samulski, Siao, Pfaff, O'Malley, During, "Long-term gene expression and phenotypic correction suing adeno-associated virus vectors in the mammalian brain," Nature Genetics, 8:148-154, 1994.

Karlsson et al., EMBO J., 5:2377-2385, 1986.

Karnik, et al. Estrogen receptor mutations in tamoxifen-resistant breast cancer, Cancer Research, Vol 54, Issue 2349-353, 1994.

Kato et al., "Expression of hepatitis beta. virus surface antigen in adult rat liver," J. Biol. Chem., 266:3361-3364, 1991.

Kaufman, "Selection and Coamplification of Heterologous Genes in Mammalian Cells," Methods in Enzymology, 185:537-566, 1990.

Keilholz, U. et al. Immunologic Monitoring of Cancer Vaccine Therapy: Results of a Workshop Sponsored by the Society for Biologic Therapy. J. Immunoth. 25, 97-139 (2002).

Kelleher and Vos, "Long-term episomal gene delivery in human lymphoid cells using human and avian adenoviral-assisted transfection," Biotechniques, 17(6):1110-1117, 1994.

Klein et al., "High-velocity microprojectiles for delivering nucleic acids into living cells," Nature, 327:70-73, 1987.

Kobayashi et al., "EGFR Mutation and Resistance of Non-Small-Cell Lung Cancer to Gefitinib," New Engl J Med, Volume 352:786-792, 2005.

Kolmel, "Cytology of neoplastic meningosis," J. Neurooncol., 38(2-3):121-125, 1998.

Korst, R. J., Mahtabifard, A., Yamada, R. & Crystal, R. G. Effect of adenovirus gene transfer vectors on the immunologic functions of mouse dendritic cells. Mol Ther. 5, 307-15 (2002).

Kosmas, C., Tsavaris, N. B., Malamos, N. A., Vadiaka, M. & Koufos, C. Phase II study of paclitaxel, ifosfamide, and cisplatin as second-line treatment in relapsed small-cell lung cancer. J Clin Oncol. 19, 119-26 (2001).

Kotin, Siniscalco, Samulski, Zhu, Hunter, McLaughlin, Muzyczka, Bems, "Site-specific integration by adeno-associated virus," Proc. Natl. Acad. Sci. USA, 87:2211-2215, 1990.

Kovach, Hartmann, Blaszyk, Cunningham, Schaid, and Sommer, "Mutation detection by highly sensitive methods indicates that p53 gene mutations in breast cancer can have important prognostic value," Proc. Natl. Acad. Sci. USA, 93:1093-1096, 1996.

Kuball, J. et al. Generating p53-specific cytotoxic T lymphocytes by recombinant adenoviral vector-based vaccination in mice, but not man. Gene Ther. 9, 833-43 (2002).

Kurup, Hanna, "Treatment of small cell lung cancer," Crit Rev Oncol Hematol. 52(2):117-26, 2004.

LaFace, Hermonat, Wakeland, Peck, "Gene transfer into hematopoietic progenitor cells mediated by an adeno-associated virus vector," Virology, 162:483-486, 1988.

Laughlin, Cardellichio, Coon, "Latent Infection of KB Cells with Adeno-Associated Virus Type 2," J. Virol., 60:515-524, 1986.

Le Gal La Salle et al., "An adenovirus vector for gene transfer into neurons and glia in the brain," Science, 259:988-990, 1993.

Lebkowski, McNally, Okarma, and Lerch, "Adeno-associated virus: a vector system for efficient introduction and integration of DNA into a variety of mammalian cell types," Mol. Cell. Biol., *:3988-3996, 1988.

Leitner, Ying, Driver, Dubensky, Restifo, "Enhancement of tumor-specific immune response with plasmid DNA replicon vectors," Cancer Res 60(1):51-5, 2000.

Levine, A. J., Momand, J., and Finlay, C. A. "The p53 tumor suppresor gene," Nature, 351:453-456, 1991.

Levrero et al., "Defective and nondefective adenovirus vectors for expressing foreign genes in vitro and in vivo," Gene, 101:195-202, 1991.

Liebermann, Gregory, Hoffman, "AP-1 (Fos/Jun) transcription factors in hematopoietic differentiation and apoptosis," Int. J. Oncol., 12(3):685-700, 1998.

Luo, Zhou, Cooper, Munshi, Boswell, Broxmeyer, Srivastava, "Adeno-associated virus 2 mediated transfer and functional expression of a gene encoding the human granulocyte-macrophage colony-stimulating factor," Blood, 82 (Supp.): 1, 303A, 1994.

Magi-Galluzzi, Murphy, Cangi, Loda, "Proliferation apoptosis and cell cycle regulation in prostatic carcinogenesis," Anal. Quant. Cytol. Histol., 20(5):343-350, 1998.

Mangray and King, "Molecular pathobiology of pancreatic adenocarcinoma," Front Biosci., 3:D1148-1160, 1998.

Mann et al., "Construction of a retrovirus packaging mutant and its use to produce helper-free defective retrovirus," Cell, 33:153-159, 1983.

Markowitz et al., "A safe packaging line for gene transfer: Separating viral genes on two different plasmids," J. Virol., 62:1120-1124, 1988.

Masters, G. A. et al. Phase II trial of gemcitabine in refractory or relapsed small-cell lung cancer: Eastern Cooperative Oncology Group Trial 1597. J Clin Oncol. 21, 1550-5 (2003).

Mathiowitz et al., "Biologically erodable microspheres as potential oral drug delivery systems." Nature, 386:410-414, 1998.

Mayer, Future developments in the selectivity of anticancer agents: drug delivery and molecular target strategies," Cancer Metastasis Rev., 17(2):211-8, 1998.

Mayordomo et al., "Therapy of murine tumors with p53 wild-type and mutant sequence peptide-based vaccines," J. Exp. Med., 183(4):1357-1365, 1996.

McCarty, Christensen, Muzyczka, "Sequences Required for Coordinate Induction of Adeno-Associated Virus p19 and p40 Promoters by Rep Protein," J. Virol., 65:2936-2945, 1991.

McLaughlin, Collis, Hermonat, Muzyczka, "Adeno-Associated Virus General Transduction Vectors: Analysis of Proviral Structures," J. Virol., 62:1963-1973, 1988.

Menard, S., Pupa, S. M., Campiglio, M. & Tagliabue, E. Biologic and therapeutic role of HER2 in cancer. Oncogene. 22, 6570-8 (2003).

Miller, G., Lahrs, S., Pillarisetty, V. G., Shah, A. B. & DeMatteo, R. P. Adenovirus infection enhances dendritic cell immunostimulatory properties and induces natural killer and T-cell-mediated tumor protection. Cancer Res. 62, 5260-6 (2002).

Miller, G., Lahrs, S., Shah, A. B. & DeMatteo, R. P. Optimization of dendritic cell maturation and gene transfer by recombinant adenovirus. Cancer Immunol Immunother. 52, 347-58 (2003).

Mougin, Bernard, Lab, "Biology of papillomavirus II infections. Their role in the carcinogenesis of the cervix," Ann. Biol. Clin. (Paris), 56(1):21-8, 1998.

Mumby and Walter, "Protein phosphatases and DNA tumor viruses: transformation through the back door?" Cell Regul., 2(8):589-598, 1991.

Munz C, Steinman R M, Fujii S. Dendritic cell maturation by innate lymphocytes: coordinated stimulation of innate and adaptive immunity. J Exp Med. July 18; 202(2):203-7, 2005.

Murakami, T. et al. Antitumor effect of intratumoral administration of bone marrow-derived dendritic cells transduced with wild-type p53 gene. Clin Cancer Res. 10, 3871-80 (2004).

Muzyczka, "Use of Adeno-Associated Virus as a General Transduction Vector for Mammalian Cells," Curr. Top. Microbiol. Immunol., 158:97-129, 1992.

Natoli, Costanzo, Guido, Moretti, Levrero, Apoptotic, non-apoptotic, and anti-apoptotic pathways of tumor necrosis factor signalling," Biochem. Pharmacol., 56(8):915-920, 1998.

Nicolas and Rubinstein, "Retroviral vectors," In: Vectors: A survey of molecular cloning vectors and their uses, Rodriguez and Denhardt (eds.), Stoneham: Butterworth, pp. 494-513, 1988.

Nicolau and Sene, "Liposome-mediated DNA transfer in eukaryotic cells," Biochem. Biophys. Acta, 721:185-190, 1982.

Nijman et al., "p53, a potential target for tumor-directed T cells," Immunol. Letters, 40:171-178, 1994.

Nikitina, E. Y. et al. An effective immunization and cancer treatment with activated dendritic cells transduced with full-length wild-type p53. Gene Therapy. 9, 345-352 (2002).

Nikitina, E. Y. et al. Dendritic cells transduced with full-length wild-type p53 generate antitumor cytotoxic T lymphocytes from peripheral blood of cancer patients. Clin Cancer Res. 7, 127-35. (2001).

Nikitina, E. Y. et al. Dendritic Cells Transduced with Full-Length Wild-Type p53 Generate Antitumor Cytotoxic T Lymphocytes from Peripheral Blood of Cancer Patients. Clin Cancer Res. 7, 127-135 (2001).

Nociari et al., "A novel one-step, highly sensitive fluorometric assay to evaluate cell-mediated cytotoxicity," J. Immunol. Methods, 213(2): 157-167, 1998.

Noguchi, Y., Chen, Y. & Old, L. A mouse mutant p53 product recognized by CD4+ and CD8+ T cells. Proc. Natl. Acad. Sci. USA. 91, 3171-3175 (1994).

Ochi, Hasuoka, Mizushima, Matsumura, Harada, "A case of small pancreatic cancer diagnosed by serial follow-up studies promptly by a positive K-ras point mutation in pure pancreatic juice," Am. J. Gastroenterol., 93(8):1366-1368, 1998.

Ohara, "Radiotherapy: a significant treatment option in management of prostatic cancer," Gan. To. Kagaku. Ryoho., 25(6):823-8, 1998.

Ohi, Dixit, Tillery, and Plonk, "Construction and replication of an adeno-associated virus expression vector that contains human .lambda.-globin cDNA," Gene, 89L:279-282, 1990.

Oldstone et al., "A common antiviral cytotoxic T-lymphocyte epitope for diverse major histocompatibility complex haplotypes: implications for vaccination," Proc. Natl. Acad. Sci. USA, 89:2752-2755, 1992.

Ono, Hirose, Miyazaki, Yamamoto, Matsumoto, "Transgenic medaka fish bearing the mouse tyrosinase gene: expression and transmission of the transgene following electroporation of the orange-colored variant," Pigment Cell Res., 10(3): 168-175, 1997.

Page et al., "A non isotopic method for the meausrement of cell membrane integrity," Anticancer Res., 18(4A):2313-2316, 1998.

Parajuli, P. et al. Immunization with wild-type p53 gene sequences coadministered with Flt3 ligand induces an antigen-specific type 1 T-cell response. Cancer Res. 61, 8227-34 (2001).

Paskind et al., "Dependence of moloney murine leukemia virus production on cell growth," Virology, 67:242-248, 1975.

Pelletier and Sonenberg, Nature, 334:320-325, 1988.

Perales et al., Proc. Natl. Acad. Sci. USA, 91:4086-4090, 1994.

Philpott, N. J., Nociari, M., Elkon, K. B. & Falck-Pedersen, E. Adenovirus-induced maturation of dendritic cells through a PI3 kinase-mediated TNF-alpha induction pathway. Proc Natl Acad Sci USA. 101, 6200-5 (2004).

Pietras, Pegram, Finn, Maneval, Slamon, "Remission of human breast cancer xenografts on therapy with humanized monoclonal antibody to HER-2 receptor and DNA-reactive drugs," Oncogene, 17(17):2235-49, 1998.

Pinto-Sietsma and Paul, "Transgenic rats as models for hypertension," J. Hum. Hypertens., 11(9):577-581, 1997.

Pisarev, V. et al. Full-Length Dominant-Negative Survivin for Cancer Immunotherapy. Clin Cancer Res. 15, 6523-6533 (2003).

Porgador et al., "Intranasal immunization with cytotoxic T-lymphocyte epitope peptide and mucosal adjuvant cholera toxin: selective augmentation of peptide-presenting dendritic cells in nasal mucosa-associated lymphoid tissue," Infect. Immun., 66(12):5876-5881, 1998.

Potter et al., "Enhancer-dependent expression of human k immunoglobulin genes introduced into mouse pre-B lymphocytes by electroporation," Proc. Nat'l Acad. Sci. USA, 81:7161-7165, 1984.

Qin, Tao, Dergay, Moy, Fawell, Davis, Wilson, Barsoum, "Interferon-beta gene therapy inhibits tumor formation and causes regression of established tumors in immune-deficient mice," Proc. Natl. Acad. Sci. USA, 95(24):1411-6, 1998.

Racher et al., Biotechnology Techniques, 9:169-174, 1995.

Ragot et al., "Efficient adenovirus-mediated transfer of a human minidystrophin gene to skeletal muscle of mdx mice," Nature, 361:647-650, 1993.

Renan, "Cancer genes: current status, future prospects, and applicants in radiotherapy/oncology," Radiother. Oncol., 19:197-218, 1990.

Rich et al., "Development and analysis of recombinant adenoviruses for gene therapy of cystic fibrosis," Hum. Gene Ther., 4:461-476, 1993.

Ridgeway, "Mammalian expression vectors," In: Rodriguez R L, Denhardt D T, ed. Vectors: A survey of molecular cloning vectors and their uses. Stoneham: Butterworth, pp. 467-492, 1988.

Rippe et al., "DNA-mediated gene transfer into adult rat hepatocytes in primary culture," Mol. Cell Biol., 10:689-695, 1990.

Ropke et al., "Spontaneous human squamous cell carcinomas are killed by a human cytotoxic T lymphocyte clone recognizing a wild-type p53-derived peptide," Proc. Natl. Acad. Sci. USA, 93:14704-14707, 1996.

Rosenberg, S. A., Yang, J. C. & Restifo, N. P. Cancer immunotherapy: moving beyond current vaccines. Nat Med. 10, 909-15 (2004).

Rosenfeld et al., "Adenovirus-mediated transfer of a recombinant a1-antitrypsin gene to the lung epithelium in vivo," Science, 252:431-434, 1991.

Rosenfeld et al., "In vivo transfer of the human cystic fibrosis transmembrane conductance regulator gene to the airway epitheliurm," Cell, 68:143-155, 1992.

Roth, J. A. & Cristiano, R. J. Gene therapy for cancer: what have we done and where are we going? J. Natl. Cancer Inst. 89, 21-39 (1997).

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," Proc. Natl. Acad. Sci. USA, 86:9079-9083, 1989.

Samulski, Chang, Shenk, "Helper-free stocks of recombinant adeno-associated viruses: Normal integration does not require viral gene expression," J. Virol., 63:3822-3828, 1989.

Samulski, Zhu, Xiao, Brook, Housman, Epstein, Hunter, "Targeted integration of adeno-associated virus (AAV) into human chromosome 19," EMBO J., 10:3941-3950, 1991.

Sandler, A. B. Irinotecan in small-cell lung cancer: the US experience. Oncology (Huntingt). 15, 11-2(2001).

Santerre, et al., Gene, 30:147, 1984

Saurwein-Teissl et al., "Whole virus influenza vaccine activates dendritic cells (DC) and stimulates cytokine production by peripheral blood mononuclear cells (PBMC) while subunit vaccines support T cell proliferation," Clin. Exp. Immunol., 114(2):271-276, 1998.

Schumacher, L. et al. Human dendritic cell maturation by adenovirus transduction enhances tumor antigen-specific T-cell responses. J Immunother. 27, 191-200 (2004).

Shelling and Smith, "Targeted integration of transfected and infected adeno-associated virus vectors containing the neomycin resistance gene," Gene Therapy, 1:165-169, 1994.

Simpson et al., "Consequences of Fas-ligand and perforin expression by colon T cells in a mouse model of inflammatory bowel disease," Gastroenterology, 115(4):849-855, 1998.

Sirianni, N. et al. Effect of human papillomavirus-16 infection on CD8+ T-cell recognition of a wild-type sequence p53264-272 peptide in patients with squamous cell carcinoma of the head and neck. Clin Cancer Res. 10, 6929-37 (2004).

Soddu and Sacchi, "p53: prospects for cancer gene therapy," Cytokines Cell Mol. Ther., 4(3):177-185, 1998.

Solyanik, Berezetskaya, Bulkiewicz, Kulik, "Different growth patterns of a cancer cell population as a function of its starting growth characteristics: analysis by mathematical modelling," Cell Prolif., 28(5):263-278, 1995.

Sonderbye et al., "In vivo and in vitro modulation of immune stimulatory capacity of primary dendritic cells by adenovirus-mediated gene transduction," Exp. Clin. Immunogenet., 15(2):100-111, 1998.

Steinman, "The dendritic cell system and its role in immunogenecity," Annu. Rev. Immunol., 9:271-296, 1991.

Stokke, Smedshammer, Jonassen, Blomhoff, Skarstad, Steen, "Uncoupling of the order of the S and M phases: effects of staurosporine on human cell cycle kinases," Cell Prolif., 30(5):197-218, 1997.

Stratford-Perricaudet and Perricaudet, "Gene transfer into animals: the promise of adenovirus," In: Human Gene Transfer, Eds, O. Cohen-Haguenauer and M. Boiron, Editions John Libbey Eurotext, France, p. 51-61, 1991.

Stratford-Perricaudet et al., "Evaluation of the transfer and expression in mice of an enzyme-encoding gene using a human adenovirus vector," Hum. Gene Ther., 1:241-256, 1990.

Svane, I. M. et al. Vaccination with p53-peptide-pulsed dendritic cells, of patients with advanced breast cancer: report from a phase I study. Cancer Immunol Immunother. 53, 633-41 (2004).

Temin, "Retrovirus vectors for gene transfer: Efficient integration into and expression of exogenous DNA in vertebrate cell genome," In: Gene Transfer, Kucherlapati (ed.), New York, Plenum Press, pp. 149-188, 1986.

Theobald et al., "Targeting p53 as a general tumor antigen," Proc. Natl. Acad. Sci. USA, 92:11993011997, 1995.

Theobald, M. et al. The sequence alteration associated with a mutational hotspot in p53 protects cells from lysis by cytotoxic T lymphocytes specific for a flanking peptide epitope. J Exp Med. 188, 1017-28 (1998).

Thomas P, et al. "Phase II trial of paclitaxel and carboplatin in metastatic small-cell lung cancer: a Groupe Francais de Pneumo-Cancerologie study." J Clin Oncol., 19(5):1320-5, 2001.

Thomson, S. A. et al. Minimal epitopes expressed in a recombinant polyepitope protein are processed and presented to CD8+ cytotoxic T cells: implications for vaccine design. Proc. Natl. Acad. Sci. USA. 92, 5845-5849 (1995).

Top et al., "Immunization with live types 7 and 4 adenovirus vaccines. II. Antibody response and protective effect against acute respiratory disease due to adenovirus type 7," J. Infect. Dis., 124:155-160, 1971.

Tratschin, Miller, Smith, Carter, "Adeno-associated virus vector for high-frequency integration, expression and rescue of genes in mammalian cells," Mol. Cell. Biol., 5:32581-3260, 1985.

Tratschin, West, Sandbank, Carter, "A human parvovirus, adeno-associated virus, as a eucaryotic vector: transient expression and encapsidation of the procaryotic gene for chloramphenicol acetyltransferase," Mol. Cell. Biol., 4:2072-2081, 1984.

Tur-Kaspa et al., "Use of electroporation to introduce biologically active foreign genes into primary rat hepatocytes," Mol. Cell Biol., 6:716-718, 1986.

Van Cott, Lubon, Russell, Butler, GwazdauskasKnight, Drohan, Velander, "Phenotypic and genotypic stability of multiple lines of transgenic pigs expressing recombinant human protein C," Transgenic Res., 6(3):203-212, 1997.

van der Burg, S. H. et al. Induction of p53-specific immune responses in colorectal cancer patients receiving a recombinant ALVAC-p53 candidate vaccine. Clin Cancer Res. 8, 1019-27 (2002).

van der Burg, S. H. et al. Magnitude and polarization of P53-specific T-helper immunity in connection to leukocyte infiltration of colorectal tumors. Int J Cancer. 107, 425-33 (2003).

Vierboom, M. P. M. et al. Tumor eradication by wild-type p53-specific cytotoxic T lymphocytes. J. Exper. Med. 186, 695-704 (1997).

Vierboom, M. P. M., Gabrilovich, D. I., Offringa, R., Kast, W. M. & Melief, C. J. M. p53: a target for T-cell mediated immunotherapy. in Peptide-based Cancer Vaccines (ed. Kast, W. M.) 40-55 (Landes Bioscience, 2000).

Vogelstein and Kinzler, "p53 function and dysfunction," Cell, 70(4):523-526, 1992.

Wagner et al., Science, 260:1510-1513, 1990.

Wahlstrom et al., Mol. Endrocrinol., 6:1013-1022, 1992.

Walsh, Nienhuis, Samulski, Brown, Miller, Young, Liu, "Phenotypic correction of Fanconi anemia in human hematopoietic cells with a recombinant adeno-associated virus vector," Proc. Natl. Acad. Sci. USA, 89:7257-7261, 1994; J. Clin. Invest., 94:1440-1448, 1994.

Wan, Y., Bramson, J., Carter, R., Graham, F. & Gauldie, J. Dendritic cells transduced with an adenoviral vector encoding a model tumor-associated antigen for tumor vaccination. Human Gene Therapy. 8, 1355-1363 (1997).

Watanabe, M., Shirayoshi, Y., Koshimizu, U., Hashimoto, S., Yonehara, S., Eguchi, Y., Tsujimoto, Y. and Nakatsuji, N., "Gene transfection of mouse primordial germ cells in vitro and analysis of their survival and growth control," Exp. Cell Res. 230:76-83, 1997.

Wei, Wei, Samulski, Barranger, "Expression of the human glucocerebrosidase and arylsulfatase A genes in murine and patient primary fibroblasts transduced by an adeno-associated virus vector," Gene Therapy, 1:261-268, 1994.

Wheeler, C. J., Das, A., Liu, G., Yu, J. S. & Black, K. L. Clinical responsiveness of glioblastoma multiforme to chemotherapy after vaccination. Clin Cancer Res. 10, 5316-26 (2004).

Wong et al., "Appearance of .beta.-lactamase activity in animal cells upon liposome mediated gene transfer," Gene, 10:87-94, 1980.

Wu and Wu, "Evidence for targeted gene delivery to HepG2 hepatoma cells in vitro," Biochemistry, 27:887-892, 1988.

Wu and Wu, "Receptor-mediated in vitro gene transfections by a soluble DNA carrier system," J. Biol. Chem., 262: 4429-4432, 1987.

Wu and Wu, Adv. Drug Delivery Rev., 12:159-167, 1993.

Yang et al., "In vivo and in vitro gene transfer to mammalian somatic cells by particle bombardment," Proc. Nat'l Acad. Sci. USA, 87:9568-9572, 1990.

Yang, Chen, Trempe, "Characterization of cell lines that inducibly express the adeno-associated virus Rep proteins," J. Virol., 68:4847-4856, 1994.

Yanuck, Carbone, Pendleton, Tsukui, Winter, Minna, Berzofsky, "A mutant p53 tumor suppressor protein is a target for peptide-induced CD8+cytotoxic T-cells, Cancer Res., 53(14):3257-61, 1993.

Yanuck, M. et al. Mutant p53 tumor suppressor protein is a target for peptide-induced CD8+ cytotoxic T-cells. Cancer research. 53, 3257-3261 (1993).

Yeom, Fuhlrmann, Ovitt, Brehm, Ohbo, Gross, Huibner, Scholer, "Germline regulatory element of Oct-4 specific for totipotent cycle of embryonal cells," Development, 122:881-894, 1996.

Yoder, Kang, Zhou, Luo, Srivastava, "In vivo gene transfer in murine hematopoietic reconstituting stem cells mediated by the adeno-associated virus 2-based vectors," Blood, 82 (Supp.):1:347A, 1994.

Zhou, Broxmyer, Cooper, Harrington, Srivastava, "Adeno-associated virus 2 mediated gene transfer in murine hematopoietic cells, Exp. Hematol. (NY), 21:928-933, 1993.

Zhou, Cooper, Kang, Ruggieri, Heimfeld, Srivastava, Broxmeyer, "Adeno-associated virus 2-mediated high efficiency gene transfer into immature and mature subsets of hematopoietic progenitor cells in human umbilical cord blood," J. Exp. Med., 179:1867-1875, 1994.

Zwaveling, S. et al. Antitumor efficacy of wild-type p53-specific CD4(+) T-helper cells. Cancer Res. 62, 6187-93 (2002).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

---

What is claimed is:

1. A method of conferring chemotherapeutic agent sensitivity to a chemotherapeutic agent resistant tumor in a subject comprising providing to the subject a dendritic cell comprising a p53 expression construct, the expression construct comprising a p53 gene under control of a promoter operable in the dendritic cell, wherein chemotherapeutic agent sensitivity is conferred to the tumor; and then providing a chemotherapy comprising the chemotherapeutic agent to the chemotherapeutic agent sensitized tumor in the subject.

2. The method of claim 1, wherein the chemotherapeutic agent is paclitaxel, topotecan, cisplatin, carboplatin, doxorubicin, cyclophosphamide, or docetaxel.

3. The method of claim 1, wherein the chemotherapeutic agent is an alkylating agent.

4. The method of claim 3, wherein the alkylating agent is busulfan, cisplatin, or ifosfamide.

5. The method of claim 1, wherein the chemotherapy is an anthracycline.

6. The method of claim 5, wherein the anthracycline is doxorubicin or epirubicin.

7. The method of claim 1, wherein the chemotherapy is an anti-metabolite.

8. The method of claim 7, wherein the anti-metabolite is fluorouracil or methotrexate.

9. The method of claim 1, wherein the chemotherapy is a topoisomerase inhibitor.

10. The method of claim 9, wherein the topoisomerase inhibitor is bleomycin, etoposide, or gemcitabine.

11. The method of claim 1, wherein the chemotherapy is a microtubule inhibitor.

12. The method of claim 11, wherein the microtubule inhibitor is taxol or vinblastine.

13. The method of claim 1, wherein the chemotherapy comprises a composition that upregulates expression of p53, Fas, a death receptor, or a combination thereof.

14. The method of claim 1, wherein the chemotherapeutic agent is provided to the subject within about one to twelve months of providing the dendritic cell to the subject.

15. The method of claim 14, wherein the chemotherapeutic agent is provided to the subject within one to two months of providing the dendritic cell to the subject.

16. The method of claim 1, wherein the dendritic cell and the chemotherapy are provided more than once.

17. The method of claim 16, wherein the dendritic cell and the chemotherapy are provided in cycles.

18. The method of claim 1, wherein the tumor is a metastasized tumor.

19. The method of claim 1, wherein the tumor is small cell lung cancer.

20. The method of claim 1, wherein the tumor is lung cancer, breast cancer, colon cancer, melanoma, liver cancer, brain cancer, prostate cancer, kidney cancer, sarcoma, pancreatic cancer, lymphoma, or leukemia.

21. The method of claim 1, further comprising delivering to the subject an enhancing agent selected from CD40 antibody, TNF-alpha, GM-CSF, IL-1, IL-4, FLT-3 ligand or CD 40.

22. The method of claim 21, wherein the enhancing agent comprises a CD40 antibody.

23. The method of claim 21, wherein the dendritic cell expressing the p53 gene product and the enhancing agent are comprised in the same composition.

24. The method of claim 21, wherein the dendritic cell expressing the p53 gene product and the enhancing agent are comprised in separate compositions.

25. The method of claim 24, wherein the dendritic cell expressing the p53 gene product and the enhancing agent are delivered to the subject at the same time.

26. The method of claim 24, wherein the dendritic cell expressing the p53 gene product is delivered to the subject prior to delivery of the enhancing agent to the subject.

27. The method of claim 24, wherein the dendritic cell expressing the p53 gene product is delivered to the subject subsequent to delivery of the enhancing agent to the subject.

28. The method of claim 1, wherein the subject has previously been treated with chemotherapy, radiation, or both.

29. The method of claim 1, further comprising the step of assaying a sample of cells from the subject for overexpression of the p53-gene product.

30. The method of claim 29, wherein the sample comprises a biopsy, blood, urine, cheek scrapings, saliva, cerebrospinal fluid, feces, nipple aspirate, or a combination thereof.

31. The method of claim 29, further defined as assaying the sample for a therapy-resistance marker.

32. The method of claim 31, wherein the therapy-resistance marker comprises a mutation in a polynucleotide in one or more of the hyperproliferative cells.

33. A method of treating one or more cancer cells in a subject who has been determined to have cancer cells that are resistant to a chemotherapeutic agent, comprising providing to said subject a dendritic cell expressing a p53 gene product and then the chemotherapeutic agent.

34. The method of claim 33, further comprising delivering to the subject an agent that enhances the activity of the dendritic cell expressing the p53 gene product; wherein the enhancing agent is CD40 antibody, TNF-alpha, GM-CSF, IL-1, IL-4, FLT-3 ligand or CD 40.

35. The method of claim 33, wherein said cancer cells are characterized by increased expression of the p53 gene product.

* * * * *